(12) United States Patent
Leroy

(10) Patent No.: US 9,057,726 B2
(45) Date of Patent: Jun. 16, 2015

(54) NEUROPEPTIDE Q AS MODULATOR OF GPCR GALR2 AND USES THEREOF

(75) Inventor: Xavier Leroy, Allschwil (CH)

(73) Assignee: Actelion Pharmaceuticals Ltd., Allschwil (CH)

(*) Notice: Subject to any disclaimer, the term of this patent is extended or adjusted under 35 U.S.C. 154(b) by 41 days.

(21) Appl. No.: 13/876,447

(22) PCT Filed: Sep. 23, 2011

(86) PCT No.: PCT/IB2011/054205
§ 371 (c)(1),
(2), (4) Date: Apr. 17, 2013

(87) PCT Pub. No.: WO2012/042455
PCT Pub. Date: Apr. 5, 2012

(65) Prior Publication Data
US 2013/0196348 A1  Aug. 1, 2013

(30) Foreign Application Priority Data
Sep. 28, 2010 (WO) .................. PCT/IB2010/054369

(51) Int. Cl.
*G01N 33/566* (2006.01)

(52) U.S. Cl.
CPC ...... *G01N 33/566* (2013.01); *G01N 2333/5755* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 4,873,191 A | 10/1989 | Wagner et al. | |
| 5,888,819 A | 3/1999 | Goelet et al. | |
| 5,919,649 A | 7/1999 | Habener et al. | |
| 5,972,624 A | 10/1999 | Smith et al. | |
| 6,004,744 A | 12/1999 | Goelet et al. | |
| 6,013,431 A | 1/2000 | Soderlund et al. | |
| 2005/0221358 A1 | 10/2005 | Carrillo et al. | |

FOREIGN PATENT DOCUMENTS

| | | |
|---|---|---|
| FR | 2593827 | 8/1987 |
| WO | WO 02/096934 | 12/2002 |

OTHER PUBLICATIONS

Abramov, Urho et al., "Regulation of Feeding by Galnon," Neuropeptides (2003), No. 38, pp. 55-61.
Ahmad, Sultan et al., "Cloning and Evaluation of the Role of Rat GALR-2, a Novel Subtype of Galanin Receptor, in the Control of Pain Perception," Ann. N.Y. Acad. Sci. (1998), No. 863, pp. 108-119.
Bloomquist et al., "Cloning and Expression of the Human Galanin Receptor GalR2¹," Biophys. Res. Commun. (1998) 243, pp. 474-479.
Branchek et al., "Galanin Receptor Subtypes" Trends Pharmcol Sci (2000) 21, pp. 109-117.
Brecht et al., "Persisting expression of galanin in axotomized mamillary and septal neurons of adult rats labeled for c-Jun and NADPH-diaphorase" Brain Res. Mol. Brain Res. (1997) 48, pp. 7-16.
Burgevin et al., "Cloning, Pharmacological Characterization, and Anatomical Distribution of a Rat cDNA Encoding for a Galanin Receptor," J. Mol. Neurosci. (1995) 6, pp. 33-41.
Chang et al., "Amino-Acid Sequence of Substance P" Nat. New. Biol. (1971) 232, pp. 86-87.
Cole et al., "The EBV-Hybridoma Technique and its Application to Human Lung Cancer" Monoclonal Antibodies and Cancer Therapy, Alan R. Liss, Inc. (1985) pp. 77-96.
Comb et al., "A Cyclic AMP- and Phorbol Ester-Inducibe DNA Element" Nature, (1986) 323, 353-356.
Cortes et al., "Effects of Central Nervous System Lesions on the Expression of Galanin: A Comparative in Situ Hybridization and Immunohistochemical Study" Proc. Natl. Acad. Sci. USA (1990) 87, pp. 7742-7746.
Costagliola et al., "Genetic Immunization of Outbred Mice With Thyrotropin Receptor Cdna Provides a Model of Graves' Disease" J. Clin. Invest., (2000) 105, pp. 803-811.
Crawley, "Galanin Impairs Cognitive Abilities in Rodents: Relevance to Alzheimer's Disease" Cell. Mol. Life Sci. (2008) 65, pp. 1836-1841.
Detheux et al., "Natural Proteolytic Processing of Hemofiltrate CC Chemokine 1 Generates a Potent CC Chemokine Receptor (CCR)1 and CCR5 Agonist with Anti-HIV Properties" J. Exp. Med., (2000) 192, pp. 1501-1508.
Fathi et al., "Cloning, Pharmacological Characterization and Distribution of a Novel Galanin Receptor" Brain Res. Mol. Brain Res. 51, 49-59, 1997.
Fink et al., "The CGTCA Sequence Motif Is Essential for Biological Activity of the Vasoactive Intestinal Peptide Gene cAMP-Regulated Enhancer" Proc. Natl. Acad. Sci., (1988) 85, pp. 6662-6666.
Fisone et al., "Galanin Inhibits Acetylcholine Release in the Ventral Hippocampus of the Rat: Histochemical, Autoradiographic, In Vivo, and In Vitro Studies" Proc. Natl. Acad. Sci. USA (1987) 84, 7339-7343.
Ghattas et al., "The Encephalomyocarditis Virus Internal Ribosome Entry Site Allows Efficient Coexpression of Two Genes from a Recombinant Provirus in Cultured Cells and in Embryos" Mol. Cell. Biol., (1991) 11, 5848-5859.
Habert-Ortoli et al., "Molecular Cloning of a Functional Human Galanin Receptor" Proc. Natl. Acad. Sci. USA (1994) 91, pp. 9780-9783.
Hafner., "Cytosensor® Microphysiometer: Technology and Recent Applications" Biosens. Bioelectron., 15, 149-158, (2000).
Harrison and Henderson, "Quantitative Evidence for Increase in Galanin-Immunoreactive Terminals in the Hippocampal Formation Following Entorhinal Cortex Lesions in the Adult Rat" (1999) Neurosci. Lett. 266, pp. 41-44.
Hawes et al., Characterization of GalR1, GalR2, and GalR3 Immunoreactivity in Catecholaminergic Nuclei of the Mouse Brain J. Comp. Neurol. (2004) 479, pp. 410-423.
Hokfelt et al., "Galanin in Ascending Systems" Ann. N.Y. Acad. Sci. (1998) 863, 252-263.

(Continued)

Primary Examiner — Michael Pak
(74) Attorney, Agent, or Firm — Hunton & Williams LLP

(57) ABSTRACT

The invention relates to the identification of Neuropeptide Q as ligand of the GALR2 GPCR (G-protein coupled receptor). The invention encompasses the use of the interaction of GALR2 polypeptides and Neuropeptide Q polypeptides as the basis of screening assays for agents that modulate the activity of the GALR2 receptor. The invention also encompasses diagnostic assays based upon the GALR2/Neuropeptide Q polypeptide interaction, as well as kits for performing diagnostic and screening assays.

19 Claims, 18 Drawing Sheets

(56) References Cited

OTHER PUBLICATIONS

Hokfelt et al., "Neuropeptides: Opportunities for Drug Discovery" Lancet Neurol. (2003) 2, pp. 463-472.

Hokfelt et al., "Peptidergic Neurones" Nature (1980) 284, pp. 525-521.

Hokfelt et al., "Increase of Galanin-Like Immunoreactivity in Rat Dorsal Root Ganglion Cells After Peripheral Axotomy" Neurosci. Lett. (1987) 83, 217-220.

Horton and Baxendale, "Mass Measurements of Cyclic AMP Formation by Radioimmunoassay, Enzyme Immunoassay, and Scintillation Proximity Assay" Methods Mol. Biol., (1995) 41, pp. 91-105.

Howard et al., "Molecular Cloning and Characterization of a New Receptor for Galanin" FEBS Letts. (1997) 405, pp. 285-290.

Hubbart and Cohn, "Externally Disposed Plasma Membrane Proteins" J. Cell. Biol., (1975) 64, pp. 461-479.

Huszar et al., "Targeted Disruption of the Melanocortin-4 Receptor Results in Obesity in Mice" Cell, (1997) 88, 131.

Kanazawa et al., "Galanin Receptor Subtypes 1 and 2 as Therapeutic Targets in Head and Neck Squamous Cell Carcinoma" Expert Opin. Ther. Targets (2010) 14, pp. 289-302.

Kenimer and Nirenberg, "Desensitization of Adenylate Cyclase to Prostaglandin E1 or 2-Chioroadenosine" Mol. Pharmacol., (1981) 20, pp. 585-591.

Kikkawa et al., "Calcium-activated, Phospholipid-dependent Protein Kinase from Rat Brain" J. Biol. Chem., (1982) 257, pp. 13341-13348.

Kinney et al., "Galanin Receptor-Mediated Inhibition of Glutamate Release in the Arcuate Nucleus of the Hypothalamus" J. Neurosci. (1998) 18, 3489-3500.

Kinney et al., "Impairment of Memory Consolidation by Galanin Correlates with in vivo Inhibition of both LTP and CREB Phosphorylation" Neurobiol. Learn. Mem. (2009) 92, pp. 429-438.

Kjelsberg et al., "Constitutive Activation of the alBAdrenergic Receptor by All Amino Acid Substitutions at a Single Site" J. Biol. Chem. (1992) 267, pp. 1430-1433.

Kohler and Milstein, "Continuous Cultures of Fused Cells Secreting Antibody of Predefined Specificity" Nature, (1975) 256, 495-497.

Kolakowski et al., "Molecular Characterization and Expression of Cloned Human Galanin Receptors GALR2 and GALR3" J. Neurochem. (1998) 71, pp. 2239-2251.

Kozbor et al., "The Production of Monoclonal Antibodies from Human Lymphocytes" Immunology Today, (1983) 4, 72.

Kramer et al., "Distinct Mechanism for Antidepressant Activity by Blockade of Central Substance P Receptors" Science (1998) 281, pp. 1640-1645.

Liu et al., "Receptor subtype-specific pronociceptive and analgesic actions of galanin in the spinal cord: Selective actions via GalR1 and GalR2 receptors" Proc. Natl. Acad. Sci USA (2001) 98, pp. 9960-9964.

Lu Xiaoying et al., "Galanin Receptor Ligands" Neuropeptides. (2005) 39, pp. 143-146.

Lu Xiaoying et al., "A Role for Galanin in Antidepressant Actions with a Focus on the Dorsal Raphe Nucleus" Proc. Natl. Acad. Sci. USA (2005) 102, 874-879.

Mastropaolo et al., "Galanin Antagonizes Acetylcholine on a Memory Task in Basal Forebrain-Lesioned Rats" Proc. Natl. Acad. Sci. USA (1998) 85, pp. 9841-9845.

Mazarati et al., "Anticonvulsive Effects of Galanin Administered into the Central Nervous System upon the Picrotoxin-Kindled Seizure Syndrome in Rats" Brain Res. (1992) 589, pp. 164-166.

Mazarati et al., "In Vivo Interaction Between Serotonin and Galanin Type 1 and Type 2 Receptors in Dorsal Raphe: Implication for Limbic Seizures" J. Neurochem. (2005) 95, pp. 1495-1503.

Mazarati et al., "Regulation of Kindling Epileptogenesis by Hippocampal Galanin Type 1 and Type 2 Receptors: The Effects of Subtype Selective Agonists and the Role of G-Protein Mediated Signaling." J. Pharmacol. Exp. Ther. (2006) 318, pp. 700-708.

McWhinney et al., "Constitutively Active Mutants of the a1a- and the a1b-Adrenergic Receptor Subtypes Reveal Coupling to Different Signaling Pathways and Physiological Responses in Rat Cardiac Myocytes*" J. Biol. Chem., (2000) 275, pp. 2087-2097.

Mirabeau et al., "Identification of Novel Peptide Hormones in the Human Proteome by Hidden Markov Model Screening" Genome Res., (2007) 17, pp. 320-327.

Misane et al., "Intraventricular Galanin Modulates a 5-Ht1a Receptormediated Behavioural Response in the Rat" Eur. J. Neurosci. (1998) 10, pp. 1230-1240.

Mishizuma and Nagata, "pEF-BOS, a powerful mammalian expression vector" Nucl. Acids Res., (1990) 18, p. 5322.

Montminy et al., "Identification of a Cyclic-Amp-Responsive Element Within the Rat Somatostatin Gene" Proc. Natl. Acad. Sci., (1986) 83, pp. 6682-6686.

O'Donnell et al., "Expression of the Novel Galanin Receptor Subtype GALR2 in the Adult Rat CNS: Distinct Distribution From GALR1" J. Comp. Neurol. (1999) 409, pp. 469-481.

Ohki-Hamazaki et al., "Mice Lacking Bombesin Receptor Subtype-3 Develop Metabolic Defects and Obesity" Nature, (1997) 390, pp. 165-169.

Palmiter and Brinster, "Germ-Line Transformation of Mice" Ann. Rev. Genet., (1986) 20, pp, 465-499.

Parma et al., "Somatic Mutations in the Thyrotropin Receptor Gene Cause Hyperfunctioning Thyroid Adenomas" Nature, (1993) 365, pp. 649-651.

Pieribone et al., "Galanin Induces a Hyperpolarization of Norepinephrine-Containing Locus Coeruleus Neurons in the Brainstem Slice" Neurosci. (1995) 64, pp. 861-876.

Pinna and Ruzzene, "How Do Protein Kinases Recognize Their Substrates?" Biochem. Biophys. Acta., (1996) 1314, pp. 191-225.

Ren et al., "Constitutively Active Mutants of the az-Adrenergic Receptor" J. Biol. Chem., (1993) 268, pp. 16483-16487.

Rudolph et al., "Expression, Characterization, and Mutagenesis of the *Yersinia pestis* Murine Toxin, a Phospholipase D Superfamily Member*" J. Biol. Chem., (1999) 274, pp. 11824-11831.

Saar et al., "Anticonvulsant Activity of a Nonpeptide Galanin Receptor Agonist" Proc. Natl. Acad. Sci. USA (2002) 99, pp. 7136-7141.
Sakurai et al., "Galanin Inhibits Long-Term Potentiation at Schaffer Collateral-Ca1 Synapses in Guinea-Pig Hippocampal Slices" Neurosci. Lett. (1996) 212, pp. 21-24.
Salamon et al, "Optical Anisotropy in Lipid Bilayer Membranes: Coupled Plasmon-Waveguide Resonance Measurements of Molecular Orientation, Polarizability, and Shape" Biophys. J., (2001) 80, pp. 1557-1567.
Salamon et al., "Plasmon Resonance Spectroscopy: Probing Molecular Interactions Within Membranes" Trends Biochem. Sci., (1999) 24, pp. 213-219.
Salamon et al., "Surface Plasmon Resonance Spectroscopy Studies of Membrane Proteins: Transducin Binding and Activation by Rhodopsin Monitored in Thin Membrane Films" Biophys. J., (1996) 71, pp. 283-294.
Sarrio et al., "The Heat Shock Cognate Protein hsc73 Assembles with A1 Adenosine Receptors to Form Functional Modules in the Cell Membrane" Mol. Cell. Biol., (2000) 20, pp. 5164-5174.
Short et al., "Characterization of the Phosphoenolpyruvate Carboxykinase (GTP) Promoter-regulatory Region" J. Biol. Chem., (1986) 261, pp. 9721-9726.
Smith et al., "Expression Cloning of a Rat Hypothalamic Galanin Receptor Coupled to Phosphoinositide Turnover*" J. Biol. Chem. 272, 24612-24616, 1997.
Smith et al., "Cloned Human and Rat Galanin GALR3 Receptors" J. Biol. Chem. (1998) 273, pp. 23321-23326.
Stables et al., "A Bioluminescent Assay for Agonist Activity at Potentially Any G-Protein-Coupled Receptor" Anal. Biochem., (1997) 252, pp. 115-126.
Tajib et al., "Paramagnetic Proteoliposomes Containing a Pure, Native, and Oriented Seven-Transmembrane Segment Protein, CCR5" Nature Biotechnology, (2000) 18, pp. 649-654.
Tatemoto et al., "Galanin—A Novel Biologically Active Peptide From Porcine Intestine" FEBS Lett. (1983) 164, pp. 124-128.
Traynor and Nahorski, "Modulation by μ-Opioid Agonists of Guanosine-5'-$O_1$(3-[35S]thio)triphosphate Binding to Membranes from Human Neuroblastoma SH-SY5Y Cells" Mol. Pharmacol., (1985) 47, pp. 848-854.

(56) References Cited

OTHER PUBLICATIONS

Villar et al., "Neuropeptide Gene Expression in Hypothalamic Magnocellular Neurons of Normal and Hypophysectomized Rats: A Combined Immunohistochemical and in situ Hybridization Study" Neurosci. (1990) 36, pp. 181-199.

Wagner et al., "Cre-Mediated Gene Deletion in the Mammary Gland" Nucleic Acids Res., (1997) 25, pp. 4323-4330.

Wang and Gustafson, "Galanin Receptor Subtypes" Drug News Perspect. (1998) 11, pp. 458-468.

Wang et al., "Differential Intracellular Signaling of the GalR1 and GalR2 Galanin Receptor Subtypes" Biochemistry (1998) 37, pp. 6711-6717.

Wang et al., "Cloning and Expressional Characterization of a Novel Galanin Receptor" J. Biol. Chem. (1997) 272, pp. 31949-31953.

Wang et al., "Molecular Cloning and Pharmacological Characterization of a New Galanin Receptor Subtype" Molecular Pharmacology (1997) 52, pp. 337-343.

Waters and Krause, "Distribution of Galanin-1, -2 and -3 Receptor Messenger Rnas in Central and Peripheral Rat Tissues" Neuroscience (2000) 95, pp. 265-271.

Werner and Coveñas, "Classical Neurotransmitters and Neuropeptides Involved in Major Depression: a Review" Int. J. Neurosci. (2010) 120, pp. 455-470.

Wiesenfeld et al., "Galanin-Mediated Control of Pain: Enhanced Role After Nerve Injury" Proc. Natl. Acad. Sci. USA (1992) 89, 3, pp. 334-3337.

Wittau et al., "The Galanin Receptor Type 2 Initiates Multiple Signaling Pathways in Small Cell Lung Cancer Cells by Coupling to $G_q$, $G_1$ and $G_{12}$ Proteins" Oncogene (2000) 19, pp. 4199-4209.

Wu et al., "Systemic Galnon, A Low-Molecular Weight Galanin Receptor Agonist, Reduces Heat Hyperalgesia in Rats With Nerve Injury" Eur. J. Pharmacol. (2003) 482, pp. 133-137.

Zachariou et al., "The Neuropeptide Galanin Modulates Behavioral and Neurochemical Signs of Opiate Withdrawal" Proc. Natl. Acad. Sci. USA (2003) 100, pp. 9028-9033.

Zini et al., "Galanin Reduces Release of Endogenous Excitatory Amino Acids in the Rat Hippocampus" Eur. J. Pharmacol. (1993) 245, pp. 1-7.

International Search Report of PCT/IB2011/054205, mailed Nov. 16, 2011.

Fig. 1 illustrates human GALR2 receptor coding region cDNA (SEQ NO: 1)
ATGAACGTCTCGGGCTGCCCAGGGGCCGGGAACGCGAGCCAGGCGGGCGGCGGG
GGAGGCTGGCACCCCGAGGCGGTCATCGTGCCCCTGCTCTTCGCGCTCATCTTCCT
CGTGGGCACCGTGGGCAACACGCTGGTGCTGGCGGTGCTGCTGCGCGGCGGCCAG
GCGGTCAGCACTACCAACCTGTTCATCCTTAACCTGGGCGTGGCCGACCTGTGTTTC
ATCCTGTGCTGCGTGCCCTTCCAGGCCACCATCTACACCCTGGACGGCTGGGTGTT
CGGCTCGCTGCTGTGCAAGGCGGTGCACTTCCTCATCTTCCTCACCATGCACGCCA
GCAGCTTCACGCTGGCCGCCGTCTCCCTGGACAGGTATCTGGCCATCCGCTACCCG
CTGCACTCCCGCGAGCTGCGCACGCCTCGAAACGCGCTGGCAGCCATCGGGCTCAT
CTGGGGGCTGTCGCTGCTCTTCTCCGGGCCCTACCTGAGCTACTACCGCCAGTCGC
AGCTGGCCAACCTGACCGTGTGCCATCCCGCGTGGAGCGCCCCTCGCCGCCGCGC
CATGGACATCTGCACCTTCGTCTTCAGCTACCTGCTTCCTGTGCTGGTTCTCGGCCT
GACCTACGCGCGCACCTTGCGCTACCTCTGGCGCGCCGTCGACCCGGTGGCCGCG
GGCTCGGGTGCCCGGCGCGCCAAGCGCAAGGTGACACGCATGATCCTCATCGTGG
CCGCGCTCTTCTGCCTCTGCTGGATGCCCCACCACGCGCTCATCCTCTGCGTGTGG
TTCGGCCAGTTCCCGCTCACGCGCGCCACTTATGCGCTTCGCATCCTCTCGCACCTG
GTCTCCTACGCCAACTCCTGCGTCAACCCCATCGTTTACGCGCTGGTCTCCAAGCAC
TTCCGCAAAGGCTTCCGCACGATCTGCGCGGGCCTGCTGGGCCGTGCCCCAGGCC
GAGCCTCGGGCCGTGTGTGCGCTGCCGCGCGGGGCACCCACAGTGGCAGCGTGTT
GGAGCGCGAGTCCAGCGACCTGTTGCACATGAGCGAGGCGGCGGGGGCCCTTCGT
CCCTGCCCCGGCGCTTCCCAGCCATGCATCCTCGAGCCCTGTCCTGGCCCGTCCTG
GCAGGGCCCAAAGGCAGGCGACAGCATCCTGACGGTTGATGTGGCCTGA Fig. 2 illustrates human GALR2 amino acid sequence (SEQ ID NO: 2).
MNVSGCPGAGNASQAGGGGGWHPEAVIVPLLFALIFLVGTVGNTLVLAVLLRGGQAVST
TNLFILNLGVADLCFILCCVPFQATIYTLDGWVFGSLLCKAVHFLIFLTMHASSFTLAAVSL
DRYLAIRYPLHSRELRTPRNALAAIGLIWGLSLLFSGPYLSYYRQSQLANLTVCHPAWSAP
RRRAMDICTFVFSYLLPVLVLGLTYARTLRYLWRAVDPVAAGSGARRAKRKVTRMILIVA
ALFCLCWMPHHALILCVWFGQFPLTRATYALRILSHLVSYANSCVNPIVYALVSKHFRKGF
RTICAGLLGRAPGRASGRVCAAARGTHSGSVLERESSDLLHMSEAAGALRPCPGASQP
CILEPCPGPSWQGPKAGDSILTVDVA Fig. 3 illustrates mouse GALR2 receptor coding region cDNA (SEQ NO: 3).
ATGAATGGCTCGGACAGCCAGGGGGCGGAGGACTCGAGCCAGGAAGGTGGCGGC
GGCTGGCAGCCCGAGGCGGTCCTCGTACCCCTATTTTCGCGCTCATCTTCCTCGTG
GGCGCTGTGGGCAACGCGCTGGTGCTGGCGGTGCTGCTGCGCGGCGGCCAGGCG
GTCAGCACCACGAACCTATTCATCCTCAACCTGGGTGTGGCCGACCTGTGTTTCATC
CTGTGCTGCGTGCCTTTCCAGGCCACCATCTATACCCTGGACGATTGGGTGTTTGGC
TCACTGCTCTGCAAGGCCGTTCATTTCCTCATCTTCCTCACTATGCACGCCAGCAGCT
TCACGCTGGCCGCTGTCTCGCTGGACAGGTATCTGGCCATCCGCTACCCGCTGCAC
TCCCGAGAGTTGCGCACACCTCGAAACGCGCTGGCGGCCATCGGGCTCATCTGGG
GGCTAGCACTGCTCTTCTCCGGGCCCTACCTGAGCTACTACAGTCAGTCGCAGCTG
GCCAATCTGACGGTGTGCCACCCAGCGTGGAGCGCACCACGACGTCGCGCCATGG
ACCTCTGCACTTTTGTCTTTAGCTACCTGTTGCCAGTGCTGGTGCTCAGCCTGACCTA
TGCGCGCACCCTGCACTACCTCTGGCGCACAGTTGACCCAGTAGCTGCAGGCTCAG
GTTCCCAGCGCGCCAAGCGCAAGGTGACACGGATGATCGTCATCGTGGCGGTACTC
TTCTGCCTCTGTTGGATGCCCCACCACGCGCTTATCCTCTGCGTGTGGTTTGGTCGC
TTTCCGCTCACGCGTGCCACTTACGCCCTGCGCATCCTTTCACATCTAGTATCTTATG
CCAACTCGTGTGTCAACCCCATCGTTTATGCTCTGGTCTCCAAGCATTTCCGCAAAG
GTTTCCGCAAAATCTGCGCGGGCCTGCTACGCCGTGCCCCGAGGAGAGCTTCAGGC
CGAGTGTGCATCCTGGCGCCTGGAAACCATAGTGGTGGCATGCTGGAACCTGAGTC
CACAGACCTGACACAGGTGAGCGAGGCAGCCGGGCCCCTCGTCCCCGCACCCGCA
CTTCCCAACTGCACAACCTTGAGTAGAACCCTCGATCCAGCCTGTTAA Fig. 4 illustrates mouse GALR2 amino acid sequence (SEQ ID NO: 4).
MNGSDSQGAEDSSQEGGGGWQPEAVLVPLFFALIFLVGAVGNALVLAVLLRGGQAVST
TNLFILNLGVADLCFILCCVPFQATIYTLDDWVFGSLLCKAVHFLIFLTMHASSFTLAAVSLD
RYLAIRYPLHSRELRTPRNALAAIGLIWGLALLFSGPYLSYYSQSQLANLTVCHPAWSAPR
RRAMDLCTFVFSYLLPVLVLSLTYARTLHYLWRTVDPVAAGSGSQRAKRKVTRMIVIVAV
LFCLCWMPHHALILCVWFGRFPLTRATYALRILSHLVSYANSCVNPIVYALVSKHFRKGFR
KICAGLLRRAPRRASGRVCILAPGNHSGGMLEPESTDLTQVSEAAGPLVPAPALPNCTTL
SRTLDPAC Fig. 5 illustrates rat GALR2 receptor coding region cDNA (SEQ NO: 5).
ATGAATGGCTCCGGCAGCCAGGGCGCGGAGAACACGAGCCAGGAAGGCGGTAGCG
GCGGCTGGCAGCCTGAGGCGGTCCTTGTACCCCTATTTTTCGCGCTCATCTTCCTCG
TGGGCACCGTGGGCAACGCGCTGGTGCTGGCGGTGCTGCTGCGCGGCGGCCAGG
CGGTCAGCACCACCAACCTGTTCATCCTCAACCTGGGCGTGGCCGACCTGTGTTTCA
TCCTGTGCTGCGTGCCTTTCCAGGCCACCATCTACACCCTGGACGACTGGGTGTTCG
GCTCGCTGCTCTGCAAGGCTGTTCATTTCCTCATCTTTCTCACTATGCACGCCAGCA
GCTTCACGCTGGCCGCCGTCTCCCTGGACAGGTATCTGGCCATCCGCTACCCGCTG
CACTCCCGAGAGTTGCGCACACCTCGAAACGCGCTGGCCGCCATCGGGCTCATCTG
GGGGCTAGCACTGCTCTTCTCCGGGCCCTACCTGAGCTACTACCGTCAGTCGCAGC
TGGCCAACCTGACAGTATGCCACCCAGCATGGAGCGCACCTCGACGTCGAGCCATG
GACCTCTGCACCTTCGTCTTTAGCTACCTGCTGCCAGTGCTAGTCCTCAGTCTGACC
TATGCGCGTACCCTGCGCTACCTCTGGCGCACAGTCGACCCGGTGACTGCAGGCTC
AGGTTCCCAGCGCGCCAAACGCAAGGTGACACGGATGATCATCGTGGCGGTGC
TTTTCTGCCTCTGTTGGATGCCCCACCACGCGCTTATCCTCTGCGTGTGGTTTGGTC
GCTTCCCGCTCACGCGTGCCACTTACGCGTTGCGCATCCTTTCACACCTAGTTTCCT
ATGCCAACTCCTGTGTCAACCCCATCGTTTACGCTCTGGTCTCCAAGCATTTCCGTAA
AGGTTTCCGCAAAATCTGCGCGGGCCTGCTGCGCCCTGCCCCGAGGCGAGCTTCG
GGCCGAGTGAGCATCCTGGCGCCTGGGAACCATAGTGGCAGCATGCTGGAACAGG
AATCCACAGACCTGACACAGGTGAGCGAGGCAGCCGGGCCCCTTGTCCCACCACCC
GCACTTCCCAACTGCACAGCCTCGAGTAGAACCCTGGATCCGGCTTGTTAA Fig. 6 illustrates rat GALR2 amino acid sequence (SEQ ID NO: 6).
MNGSGSQGAENTSQEGGSGGWQPEAVLVPLFFALIFLVGTVGNALVLAVLLRGGQAVS
TTNLFILNLGVADLCFILCCVPFQATIYTLDDWVFGSLLCKAVHFLIFLTMHASSFTLAAVSL
DRYLAIRYPLHSRELRTPRNALAAIGLIWGLALLFSGPYLSYYRQSQLANLTVCHPAWSAP
RRRAMDLCTFVFSYLLPVLVLSLTYARTLRYLWRTVDPVTAGSGSQRAKRKVTRMIIVAV
LFCLCWMPHHALILCVWFGRFPLTRATYALRILSHLVSYANSCVNPIVYALVSKHFRKGFR
KICAGLLRPAPRRASGRVSILAPGNHSGSMLEQESTDLTQVSEAAGPLVPPPALPNCTAS
SRTLDPAC Fig. 7 illustrates rhesus macaque GALR2 receptor coding region cDNA (SEQ NO: 7).
ATGAACGTCTCGGTCTGCCCAGGAGCCGGGAACGCGAGCCAGGTGGGCTGCGGGG
GCGGCTGGCACCCCGAGGCGGTCATCGTGCCCCTGCTCTTCGCGCTCATCTTCCTC
GTGGGCACCGTGGGCAACACGCTGGTGCTGGCGGTGCTGCTGCGCGGCGGCCAG
GCGGTCAGCACCACCAACCTGTTCATTCTCAACCTGGGCGTGGCCGACCTGTGTTTC
ATCCTGTGCTGCGTGCCCTTCCAGGCCACCATCTACACGCTGGACGGCTGGGTGTT
CGGCTCGCTGCTGTGCAAGGCTGTGCACTTCCTCATCTTCCTCACCATGCACGCCAG
CAGCTTCACGCTGGCCGCTGTCTCGCTGGACAGGTATCTGGCCATCCGCTACCCGC
TGCACTCCCGCGAACTGCGCACGCCTCGAAACGCGCTGGCAGCGATCGCGCTCATC
TGGGGGCTGTCGCTGCTCTTCTCTGGGCCCTACCTGAGTTACTACCGCCAGTCGCA
GCTGGCCAACCTGACCGTGTGCCATCCCGCGTGGAGCGCCCCTCGCCGCCGCGCC
ATGGACCTCTGCACCTTCGTCTTCAGCTACCTGCTTCCGGTGCTGGTTCTCAGCCTG
ACCTACGCGCGCACCCTGCGCTACCTCTGGCGTGCCGTCGACCCGGTGGCCGCGG
GCTCGGGTGCCCGGCGCGCCAAACGTAAGGTGACACGCATGATCCTTATCGTGGCC
GCGCTCTTCTGCCTCTGCTGGATGCCCCACCACGCGCTCATCCTCTGCGTGTGGTTC
GGCCATTTCCCGCTCACGCGCGCTACTTACGCGCTTCGCATCCTCTCGCACCTGGTC
TCCTACGCCAACTCCTGCGTGAACCCCATCGTTTACGCGCTGGTCTCCAAACACTTC
CGCAAAGGCTTCCGCAAGATCTGCGCGGGCCTGCTGGGCCGTGCCCCACGCCGAG
CCTCGGGCCGCGTGTGCGCTGCCGCGCCGGGCACCCACAGTGGCAGCGTGCTGGA
GCGCGAGTCCACCGACCTGTCGCACGTGAGCGAGGCGGCAGAGGCCCTTCATCCC
TGCCCCGGCGCTTCCCAGCCGTGCACCCTCGAGCCTGGTCCCGGCCCGTCTTGGC
GGGGCCCAAAGGCAGGCAACAGCATCCTGACAGTTGATGTGACCTGA Fig. 8 illustrates rhesus macaque GALR2 amino acid sequence (SEQ ID NO: 8).
MNVSVCPGAGNASQVGCGGGWHPEAVIVPLLFALIFLVGTVGNTLVLAVLLRGGQAVST
TNLFILNLGVADLCFILCCVPFQATIYTLDGWVFGSLLCKAVHFLIFLTMHASSFTLAAVSL
DRYLAIRYPLHSRELRTPRNALAAIALIWGLSLLFSGPYLSYYRQSQLANLTVCHPAWSAP
RRRAMDLCTFVFSYLLPVLVLSLTYARTLRYLWRAVDPVAAGSGARRAKRKVTRMILIVA
ALFCLCWMPHHALILCVWFGHFPLTRATYALRILSHLVSYANSCVNPIVYALVSKHFRKGF
RKICAGLLGRAPRRASGRVCAAAPGTHSGSVLERESTDLSHVSEAAEALHPCPGASQPC
TLEPGPGPSWRGPKAGNSILTVDVT Fig. 9 illustrates chimpanzee GALR2 receptor coding region cDNA (SEQ NO: 9).
ATGAACGTCTCGGGCTGCCCAGGGGCCGGGAACGCGAGCCAGGCGGGCGGCGGG
GGAGGCTGGCACCCCGAGGCGGTCATCGTGCCCCTGCTCTTCGCGCTCATCTTCCT
CGTGGGCATCGTGGGCAACACGCTGGTGCTGGCGGTGCTGCTGCGCGGCGGCCAG
GCGGTCAGCACCACCAACCTGTTCATCCTTAACCTGGGCGTAGCCGACCTGTGTTTC
ATCCTGTGCTGCGTGCCCTTCCAGGCCACCATCTACACCCTGGACGGCTGGGTGTT
CGGCTCGCTGCTGTGCAAGGCGGTGCACTTCTTCATCTTCCTCACCATGCACGCCAG
CAGCTTCACGCTGGCCGCCGTCTCCCTGGACAGGTATCTGGCCATCCGCTACCCGC
TGCACTCCCGCGAGCTGCGCACGCCTCGAAACGCGCTGGCAGCCATCGGGCTCATC
TGGGGGCTGTCGCTGCTCTTCTCCGGGCCCTACCTGAGCTACTACCGCCAGTCGCA
GCTGGCCAACCTGACCGTGTGCCATCCTGCGTGGAGCGCCCCTCGCCGCCGCGCC
ATGGACATCTGCACCTTCGTCTTCAGCTACCTGCTTCCTGTGCTGGTTCTCGGCCTG
ACCTACGCGCGCACCTTGCGCTACCTCTGGCGCGCCGTCGACCCGGTGGCCGCGG
GCTCGGGTGCCCGGCGCGCCAAGCGCAAGGTGACACGCATGATCCTCATCGTGGC
CGCGCTCTTCTGCCTCTGCTGGATGCCCCACCACGCGCTCATCCTCTGCGTGTGGTT
CGGCCATTTCCCGCTCACGCGCGCCACTTATGCGCTTCGCATCCTCTCGCACCTGGT
CTCCTACGCCAACTCCTGCGTCAACCCCATCGTTTACGCGCTGGTCTCCAAGCACTT
CCGCAAAGGCTTCCGCACGATCTGCGCGGGCCTGCTGGGCCGTGCCCCAGGCCGA
GCCTCGGGCCGTGTGTGCGCTGCCGCGCGGGGCACCCACAGTGGCAGCGTGCTGG
AGCGCGAGTCCAGCGACCTGTTGCACATGAGCGAGGCGGCGGGGGCCCTTCGTCC
CTGCCCCGGCGCTTCCCAGCCATGCACCCTCGAGCCCTGTCCTGGCCCGTCCTGGC
AGGGCCCAAAGGCAGGCGACAGCATCCTGACGGTTGATGTGGCCTGA Fig. 10 illustrates chimpanzee GALR2 amino acid sequence (SEQ ID NO: 10).
MNVSGCPGAGNASQAGGGGGWHPEAVIVPLLFALIFLVGIVGNTLVLAVLLRGGQAVST
TNLFILNLGVADLCFILCCVPFQATIYTLDGWVFGSLLCKAVHFFIFLTMHASSFTLAAVSL
DRYLAIRYPLHSRELRTPRNALAAIGLIWGLSLLFSGPYLSYYRQSQLANLTVCHPAWSAP
RRRAMDICTFVFSYLLPVLVLGLTYARTLRYLWRAVDPVAAGSGARRAKRKVTRMILIVA
ALFCLCWMPHHALILCVWFGHFPLTRATYALRILSHLVSYANSCVNPIVYALVSKHFRKGF
RTICAGLLGRAPGRASGRVCAAARGTHSGSVLERESSDLLHMSEAAGALRPCPGASQP
CTLEPCPGPSWQGPKAGDSILTVDVA Fig. 11 illustrates human PreproNeuropeptide Q coding region cDNA (SEQ NO: 11).
ATGAAGGGACTCAGAAGTCTGGCAGCAACAACCTTGGCTCTTTTCCTGGTGTTTGTTT
TCCTGGGAAACTCCAGCTGCGCTCCGCAGAGACTGTTGGAGAGAAGGAACTGGACT
CCTCAAGCTATGCTCTACCTGAAAGGGGCACAGGGTCGCCGCTTCATCTCCGACCA
GAGCCGGAGAAAGGACCTCTCCGACCGGCCACTGCCGGAAAGACGAAGCCCAAAT
CCCCAACTACTAACTATTCCGGAGGCAGCAACCATCTTACTGGCGTCCCTTCAGAAA
TCACCAGAAGATGAAGAAAAAACTTTGATCAAACCAGATTCCTGGAAGACAGTCTG
CTTAACTGGTGA Fig. 12 illustrates human PreproNeuropeptide Q amino acid sequence (SEQ ID NO: 12).
MKGLRSLAATTLALFLVFVFLGNSSCAPQRLLERRNWTPQAMLYLKGAQGRRFISDQSR
RKDLSDRPLPERRSPNPQLLTIPEAATILLASLQKSPEDEEKNFDQTRFLEDSLLN Fig. 13 illustrates human Neuropeptide Q amino acid sequence (SEQ ID NO: 13)
NWTPQAMLYLKGAQ Fig. 14 illustrates human Neuropeptide Q – Glycine amino acid sequence (SEQ ID NO: 14)
NWTPQAMLYLKGAQG Fig. 15 illustrates rat Neuropeptide Q amino acid sequence (SEQ ID NO: 15)
NWTPQAMLYLKGAQGH Fig. 16 illustrates human pro Neuropetide Q (36-58) amino acid sequence (SEQ ID NO: 16)
NWTPQAMLYLKGAQGRRFISDQS Fig. 17 illustrates human pro Neuropetide Q (73-116) amino acid sequence (SEQ ID NO: 17)
SPNPQLLTIPEAATILLASLQKSPEDEEKNFDQTRFLEDSLLNW Fig. 18 illustrates truncated human Neuropeptide Q amino acid sequence (SEQ ID NO: 18)
NWTPQAMLYLKGA Fig. 19 illustrates truncated human Neuropeptide Q amino acid sequence (SEQ ID NO: 19)

NWTPQAMLYLKG

Fig. 20 illustrates truncated human Neuropeptide Q amino acid sequence (SEQ ID NO: 20)

NWTPQAMLYLK

Fig. 21 illustrates truncated human Neuropeptide Q amino acid sequence (SEQ ID NO: 21)

NWTPQAMLYL

Fig. 22 illustrates truncated human Neuropeptide Q – Glycine amino acid sequence (SEQ ID NO: 22)

WTPQAMLYLKGAQG

Fig. 23 illustrates human Neuropeptide Q – Glycine amino acid sequence with substitution by alanine (SEQ ID NO: 23)

AWTPQAMLYLKGAQG

Fig. 24 illustrates human Neuropeptide Q – Glycine amino acid sequence with substitution by alanine (SEQ ID NO: 24)

NWAPQAMLYLKGAQG

Fig. 25 illustrates human Neuropeptide Q – Glycine amino acid sequence with substitution by alanine (SEQ ID NO: 25)

NWTAQAMLYLKGAQG

Fig. 26 illustrates human Neuropeptide Q – Glycine amino acid sequence with substitution by alanine (SEQ ID NO: 26)

NWTPAAMLYLKGAQG

Fig. 27 illustrates human Neuropeptide Q – Glycine amino acid sequence with substitution by alanine (SEQ ID NO: 27)

NWTPQAALYLKGAQG

Fig. 28 illustrates human Neuropeptide Q – Glycine amino acid sequence with substitution by alanine (SEQ ID NO: 28)
NWTPQAMAYLKGAQG Fig. 29 illustrates human Neuropeptide Q – Glycine amino acid sequence with substitution by alanine (SEQ ID NO: 29)
NWTPQAMLYLAGAQG Fig. 30 illustrates human Neuropeptide Q – Glycine amino acid sequence with substitution by alanine (SEQ ID NO: 30)
NWTPQAMLYLKAAQG Fig. 31 illustrates human Neuropeptide Q – Glycine amino acid sequence with substitution by alanine (SEQ ID NO: 31)
NWTPQAMLYLKGAAG Fig. 32 illustrates human Neuropeptide Q – Glycine amino acid sequence with substitution by alanine (SEQ ID NO: 32)
NWTPQAMLYLKGAQA Fig. 33 illustrates human Neuropeptide Q – Glycine amino acid sequence with substitution by proline (SEQ ID NO: 33)
PWTPQAMLYLKGAQG Fig. 34 illustrates human Neuropeptide Q – Glycine amino acid sequence with substitution by proline (SEQ ID NO: 34)
NWPPQAMLYLKGAQG Fig. 35 illustrates human Neuropeptide Q – Glycine amino acid sequence with substitution by proline (SEQ ID NO: 35)
NWTPPAMLYLKGAQG Fig. 36 illustrates human Neuropeptide Q – Glycine amino acid sequence with substitution by proline (SEQ ID NO: 36)
NWTPQPMLYLKGAQG Fig. 37 illustrates human Neuropeptide Q – Glycine amino acid sequence with substitution by proline (SEQ ID NO: 37)
NWTPQAMLYLPGAQG Fig. 38 illustrates human Neuropeptide Q – Glycine amino acid sequence with substitution by proline (SEQ ID NO: 38)
NWTPQAMLYLKPAQG Fig. 39 illustrates human Neuropeptide Q – Glycine amino acid sequence with substitution by proline (SEQ ID NO: 39)
NWTPQAMLYLKGPQG Fig. 40 illustrates human Neuropeptide Q – Glycine amino acid sequence with substitution by proline (SEQ ID NO: 40)
NWTPQAMLYLKGAPG Fig. 41 illustrates human Neuropeptide Q – Glycine amino acid sequence with substitution by proline (SEQ ID NO: 41)
NWTPQAMLYLKGAQP Fig. 42 illustrates the alignment of PreproNeuropeptide Q from different species.

ENSEMBL references for the Prepro Neuropeptide Q with indications of the species (http://www.ensembl.org/) and alignment of amino acids using the CLUSTALW program (http://www.ebi.ac.uk/Tools/clustalw2/index.html).

| | |
|---|---|
| ENSMUSP00000085597 | Mice (Mus musculus) |
| ENSRNOP00000037793 | Rat (Rattus norvegicus |
| ENSTBEP00000005251 | Tree Shrew (Tupaia belangeri) |
| ENSDNOP00000010531 | Armadillo (Dasypus novemcinctus) |
| ENSTSYP00000008473/ | Tarsier (Tarsius syrichta) |
| ENSOGAP00000004255 | Bushbabby (Otolemur garnettii) |
| ENSPPYP00000004974/ | Orangutan (Pongo pygmaeus) |
| ENSGGOP00000010702 | Gorilla (Gorilla gorilla) |
| ENSPTRP00000008125 | Chimpanzee (Pan troglodytes) |
| ENSP00000256969 | Human (Homo sapiens) |
| ENSCJAP00000017381 | Marmoset (Callithrix jacchus) |
| ENSTTRP00000003095 | Dolphin (Tursiops truncates) |
| ENSBTAP00000000491 | Cattle (Bos Taurus) |
| ENSSSCP00000000608 | Pig (Sus scrofa) |
| ENSLAFP00000000808 | Elephant (Loxodonta Africana) |
| ENSPCAP00000002672 | Hyrax (Procavia capensis) |
| ENSETEP00000014897 | Lesser hedgehog tenrec (Echinops telfairi) |
| ENSCHOP00000007296 | Sloth (Choloepus hoffmanni) |
| ENSECAP00000012248 | Horse (Equus caballus) |
| ENSMLUP00000005257 | Microbat (Myotis lucifugus) |
| ENSFCAP00000011716 | Cat (Felis catus) |
| ENSCAFP00000018049 | Dog (Canis familiaris) |
| ENSOCUP00000007598 | Rabbit (Oryctolagus cuniculus) |
| ENSEEUP00000008419 | Hedgehog (Erinaceus europaeus) |
| ENSCPOP00000013193 | Guinea Pig (Cavia porcellus) |
| ENSSTOP00000005692 | Squirrel (Spermophilus tridecemlineatus) |
| ENSOPRP00000005065 | Pika (Ochotona princeps) |
| ENSSARP00000010339 | Shrew (Sorex araneus) |
| ENSPVAP00000002323 | Megabat (Pteropus vampyrus) |
| ENSTGUP00000012483 | Zebra Finch (Taeniopygia guttata) |
| ENSGALP00000021648 | Chichen (Gallus gallus) |
| ENSACAP00000016749 | Anole Lizard (Anolis carolinensis) |
| ENSDARP00000073885 | Zebrafish (Danio rerio) |
| ENSTRUP00000001128 | Fugu (Takifugu rubripes) |

```
ENSMUSP00000085597/1-180    MKGPSVLAVT-AVVLLLVLSALENSSGAPQRLSEKRNWTPQAMLYLKGAQ  49
ENSRNOP00000037793/1-180    MKGPSILAVA-ALALLLVLSVLENSSGAPQRLSEKRNWTPQAMLYLKGAQ  49
ENSTBEP00000005251/1-180    MKGLRRLATI-ALALFLVLSFLGNSKGAPQRLLERRNWTPQAMLYLKGAQ  49
ENSDNOP00000010531/1-180    MKGPRRLPAA-ALALCLVLALLGDAGGAPQRLFERRNWTPQAMLYLKGAX  49
ENSTSYP00000008473/1-180    MMGLRGLAAT-ILALFLVFSFLGSSSSAPQGLFERRNWTPQAMLYLKGAQ  49
ENSOGAP00000004255/1-180    MKGLRSLAAT-TVALFLMFSFLGNSRSAPQGLFERRNWTPQAMLYLKGAQ  49
```

Fig. 42 (Cont'd.)

```
ENSPPYP00000004974/1-180      MKGLRSLAAT-TLALFLVFVFLGNSSCAPQRLLERRNWTPQAMLYLKGAQ  49
ENSGGOP00000010702/1-180      MKGLRSLAAT-TLALFLVFVFLGNSSCAPQRLLERRNWTPQAMLYLKGAQ  49
ENSPTRP00000008125/1-180      MKGLRSLAAT-TLALFLVFVFLGNSSCAPQRLLERRNWTPQAMLYLKGAQ  49
ENSP00000256969/1-180         MKGLRSLAAT-TLALFLVFVFLGNSSCAPQRLLERRNWTPQAMLYLKGAQ  49
ENSCJAP00000017381/1-180      MKGLTSLAAT-TLALFLVVFFLGNSSGTPQRQLERRNWTPQAMLYLKGAQ  49
ENSTTRP00000003095/1-180      MKGFTSLVVT-TLTLFLVFSFMGNSNSAPQRLFERRNWTPQAMLYLKGAQ  49
ENSBTAP00000000491/1-180      MKGFKSLVVM-TLTLFLVFSFMGNCNSAPQRLFERRNWTPQAMLYLKGAQ  49
ENSSSCP00000000608/1-180      --GFRSLVVT-TLALFLVFSFMGHSSSAPQRLFERRNWTPQAMLYLKGAQ  47
ENSLAFP00000000808/1-180      MQGLRNLVAT-TLALFLMFSLMGNSSSAPQRIFERRNWTPQAMLYLKGAQ  49
ENSPCAP00000002672/1-180      MKGLQNLAAT-TLALLLVFSFMENSSSAPQRLFERRNWTPQAMLYLKGAQ  49
ENSETEP00000014897/1-180      --GLASLVAM-ALTLFLVLAFIRDSSSAPQRLLERRNWTPQAMLYLKGAQ  47
ENSCHOP00000007296/1-180      MKGLRSLTAT-TLALFLVFSFMGNFSSARQRLFERRNWTPQAMLYLKGAQ  49
ENSECAP00000012248/1-180      MKGLRSLVAT-TLALFLVFSSMGNSSGAPQRLFERRNWTPQAMLYLKGAQ  49
ENSMLUP00000005257/1-180      MKGFRSLAAT-TLALFLVFSLMGNSSSAPQRLLERRNWTPQAMLYLKGAQ  49
ENSFCAP00000011716/1-180      MKGLRSVVAT-TLALFLVFSFIGNSNSAPQGLFERRNWTPQSMLYLKGAQ  49
ENSCAFP00000018049/1-180      MKGLRSLVAT-TLALFLVFSFLGSSSSAPQGLFERRNWTPQSMLYLKGAQ  49
ENSOCUP00000007598/1-180      VQGLASLTAA-TLAVFLVFSFLGNSSSAPQRLFERRNWTPQAMLYLKGAQ  49
ENSEEUP00000008419/1-180      MKGFRKLAAA-ALALCLVFSFLGNSSSAPQRLFDRRNWTPQAMLYLKGAQ  49
ENSCPOP00000013193/1-180      MKGPSNLAAT-TLALLLVFSVLGDTRGAPQRLLERRNWTPQAMLYLKGAQ  49
ENSSTOP00000005692/1-180      MKGAKSLTAA-TLALLLVFSVLGN--SAPQKLFNKRNWTPQAMLYLKGAQ  47
ENSOPRP00000005065/1-180      MQGLGSLAAM-TLAVFLVCSFPGNSSSVPQXXXXXXXXXXXXXXXXXXXX  49
ENSSARP00000010339/1-180      MKG--RL-AA-TLTLFLLCSLLGHPGVAPQXXXXXXXXXXXXXXXXXXXX  46
ENSPVAP00000002323/1-180      MKXXXXXXXX-XXXXXXXXXXXXXXXXXXXRLFEKRNWTTQAMLYLKGAQ  49
ENSTGUP00000012483/1-180      AQGLHKLPAS-ALALFLAASFIAFSWSAPQAHFQRRNWTPQAMLYLKGAQ  49
ENSGALP00000021648/1-180      AQGLRKLTAS-AMALFLAMSFLSFSRSAPQAHFQRRNWTPQAMLYLKGAQ  49
ENSACAP00000016749/1-180      -------------------------------AHFQRRNWTPQAMLYLKGAQ  20
ENSDARP00000073885/1-180      ----------------------------------------QAMLYLKGTQ  10
ENSTRUP00000001128/1-180      PQHLRSLTLTYLLTLLLFGTFISQSWSAPKGSFQRRNWTPQAMLYLKGTQ  50

ENSMUSP00000085597/1-180      GRRFLSDQSRRKELADR---PPPER-----R-----------------NP  74
ENSRNOP00000037793/1-180      GHRFISDQSRRKELADR---PPPEMNEVVDR-KLLMFKTCIFTWELLTST  95
ENSTBEP00000005251/1-180      GRRFISDQSRRKDLSDR---PPQXX-----X-----------------XX  74
ENSDNOP00000010531/1-180      XXXXXXXXXXXXXXXXX---XXXXR-----R-----------------SS  74
ENSTSYP00000008473/1-180      GRRFISDHSRRKDLADR---PAPERR----------------------SP  74
ENSOGAP00000004255/1-180      G-RFISDQSRRKDLSDR---PLPERR----------------------SP  73
ENSPPYP00000004974/1-180      GRRFISDQSRRKDLSDR---PLPERR----------------------SP  74
ENSGGOP00000010702/1-180      GRRFISDQSRRKDLSDR---PLPERR----------------------SP  74
ENSPTRP00000008125/1-180      GRRFISDQSRRKDLSDR---PLPERR----------------------SP  74
ENSP00000256969/1-180         GRRFISDQSRRKDLSDR---PLPERR----------------------SP  74
ENSCJAP00000017381/1-180      GRRFISDQSRRKDLSDR---PLPERR----------------------SP  74
ENSTTRP00000003095/1-180      GRRFISDQSRRKDLADR---PPPERR----------------------SP  74
ENSBTAP00000000491/1-180      GRRFLSDQSRRKDLSDR---PPLERR----------------------SP  74
ENSSSCP00000000608/1-180      GRRFISNQSRRKDLSDR---PPPERR----------------------SP  72
ENSLAFP00000000808/1-180      GRRFISDQSRRKDLSDRQPLVPPERR----------------------SP  77
ENSPCAP00000002672/1-180      GRRFLSDGSRRKDLPVR---LPLERR----------------------ST  74
ENSETEP00000014897/1-180      GRRFLSDGSRRKDVSER---PPPERR----------------------NP  72
ENSCHOP00000007296/1-180      GRRFISDQSRRKDLSDR---PPPERR----------------------SP  74
```

Fig. 42 (Cont'd.)

| | | |
|---|---|---|
| ENSECAP00000012248/1-180 | GRRFLADQSRRKDLSDR---PPPERR---------------------SP | 74 |
| ENSMLUP00000005257/1-180 | GRRFISDQSRKKELSER---PPPERR---------------------SP | 74 |
| ENSFCAP00000011716/1-180 | GRRFISDQSRKKDLSDR---PPPERR---------------------SP | 74 |
| ENSCAFP00000018049/1-180 | GRRFISDQSRKKDPSDR---PPPERR---------------------SP | 74 |
| ENSOCUP00000007598/1-180 | GRRFISDQSRRKDLSDR---LPPERR---------------------SP | 74 |
| ENSEEUP00000008419/1-180 | GRRFISNQSRRKDLSDR---PPPDRR---------------------SP | 74 |
| ENSCPOP00000013193/1-180 | GRRFLSDQSRRKDLSDR---LPPERR---------------------SP | 74 |
| ENSSTOP00000005692/1-180 | -RRFISDQ-RRKEL---------RR---------------------SP | 63 |
| ENSOPRP00000005065/1-180 | GRRFLSDQSRRKDLSDR---LPPERR---------------------SP | 74 |
| ENSSARP00000010339/1-180 | GRRFLSVQSRGRRLSDL----PPDRR---------------------SP | 70 |
| ENSPVAP00000002323/1-180 | GRRFISDQSRRKDLSDR---PPPERR---------------------SP | 74 |
| ENSTGUP00000012483/1-180 | GRRFIADESQRKDIYDR---VQLETR---------------------SH | 74 |
| ENSGALP00000021648/1-180 | GRRFISDESQRKDLYGR---MQLETR---------------------SQ | 74 |
| ENSACAP00000016749/1-180 | GRRFISEESQRKDLYDR---LQLETR---------------------SQ | 45 |
| ENSDARP00000073885/1-180 | GRRFVSEDRNEGDLYDT---IRLESR---------------------SQ | 35 |
| ENSTRUP00000001128/1-180 | GRRFISEDRKEGDVYDT---LHLETR---------------------SQ | 75 |
| | | |
| ENSMUSP00000085597/1-180 | DLE-LLTLPEAAALFLASL------------------------------ | 92 |
| ENSRNOP00000037793/1-180 | HAHGLAHLCRMSNHFVHNAG----------------------------- | 115 |
| ENSTBEP00000005251/1-180 | XXX-XXXXXXXXXXXXXXX------------------------------ | 92 |
| ENSDNOP00000010531/1-180 | NSQ-PLTLPAAAALLLASW------------------------------ | 92 |
| ENSTSYP00000008473/1-180 | NPQ-LLTLPEAAALLLVSL------------------------------ | 92 |
| ENSOGAP00000004255/1-180 | NPQ-LLTLPETAALLLASL------------------------------ | 91 |
| ENSPPYP00000004974/1-180 | NPR-LLTIPEAATILLASL------------------------------ | 92 |
| ENSGGOP00000010702/1-180 | NPR-LLTIPEAATILLASL------------------------------ | 92 |
| ENSPTRP00000008125/1-180 | NPR-LLTIPEAATILLASL------------------------------ | 92 |
| ENSP00000256969/1-180 | NPQ-LLTIPEAATILLASL------------------------------ | 92 |
| ENSCJAP00000017381/1-180 | NPQ-LLTIPEAAAILLVSR------------------------------ | 92 |
| ENSTTRP00000003095/1-180 | NPQ-LLALPEAAAVLLXXX------------------------------ | 92 |
| ENSBTAP00000000491/1-180 | NSQ-QLTLPEAAAVLLAFL------------------------------ | 92 |
| ENSSSCP00000000608/1-180 | NSQ-LLTLPEAVAVLLASL------------------------------ | 90 |
| ENSLAFP00000000808/1-180 | DPQ-PLTRPEAAALLLASF------------------------------ | 95 |
| ENSPCAP00000002672/1-180 | APQ-PLTLPEAASLLLASF------------------------------ | 92 |
| ENSETEP00000014897/1-180 | DLQ-PRTLPEAAALLLASF------------------------------ | 90 |
| ENSCHOP00000007296/1-180 | YSQ-PLTLPEAAALLLASW------------------------------ | 92 |
| ENSECAP00000012248/1-180 | NSQ-LLTLPEAAALLLASL------------------------------ | 92 |
| ENSMLUP00000005257/1-180 | NAR-LLTLLEAAALLLASL------------------------------ | 92 |
| ENSFCAP00000011716/1-180 | NPQ-LLTLPETAALLLASL------------------------------ | 92 |
| ENSCAFP00000018049/1-180 | NPQ-LLTLPEAAALLLTSL------------------------------ | 92 |
| ENSOCUP00000007598/1-180 | NAQ-LLTLPEAVALLLASL------------------------------ | 92 |
| ENSEEUP00000008419/1-180 | NPQ-QLTLPEAVSLLLTSL------------------------------ | 92 |
| ENSCPOP00000013193/1-180 | NPQ-LLPLPEAALLLALL------------------------------- | 92 |
| ENSSTOP00000005692/1-180 | NPQ-LLTLPEAAALLLALL------------------------------ | 81 |
| ENSOPRP00000005065/1-180 | KAQ-LLT-PPAVAVFLASL------------------------------ | 91 |
| ENSSARP00000010339/1-180 | NPQ-PLTLPEVAALLLASL------------------------------ | 88 |
| ENSPVAP00000002323/1-180 | NPRLLTLPEAAALLLAAL------------------------------- | 93 |
| ENSTGUP00000012483/1-180 | STN-PLSLSEAAALFLTSL------------------------------ | 92 |

Fig. 42 (Cont'd.)

```
ENSGALP00000021648/1-180      NTN-PLSLSEAAALLLSSL------------------------------ 92
ENSACAP00000016749/1-180      NMS-PLTLSEAAALFLSAL------------------------------ 63
ENSDARP00000073885/1-180      NTE-NLSISKAAAFLLNIL------------------------------ 53
ENSTRUP00000001128/1-180      SPE-KLGVEQAASILLNFL------------------------------ 93

ENSMUSP00000085597/1-180      ---------------E-------------KSQKDEGGNFDK-------- 105
ENSRNOP00000037793/1-180      -------QRKEKEG---------------KGQRGRGGETVKL------- 135
ENSTBEP00000005251/1-180      ------------X----------------XXXXXGEGNVDE-------- 105
ENSDNOP00000010531/1-180      ------------Q----------------TPPEDGEENFEQ-------- 105
ENSTSYP00000008473/1-180      ------------Q----------------KPQEDEEENFDQ-------- 105
ENSOGAP00000004255/1-180      ------------Q----------------KPQEDEEENFDQ-------- 104
ENSPPYP00000004974/1-180      ------------Q----------------KSPEDEEKNFDQ-------- 105
ENSGGOP00000010702/1-180      ------------Q----------------KSPEDEEKNFDQ-------- 105
ENSPTRP00000008125/1-180      ------------Q----------------KSPE--------------- 97
ENSP00000256969/1-180         ------------Q----------------KSPEDEEKNFDQ-------- 105
ENSCJAP00000017381/1-180      ------------Q----------------KSPEGEEKNFDQ-------- 105
ENSTTRP00000003095/1-180      ------------X----------------XXXXXGEEN-DQ-------- 104
ENSBTAP00000000491/1-180      ------------Q----------------KPQEAGDENLDQ-------- 105
ENSSSCP00000000608/1-180      ------------K----------------KPQEAGEENFDQ-------- 103
ENSLAFP00000000808/1-180      ------------Q----------------KPQEAEEENFDQ-------- 108
ENSPCAP00000002672/1-180      ------------Q----------------KPQEGEEENFDQ-------- 105
ENSETEP00000014897/1-180      ------------K----------------KPQEVEEENFDQ-------- 103
ENSCHOP00000007296/1-180      ------------Q----------------KPQEAGEENFE--------- 104
ENSECAP00000012248/1-180      ------------Q----------------KLQEAGEENFDQ-------- 105
ENSMLUP00000005257/1-180      ------------Q----------------KPQEAGEENLDP-------- 105
ENSFCAP00000011716/1-180      ------------Q----------------RPQEAGEENFDQ-------- 105
ENSCAFP00000018049/1-180      ------------Q----------------KPQEAREENFDQ-------- 105
ENSOCUP00000007598/1-180      ------------R----------------KPQEDGEENVDQ-------- 105
ENSEEUP00000008419/1-180      ------------Q----------------KPQE--------------- 97
ENSCPOP00000013193/1-180      ------------S----------------KPQEVIIKNTNQK------- 106
ENSSTOP00000005692/1-180      ------------Q----------------KPQEDGEKNSDQ-------- 94
ENSOPRP00000005065/1-180      -------------------------------KPAGDGKEDFLQ-------- 103
ENSSARP00000010339/1-180      ----------------------------Q--------- 89
ENSPVAP00000002323/1-180      ------------Q----------------KPQEAGKEN-DQ-------- 105
ENSTGUP00000012483/1-180      ------------Q----------------KAQEVEEENSEY------- 105
ENSGALP00000021648/1-180      ------------W----------------KAQEVEEENSDH-------- 105
ENSACAP00000016749/1-180      ------------R----------------KAAQEE------------- 70
ENSDARP00000073885/1-180      ------------Q----------------QARDEDEP----------- 62
ENSTRUP00000001128/1-180      ------------Q----------------QARENGE------------ 101

ENSMUSP00000085597/1-180      ---SELLEDRLFN--W------------------------ 116
ENSRNOP00000037793/1-180      ---KEEEEEEEEEEEEEEEEEEEEEEEEE-EEEEEEEAK--T 172
ENSTBEP00000005251/1-180      ---TRFLEGGLLNW-------------------------- 116
ENSDNOP00000010531/1-180      ---TRFLEDNLLNW-------------------------- 116
ENSTSYP00000008473/1-180      ---TRFLENSLLN--W------------------------ 116
ENSOGAP00000004255/1-180      ---TRYLEGSLLN--W------------------------ 115
ENSPPYP00000004974/1-180      ---TRFLEDSLLN--W------------------------ 116
```

Fig. 42 (Cont'd.)

```
ENSGGOP00000010702/1-180      ---TRFLEDSLLN--W------------------------- 116
ENSPTRP00000008125/1-180      ------------------------------------------
ENSP00000256969/1-180         ---TRFLEDSLLN--W------------------------- 116
ENSCJAP00000017381/1-180      ---PRFLEDSLLN--W------------------------- 116
ENSTTRP00000003095/1-180      ---MRF-KDSLLTW-V------------------------- 115
ENSBTAP00000000491/1-180      ---TRFLEDSLLN--W------------------------- 116
ENSSSCP00000000608/1-180      ---TRFLEDSLLNWRK------------------------- 116
ENSLAFP00000000808/1-180      ---TRFLEDSLLK--W------------------------- 119
ENSPCAP00000002672/1-180      ---ARFLEDSLLK--W------------------------- 116
ENSETEP00000014897/1-180      ---TRFLEDSLLT--W------------------------- 114
ENSCHOP00000007296/1-180      ---TRFLEDSLLS--W------------------------- 115
ENSECAP00000012248/1-180      ---TRFLEDSLLN--W------------------------- 116
ENSMLUP00000005257/1-180      ---TRFLDDSLLN--W------------------------- 116
ENSFCAP00000011716/1-180      ---TRILED--LTW-G------------------------- 115
ENSCAFP00000018049/1-180      ---TSVLEDSLLN--W------------------------- 116
ENSOCUP00000007598/1-180      ---ARFLEDSVLY--W------------------------- 116
ENSEEUP00000008419/1-180      ------------------------------------------
ENSCPOP00000013193/1-180      ---NEFLWQWNIN--W------------------------- 117
ENSSTOP00000005692/1-180      ---SRFLGDGLLN--W------------------------- 105
ENSOPRP00000005065/1-180      ---TGFLEDHILN--W------------------------- 114
ENSSARP00000010339/1-180      ----KAQE--------------------------------- 93
ENSPVAP00000002323/1-180      ---TRFLKDNLIN---------------------------- 115
ENSTGUP00000012483/1-180      ---PGYL---------------------------------- 109
ENSGALP00000021648/1-180      ---PGYLMDNLSN--R------------------------- 116
ENSACAP00000016749/1-180      ------------------------------------------
ENSDARP00000073885/1-180      ---------------Y------------------------- 63
ENSTRUP00000001128/1-180      ------------------------------------------
```

Fig. 43 illustrates the effect of Neuropeptide Q polypeptide on the inhibition of the binding of galanin on GALR2.
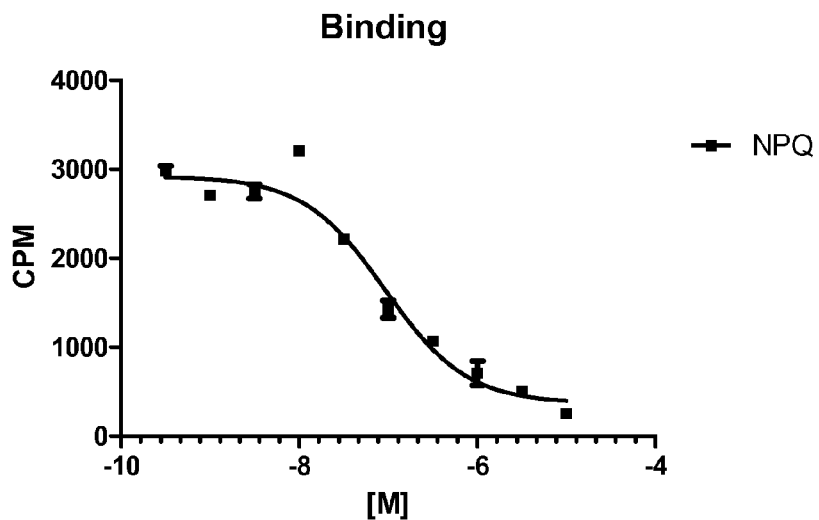
Fig. 44 illustrates the effect of Neuropeptide Q polypeptide on the release of intracellular calcium by GALR2.
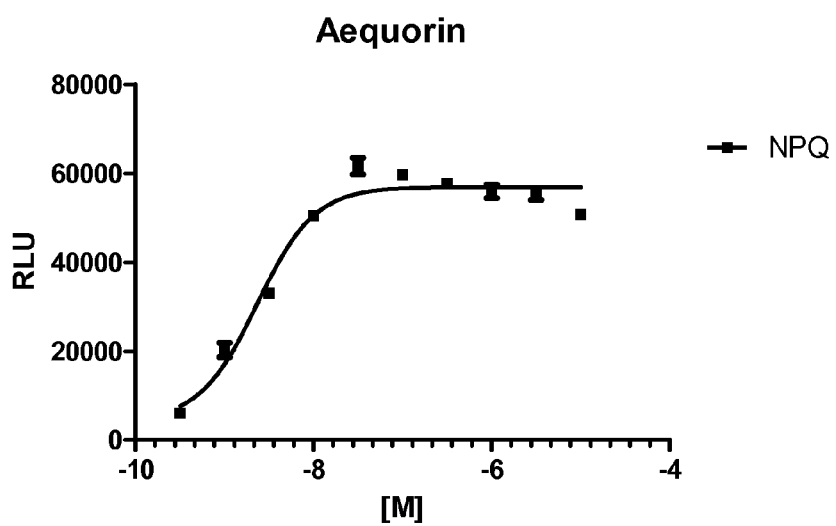

Fig. 45 illustrates the effect of Neuropeptide Q polypeptide on the inhibition of cAMP release by GALR2.
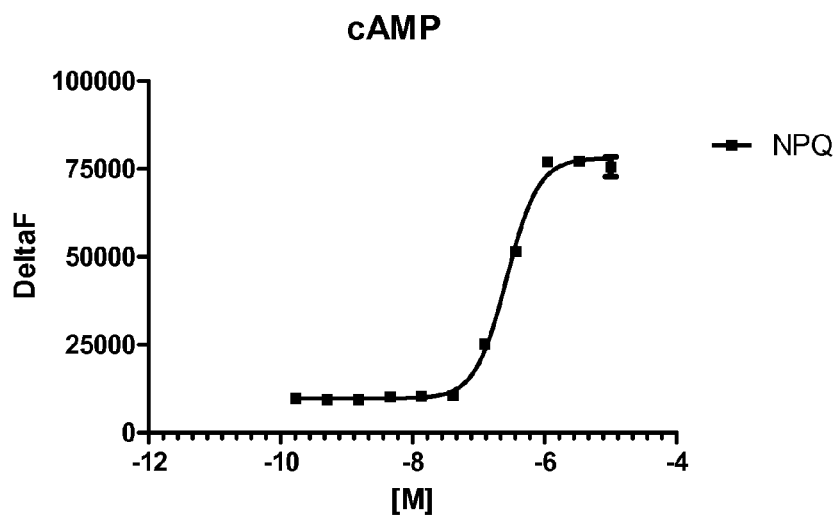
Fig. 46 illustrates the effect of Neuropeptide Q polypeptide on inositol phosphate release by GALR2.
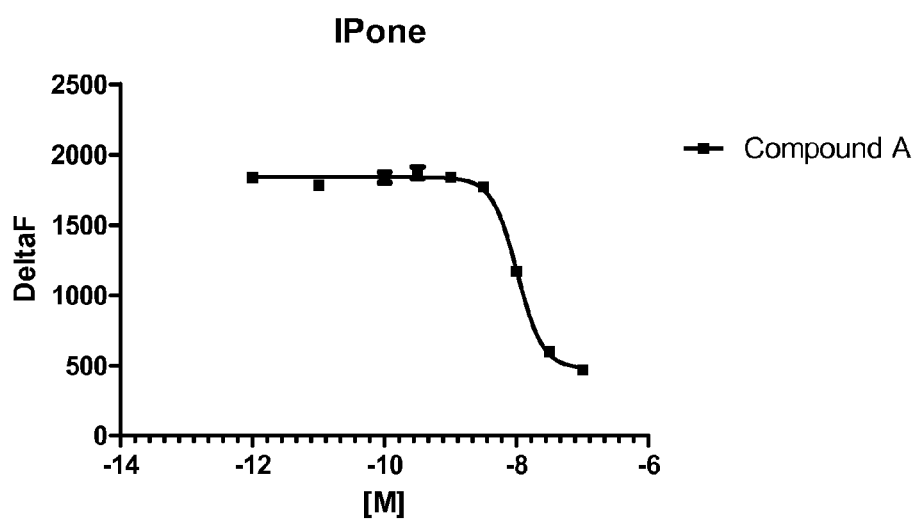

Fig. 47 illustrates the effect of Neuropeptide Q polypeptide on GTP-γ-S binding by GALR2.
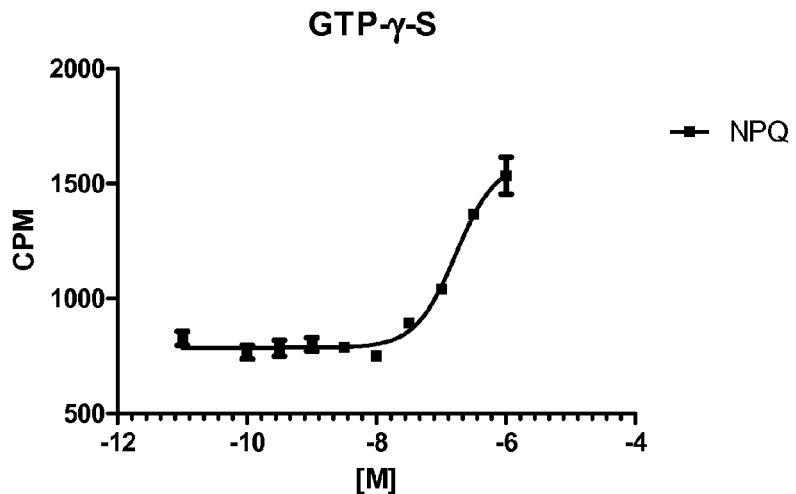
Fig. 48 illustrates the effect of Neuropeptide Q polypeptide on beta-arrestin 2 recruitment by GALR2 using the DiscoveRx technology.
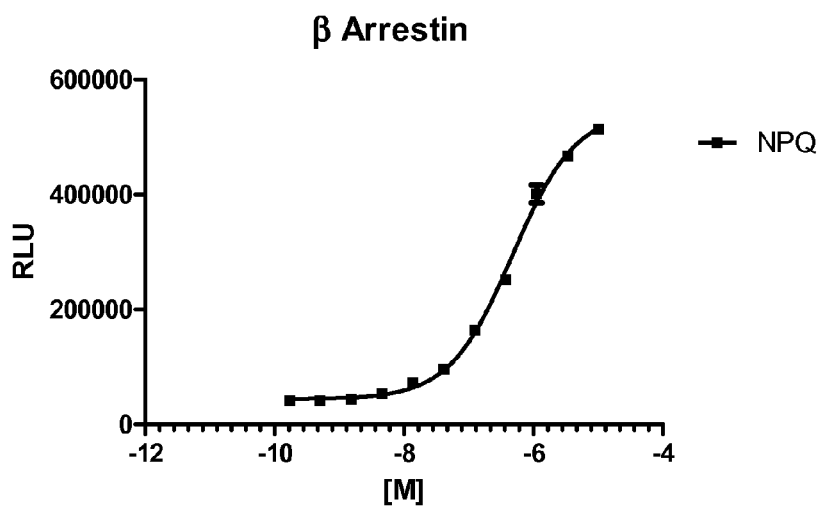

Fig. 49 illustrates the effect of Neuropeptide Q polypeptide on beta-arrestin 2 recruitment by GALR2 using the Tango technology.
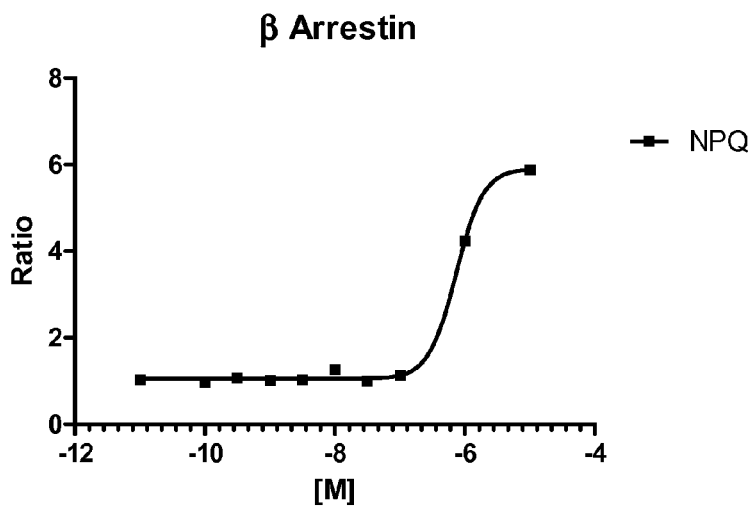
Fig. 50 illustrates the effect of human Neuropeptide Q - Glycine polypeptide, rat Neuropeptide Q polypeptide, human pro Neuropeptide Q (36-58) polypeptide and human pro Neuropeptide Q (73-116) polypeptide on on the release of calcium by GALR2.
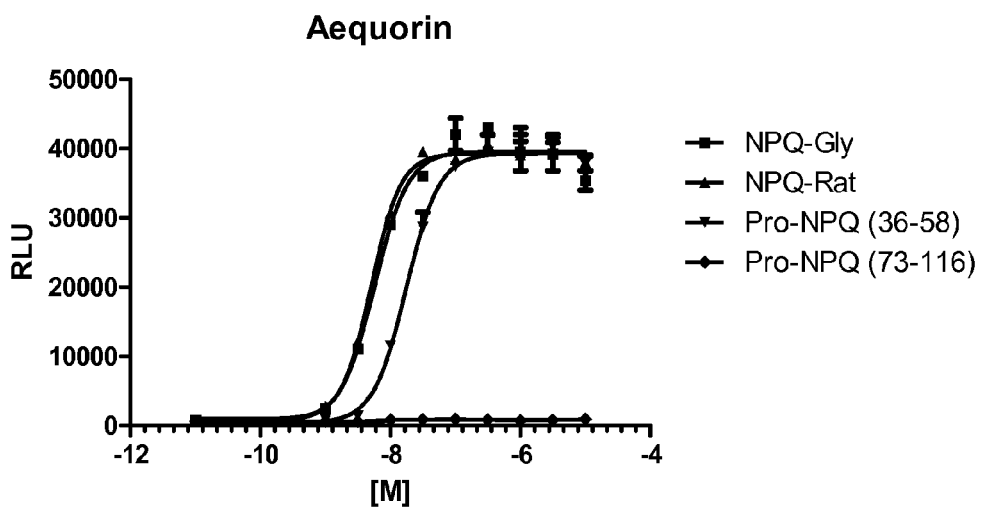

NEUROPEPTIDE Q AS MODULATOR OF GPCR GALR2 AND USES THEREOF

FIELD OF THE INVENTION

The invention relates to the identification of Neuropeptide Q as a new ligand for the G-Protein Coupled Receptor (GPCR) GALR2 and uses thereof.

BACKGROUND OF THE INVENTION

G-protein coupled receptors (GPCRs) are proteins responsible for transducing a signal within a cell. GPCRs have usually seven transmembrane domains. Upon binding of a ligand to a portion or a fragment of a GPCR, a signal is transduced within the cell that results in a change in a biological or physiological property or behavior of the cell. GPCRs, along with G-proteins, effectors (intracellular enzymes and channels modulated by G-proteins) and beta-arrestins, are the components of a modular signaling system that connects the state of intracellular second messengers to extracellular inputs. GPCR genes and gene products can modulate various physiological processes and are potential causative agents of disease. The GPCRs seem to be of critical importance to both the central nervous system and peripheral physiological processes. The GPCR super family is represented by five families: Family I, receptors typified by rhodopsin and the beta2-adrenergic receptor and currently represented by over 200 unique members; Family II, the parathyroid hormone/calcitonin/secretin receptor family; Family III, the metabotropic glutamate receptor family; Family IV, the cAMP receptor family, important in the chemotaxis and development of *D. discoideum*; and Family V, the fungal mating pheromone receptor such as STE2. G proteins represent a family of heterotrimeric proteins composed of alpha, beta and gamma subunits, which bind guanine nucleotides. These proteins are usually linked to cell surface receptors (receptors containing seven transmembrane domains) for signal transduction. Indeed, following ligand binding to the GPCR, a conformational-change is transmitted to the G protein, which causes the alpha-subunit to exchange a bound GDP molecule for a GTP molecule and to dissociate from the beta/gamma-subunits. The GTP-bound form of the alpha, beta/gamma-subunits typically functions as an effector-modulating moiety, leading to the production of second messengers, such as cAMP (e.g. by activation of adenyl cyclase), diacylglycerol or inositol phosphates.

Known and uncharacterized GPCRs currently constitute major targets for drug action and development. There are ongoing efforts to identify new GPCRs which can be used to screen for new agonists and antagonists having potential prophylactic and therapeutical properties. More than 300 GPCRs have been cloned to date, excluding the family of olfactory receptors. Mechanistically, approximately 50-60% of all clinically relevant drugs act by modulating the functions of various GPCRs.

Molecular cloning has revealed the existence of at least three human galanin receptor subtypes (Habert-Ortoli et al., Proc. Natl. Acad. Sci. USA 91: 9780-9783, 1994; Burgevin et al., J. Mol. Neurosci. 6: 33-41, 1995; Howard et al., FEBS Letts. 405: 285-290, 1997; Smith et al., J. Biol. Chem. 272: 24612-24616, 1997; Wang et al., Mol. Pharmacol. 52: 337-343, 1997; Wang et al., J. Biol. Chem. 272: 31949-31953, 1997; Ahmad et al., Ann. N.Y. Acad. Sci. 863: 108-119, 1998; Bloomquist et al., Biophys. Res. Commun. 243: 474-479, 1998; Kolakowski et al., J. Neurochem. 71: 2239-2251, 1998; Smith et al., J. Biol. Chem. 273: 23321-23326, 1998). Galanin Receptor 2, alias GALR2 (SEQ NO: 1 (human polynucleotide sequence, FIG. 1); SEQ ID NO: 2 (human amino acid sequence, FIG. 2); SEQ NO: 3 (mouse polynucleotide sequence, FIG. 3); SEQ ID NO: 4 (mouse amino acid sequence, FIG. 4); SEQ NO: 5 (rat polynucleotide sequence, FIG. 5); SEQ ID NO: 6 (rat amino acid sequence, FIG. 6); SEQ NO: 7 (rhesus macaque polynucleotide sequence, FIG. 7); SEQ ID NO: 8 (rhesus macaque amino acid sequence, FIG. 8); SEQ NO: 9 (chimpanzee polynucleotide sequence, FIG. 9), and SEQ ID NO: 10 (chimpanzee amino acid sequence, FIG. 10)), has been described as a GPCR and represents with Galanin Receptor 1 (GALR1) and Galanin Receptor 3 (GALR3), one of the three Galanin receptors.

GALR2 was isolated from rat hypothalamus extract (Howard et al., FEBS Letts. 405: 285-290, 1997; Smith et al., J. Biol. Chem. 272: 24612-24616, 1997; Wang et al., Mol. Pharmacol. 52: 337-343, 1997). This receptor couples to Gi/Go, Gq/G11 or G12 G-protein types, which means that this subtype of galanin receptors can mediate stimulatory as well as inhibitory effects. The distribution of GALR2 is widespread within the CNS but different from that of GALR1. The dorsal root ganglia (DRG) expresses the highest level of GALR2 in the rat (O'Donnell et al., J. Comp. Neurol. 409: 469-481, 1999; Waters and Krause, Neuroscience 95: 265-271, 2000), while low levels of GALR2 mRNA were detected in the rat locus coeruleus (LC) and in the doral raphe nucleus (DRN) region (O'Donnell et al., J. Comp. Neurol. 409: 469-481, 1999). The mouse GALR2 has been reported in the mouse brain but not in the DRN (Hawes et al., J. Comp. Neurol. 479: 410-423, 2004).

The twenty-nine amino-acid, C-amidated neuropeptide galanin was originally isolated from the porcine gut (Tatemoto et al., FEBS Lett. 164: 124-128, 1983) and is widely expressed in both the central and peripheral nervous system. In Human, galanin is based on thirty amino acids with non amidated C-terminal. It has strong inhibitory actions on synaptic transmission by reducing the number of classical neurotransmitters release (Fisone et al, Proc. Natl. Acad. Sci. USA 84: 7339-7343, 1987; Misane et al., Eur. J. Neurosci. 10: 1230-1240, 1998; Pieribone et al., Neurosci. 64: 861-876, 1995; Hokfelt et al., Ann. N.Y. Acad. Sci. 863: 252-263, 1998; Kinney et al., J. Neurosci. 18: 3489-3500, 1998; Zini et al., Eur. J. Pharmacol. 245: 1-7, 1993). These inhibitory actions result in a diverse range of physiological effects, including working memory impairment (Mastropaolo et al., Proc. Natl. Acad. Sci. USA 85: 9841-9845, 1998), long term potentiation (LTP) impairment (Sakurai et al., Neurosci. Lett. 212: 21-24, 1996) and cAMP response element binding (CREB) phosphorylation (Kinney et al., Neurobiol. Learn. Mem. 92: 429-438, 2009), a reduction in hippocampal excitability with a decreased predisposition to seizure activity (Mazarati et al., Brain Res. 589: 164-166, 1992); and a marked inhibition of nociceptive responses in the intact animal and after nerve injury (Wiesenfeld et al., Proc. Natl. Acad. Sci. USA 89, 3: 334-3337, 1992). These neuromodulatory actions of galanin have long been regarded as the principal role played by the peptide in the nervous system. icv. galanin administration to rodents prior to training impaired performance in a wide range of tasks, including spatial learning and passive avoidance (Crawley, Cell. Mol. Life Sci. 65: 1836-1841, 2008), indicating that galanin has a role in short-term working memory and in long-term associative memory processes.

There is a large body of evidence to indicate that injury to many of neuronal systems markedly induces the expression of galanin at both the mRNA and peptide levels. Examples of such lesion studies include the up-regulation of galanin in the DRG following peripheral nerve axotomy (Hokfelt et al., Neurosci. Lett. 83: 217-220, 1987), in the magnocellular secretory neurons of the hypothalamus after hypophysectomy (Villar et al., Neurosci. 36: 181-199, 1990), in the dorsal raphe (DR) and thalamus after removal of the frontoparietal cortex (Cortes et al., Proc. Natl. Acad. Sci. USA 87: 7742-7746, 1990), in the molecular layer of the hippocampus after an entorhinal cortex lesion (Harrison and Henderson, Neurosci. Lett. 266: 41-44, 1999), and in the medial septum (MS) and vertical limb diagonal-band (vdB) after a fimbria formix bundle transection (Brecht et al., Brain Res. Mol. Brain. Res. 48: 7-16, 1997). These studies have led a number of investigators to speculate that galanin might play a cell survival or growth promoting role in addition to its classical neuromodulatory effects. Galanin level is altered in depressive patients (Werner and Coveñas, Int J Neurosci., 120: 455-70, 2010)

The binding of galanin to GALR1 and GALR3 receptors has been shown to inhibit adenyl cyclase (Wang and Gustafson, Drug News Perspect. 11: 458-68, 1998; Habert-Ortoli et al., Proc. Natl. Acad. Sci. USA. 91: 9780-9783, 1994; Smith, J. Biol. Chem. 273: 23321-23326, 1998) by coupling to the inhibitory Gi and/or Go proteins. In contrast, activation of GALR2 with galanin inhibits the release of cAMP by coupling to Gi and/or Go proteins, stimulates phospholipase C and protein kinase C activity by coupling to Gq, hence activating the extracellular signal-regulated kinases (ERK) cascade, and activates Rho by coupling to G12 proteins (Fathi et al., Brain Res Mol Brain Res. 51: 49-59, 1997; Howard et al., FEBS Lett. 405: 285-290, 1997; Wang et al., Mol Pharmacol. 52: 337-343. 1997; Wittau et al., Oncogene 19: 4199-4209, 2000).

The lack of receptor subtype-specific antisera and the paucity of galanin ligands that are receptor subtype-specific, continues to hamper the analysis of the functional roles played by each receptor.

Activation of GALR2 induces cell arrest and apoptosis in head and neck squamous cell carcinoma (HNSCC) (Kanazawa et al., Expert Opin. Ther. Targets. 14: 289-302, 2010).

WO02/096934 discloses a series of galanin agonist compounds which may be used to treat convulsive seizures such as those taking place in epilepsy. There is mention that such compounds could be used for CNS injuries or in open heart surgery to prevent anoxic damage. Wu et al. published information relating to one of these compounds claimed in WO02/096934, named "galnon" (Wu et al., Eur. J. Pharmacol. 482: 133-137, 2003). Galnon equally activates and has agonistic activity to both GALR1 and GALR2. The use of galnon in studies of epilepsy, opioid addiction and feeding behavior has been discussed by different authors (Saar et al. (Proc. Natl. Acad. Sci. U.S.A. 99: 7136-7141, 2002), Zachariou et al. (Proc. Natl. Acad. Sci. U.S.A. 100: 9028-9033, 2003) and Abramov et al. (Neuropeptides 38: 55-61, 2003)).

It is important to note that receptor selectivity of peptidergic galanin receptor ligands is presently a matter of concern. In vitro studies have indicated that M617 (galanin(1-13)-Gln14-bradykinin(2-9)-amide) exhibits 25-fold subtype specificity for GALR1 vs. GALR2, while M871 (galanin-(2-13)-Glu-His-(Pro)$_3$-(Ala-Leu)$_2$-Ala-amide) binds to the GALR2 with a 32-fold higher affinity than to GALR1 (Mazarati et al., J Pharmacol Exp Ther. 318: 700-708, 2006). Both in vitro and in vivo studies support the view that M617 acts as GALR1 agonist, and M871 as a GALR2 antagonist (Mazarati et al., J Pharmacol Exp Ther. 318: 700-708, 2006). Galanin (2-12), AR-M1896, was first described as a GALR2 selective agonist with a nanomolar affinity (Liu et al, Proc Natl Acad Sci USA. 98: 9960-9964, 2001). However, it was subsequently shown that AR-M1896 bind GALR3 receptors with submicromolar affinity in recombinant CHO and COS-7 cell lines, expressing GALR3 receptors (Lu et al, Neuropeptides. 39: 143-146, 2005). Thus, it is important to take into account the binding of this ligand also to the GALR3 receptor when interpreting functional results. Infusion of AR-M1896 into the DR increased serotonin (5-HT) release in the hippocampus (Mazarati et al, J Neurochem 95: 1495-1503, 2005). Thus, it has been speculated that GALR2 receptors in the DR increase serotonergic neurons firing rates and 5-HT release, an effect congruent with the intracellular signaling cascades coupled to GALR2 (Wang et al., Biochemistry 37: 6711-6717, 1998; Branchek et al, Trends Pharmacol Sci 21: 109-117, 2000; Lu et al, Neuropeptides. 39: 143-146, 2005). Interestingly, chronic administration of fluoxetine, a selective serotonine reuptake inhibitor (SSRI) commonly used as an antidepressant, up-regulated GALR2 but not GALR1 in the DR (Lu et al., Proc Natl Acad Sci USA 102: 874-879, 2005). If GALR2 does indeed enhance serotonergic transmission, as suggested by Lu et al., this action of fluoxetine might be one of the mechanisms of its antidepressant effect. Since the GALR2 subtype mediates galanin excitatory actions on neurotransmitter release (Branchek et al, Trends Pharmacol Sci 21: 109-117, 2000), it seems likely that in-vivo AR-M1896 mainly acts as a GALR2 receptor agonist.

Peptide hormones, or neuropeptides, are amino acids string ranging from approximately 3 to 50 residues. More than 100 small peptides have been discovered during the past 30 years (Hokfelt et al., Lancet Neurol. 2: 463-472, 2003). The first neuropeptide, substance P, was identified by Von Euler and Gaddum in 1931, but its exact chemical structure was not described until 1971 (Chang et al., Nat. New. Biol. 232: 86-87, 1971). They are found within a larger protein (a preprohormone), and the production of the mature hormone usually follows specific rules. Preprohormones are secreted proteins, with a signal sequence necessary for the transport of the protein out of the Golgi complex into a secretory vesicle for processing and secretion where the secretion signal is removed, revealing the prohormone. Neuropeptides are synthesized and released from neurons in the central nervous system (CNS) and peripheral nervous system (PNS) and they almost always coexist with classic neurotransmitters (Hokfelt et al., Nature 284: 525-521, 1980). Neuropeptides can function as neurotransmitters, hormones, and growth factors and their actions are mediated through GPCRs.

In general, hormones are surrounded by basic residues pair, i.e. Arg-Arg, Arg-Lys, Lys-Arg, or Lys-Lys (cleavage sites), which are found directly adjacent to the putative hormone. These double basic residues act as recognition sites for the processing enzymes, usually serine proteases that cleave the prohormone to liberate the active (mature) peptide. In many cases, there is more than a single active peptide within one precursor protein. Another common feature shared by neuropeptides is the presence of an amide group at the C-terminal (instead of the usual carboxylic acid), which provides protection against enzymatic degradation and is required for biological activity. Much evidence indicates that neuropeptides are of particular importance when the nervous system is challenged, e.g. by stress, traumatic events, injury, or drug abuse, modulating the activity of co-expressed neurotransmitters (Hokfelt et al., Lancet Neurol. 2: 463-472, 2003). Binding affinities of neuropeptides are commonly in the nanomolar range, which is thousand-fold or higher than the classical neurotransmitters. Consequently the selectivity of neuropeptide receptors is high, possibly making pharmacological interventions with modulators less prone to side-effects.

These features and the large number of neuropeptides and neuropeptide receptors provide many opportunities for the discovery of new drug targets to treat CNS disorders.

A number of neuropeptides have been identified as potential targets for the antidepressant drugs development. For instance, it has been reported that neurokinin 1 antagonist is as efficient as a SSRI in major depression disorder (Kramer et al., Science 281: 1640-1645, 1998). Other neuropeptides implicated in mood regulation and anxiety are for example neuropeptide Y (NPY), corticotrophin releasing factor (CRF), nociceptin and galanin.

Neuropeptide Q, alias Spexin, is a hormone recently discovered by Mirabeau et al. (Genome Res., 17: 320-327, 2007). The authors developed a Hidden Markov Model (HMM) based on algorithm searches that integrates several peptide hormone sequence features to identify novel peptide hormones. To examine whether the predicted Neuropeptide Q could moderate smooth muscle contractility, a synthetic amidated Neuropeptide Q, NWTPQAMLYLKGAQ-amide, was tested by Mirabeau et al. in stomach explants contractility assay. The Neuropeptide Q dose-dependently induced contraction of stomach muscle with an EC50 of 0.75 µM.

A peptide with a similar sequence has been discovered by Hsueh et al. and named cosmedin B (US20050221359). Cosmedin B interperitoneal treatment suppressed gastric emptying activity in a dose-dependant manner. In an organ contraction assay using rat ileal tissue strips, incubation with cosmedin B produced a concentration dependent muscle contraction. The normalization procedure demonstrated that the magnitude of contraction induced by cosmedin B was comparable to that mediated by the muscarinic receptor stimulated by 5-methyl furmethide.

SUMMARY OF THE INVENTION

The invention relates to the identification of Neuropeptide Q as ligand of the GALR2 receptor, belonging to the GPCR superfamily. The invention encompasses the use of the interaction of GALR2 polypeptides and Neuropeptide Q polypeptides as the basis of screening assays for agents that modulate the activity of the GALR2 receptor. The invention also encompasses diagnostic assays based upon the GALR2/Neuropeptide Q polypeptide interaction, as well as kits for performing diagnostic and screening assays.

Various embodiments of the invention are presented hereafter:

1) The present invention relates to a method of identifying an agent that modulates the function of GALR2, the method comprising: a) contacting a GALR2 polypeptide with a Neuropeptide Q polypeptide in the presence and absence of a candidate modulator under conditions permitting the interaction of the Neuropeptide Q polypeptide to the GALR2 polypeptide; and b) measuring the interaction of the GALR2 polypeptide to the Neuropeptide Q polypeptide, wherein an increase or a decrease in interaction in the presence of the candidate modulator, relative to the interaction in the absence of the candidate modulator, identifies the candidate modulator as an agent that modulates the function of GALR2.

2) A further embodiment of the invention relates to a method of detecting the presence, in a sample, of an agent that modulates the function of GALR2, the method comprising a) contacting a GALR2 polypeptide with a Neuropeptide Q polypeptide in the presence and absence of the sample under conditions permitting the interaction of the Neuropeptide Q polypeptide to the GALR2 polypeptide; and b) measuring the interaction of the GALR2 polypeptide to the Neuropeptide Q polypeptide, wherein an increase or a decrease in interaction in the presence of the sample, relative to the interaction in the absence of the sample, indicates the presence, in the sample of an agent that modulates the function of GALR2.

3) A further embodiment of the invention relates to a method of identifying an agent that modulates the function of GALR2, the method comprising: a) contacting a GALR2 polypeptide with a Neuropeptide Q polypeptide in the presence and absence of a candidate modulator under conditions permitting the interaction of the Neuropeptide Q polypeptide to the GALR2 polypeptide; and b) measuring a signaling activity of the GALR2 polypeptide, wherein a change in the activity in the presence of the candidate modulator relative to the activity in the absence of the candidate modulator identifies the candidate modulator as an agent that modulates the function of GALR2.

4) A further embodiment of the invention relates to a method of detecting the presence, in a sample, of an agent that modulates the function of GALR2, the method comprising: a) contacting a GALR2 polypeptide with a Neuropeptide Q polypeptide in the presence and absence of the sample under conditions permitting the interaction of the Neuropeptide Q polypeptide to the GALR2 polypeptide; b) measuring a signaling activity of the GALR2 polypeptide; and c) comparing the amount of the activity measured in a reaction containing GALR2 and Neuropeptide Q polypeptide without the sample to the amount of the activity measured in a reaction containing GALR2, Neuropeptide Q polypeptide and the sample, wherein a change in the activity in the presence of the sample relative to the activity in the absence of the sample indicates the presence, in the sample, of an agent that modulates the function of GALR2.

5) A further embodiment of the invention relates to a method of identifying an agent that decreases the signaling of a GALR2 polypeptide, said method comprising: a) contacting a GALR2 polypeptide with a Neuropeptide Q polypeptide in the presence and absence of a candidate modulator under conditions permitting the interaction of the Neuropeptide Q polypeptide to the GALR2 polypeptide; b) measuring a signaling activity of the GALR2 polypeptide in the presence and absence of the candidate modulator; and c) comparing the activity measured in the presence of the candidate modulator to the activity measured in the absence of the candidate modulator, wherein a decrease in the activity in the presence of the candidate modulator relative to the activity in the absence of the candidate modulator identifies the candidate modulator as an agent that decreases the signaling of the GALR2 polypeptide.

6) A further embodiment of the invention relates to a method according to any one of embodiments 1) to 5), wherein said agent is an antagonist.

7) A further embodiment of the invention relates to a method of identifying an agent that modulates the function of GALR2, the method comprising: a) contacting a GALR2 polypeptide with a candidate modulator; b) measuring a signaling activity of the GALR2 polypeptide in the presence of the candidate modulator; and c) comparing the activity measured in the presence of the candidate modulator to the activity measured in a sample in which the GALR2 polypeptide is contacted with a Neuropeptide Q polypeptide, wherein the candidate modulator is identified as an agent that modulates the function of GALR2 when the amount of the activity measured in the presence of the candidate modulator is at least 50% of the amount induced by the Neuropeptide Q polypeptide present at its $EC_{50}$.

8) A further embodiment of the invention relates to a method of detecting the presence, in a sample, of an agent that modulates the function of GALR2, the method comprising: a)

contacting a GALR2 polypeptide with the sample; b) measuring a signaling activity of the GALR2 polypeptide in the presence of the sample; and c) comparing the activity measured in the presence of the sample to the activity measured in a reaction in which the GALR2 polypeptide is contacted with a Neuropeptide Q polypeptide, wherein an agent that modulates the function of GALR2 is detected if the amount of the activity measured in the presence of the sample is at least 20% of the amount induced by the Neuropeptide Q polypeptide present at its $EC_{50}$.

9) A further embodiment of the invention relates to a method of identifying an agent that increases the signaling of a GALR2 polypeptide, said method comprising: a) contacting a GALR2 polypeptide with a candidate modulator; b) measuring a signaling activity of the GALR2 polypeptide in the presence of the candidate modulator; and c) comparing the activity measured in the presence of the candidate modulator to the activity measured in a reaction in which the GALR2 polypeptide is contacted with a Neuropeptide Q polypeptide, wherein the candidate modulator is identified as an agent that increases the signaling of GALR2 when the amount of the activity measured in the presence of the candidate modulator is at least 10% of the amount induced by the Neuropeptide Q polypeptide present at its $EC_{50}$.

10) A further embodiment of the invention relates to a method according to any one of embodiments 7) to 9), wherein said Neuropeptide Q polypeptide is present at about its $EC_{50}$ (and preferably at its $EC_{50}$).

11) A further embodiment of the invention relates to a method according to any one of embodiments 7) to 10), wherein said agent is an agonist.

12) A further embodiment of the invention relates to a method according to any one of embodiments 1) to 11), wherein said agent that modulates the function of GALR2 is present in a sample.

13) In a preferred embodiment according to any one of embodiments 1) to 12), the measurement is performed using a method selected from label displacement, surface plasmon resonance, fluorescence resonance energy transfer, fluorescence quenching, and fluorescence polarization (preferably from label displacement, fluorescence resonance energy transfer and fluorescence polarization and more preferably from label displacement and fluorescence resonance energy transfer).

14) A further embodiment of the invention relates to a method according to any one of embodiments 1) to 13), wherein said GALR2 polypeptide sequence is SEQ ID No. 2, and said Neuropeptide Q polypeptide sequence is SEQ ID No. 13, SEQ ID No. 14, or SEQ ID No. 15 (and preferably SEQ ID No. 13), and wherein said Neuropeptide Q polypeptide binds specifically to said GALR2 polypeptide.

15) A further embodiment of the invention relates to a method according to any one of embodiments 1) to 13), wherein said GALR2 polypeptide sequence is selected from the group consisting of SEQ ID No. 2, SEQ ID No. 4, SEQ ID No. 6, SEQ ID No. 8 and SEQ ID No. 10.

16) A further embodiment of the invention relates to a method according to any one of embodiments 1) to 14), wherein said GALR2 polypeptide sequence is SEQ ID No. 2.

17) A further embodiment of the invention relates to a method according to any one of embodiments 1) to 13), wherein said GALR2 polypeptide sequence is SEQ ID No. 4.

18) A further embodiment of the invention relates to a method according to any one of embodiments 1) to 13), wherein said GALR2 polypeptide sequence is SEQ ID No. 6.

19) A further embodiment of the invention relates to a method according to any one of embodiments 1) to 13), wherein said GALR2 polypeptide sequence is SEQ ID No. 8.

20) A further embodiment of the invention relates to a method according to any one of embodiments 1) to 13), wherein said GALR2 polypeptide sequence is SEQ ID No. 10.

21) A further embodiment of the invention relates to a method according to any one of embodiments 1) to 13) or 15) to 20), wherein said Neuropeptide Q polypeptide sequence is selected from the group consisting of SEQ ID No:13, SEQ ID No:14, SEQ ID No:15, SEQ ID No:16, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

22) A further embodiment of the invention relates to a method according to any one of embodiments 1) to 20), wherein said Neuropeptide Q polypeptide sequence is selected from the group consisting of SEQ ID No.13, SEQ ID No.14, SEQ ID No.15, and SEQ ID No.16 (and preferably from SEQ ID No.13 and SEQ ID No. 14 and most preferably SEQ ID No.13).

23) A further embodiment of the invention relates to a method according to any one of embodiments 1) to 13) or 15) to 20), wherein said Neuropeptide Q polypeptide sequence is a fragment of SEQ ID NO. 13 or SEQ ID NO. 14 containing at least 10 amino acids.

24) A further embodiment of the invention relates to a method according to embodiment 23), wherein said Neuropeptide Q polypeptide sequence is selected from SEQ ID NO: 18, SEQ ID NO: 19, SEQ ID NO: 20 and SEQ ID NO: 21 (preferably from SEQ ID NO: 18, SEQ ID NO: 19, and SEQ ID NO: 20).

25) A further embodiment of the invention relates to a method according to embodiment 23), wherein said Neuropeptide Q polypeptide sequence is SEQ ID NO: 22.

26) A further embodiment of the invention relates to a method according to any one of embodiments 1) to 13) or 15) to 20), wherein said Neuropeptide Q polypeptide sequence is a sequence of SEQ ID NO: 14, wherein one amino acid has been substituted by alanine.

27) A further embodiment of the invention relates to a method according to embodiment 26), wherein said Neuropeptide Q polypeptide sequence is selected from SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 and SEQ ID NO: 32, (preferably from SEQ ID NO: 23, SEQ ID NO: 28, and SEQ ID NO: 31).

28) A further embodiment of the invention relates to a method according to any one of embodiments 1) to 13) or 15) to 20), wherein said Neuropeptide Q polypeptide sequence is a sequence of SEQ ID NO: 14, wherein one amino acid has been substituted by proline.

29) A further embodiment of the invention relates to a method according to embodiment 28), wherein said Neuropeptide Q polypeptide sequence is selected from SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41 (preferably from SEQ ID NO: 33, SEQ ID NO: 34, SEQ ID NO: 39, SEQ ID NO: 40, and SEQ ID NO: 41).

30) A further embodiment of the invention relates to a method according to any one of embodiments 1) to 29), wherein said Neuropeptide Q polypeptide binds specifically to said GALR2 polypeptide.

31) A preferred embodiment of the invention relates to a method according to any one of embodiments 1) to 30), wherein the Neuropeptide Q polypeptide is detectably labeled. It is preferred that the Neuropeptide Q polypeptide is detectably labeled with a moiety selected from the group consisting of a radioisotope, a fluorophore, a fluorescence quencher, an enzyme, an affinity tag, and an epitope tag (preferably from the group consisting of a radioisotope, a fluorophore, and an epitope tag, and more preferably from the group consisting of a radioisotope and a fluorophore).

32) A further embodiment of the invention relates to a method according to any one of embodiments 1) to 31), wherein the GALR2 polypeptide is expressed in or on a cell.

33) A further embodiment of the invention relates to a method according to any one of embodiments 1) to 32), wherein the contacting is performed in or on a cell expressing the GALR2 polypeptide.

34) A further embodiment of the invention relates to a method according to any one of embodiments 1) to 31), wherein the GALR2 polypeptide is present in a cell membrane.

35) A further embodiment of the invention relates to a method according to any one of embodiments 32) to 34), wherein said cell is selected from the group consisting of COS-7-cells, a CHO cell, a U2OS cell, a LM (TK-) cell, a NIH-3T3 cell, a HEK cell, a K-562 cell and an 1321N1 astrocytoma cell.

36) A further embodiment of the invention relates to a method according to any one of embodiments 1) to 31), wherein the GALR2 polypeptide is present in or on synthetic liposomes or virus-induced budding membranes (and preferably in or on virus-induced budding membranes).

37) A further embodiment of the invention relates to a method according to any one of embodiments 1) to 31) or 36), wherein the contacting is performed in or on synthetic liposomes (Tajib et al., Nature Biotechnology, 18: 649-654, 2000) or virus-induced budding membranes containing a GALR2 polypeptide.

38) A further embodiment of the invention relates to a method according to any one of embodiments 1) to 37), wherein the method is further performed in the presence of Gα16.

39) A further embodiment of the invention relates to a method according to any one of embodiments 1) to 38), wherein the method is performed using a membrane fraction from cells expressing the GALR2 polypeptide.

40) A further embodiment of the invention relates to a method according to any one of embodiments 1) to 39), wherein the agent is selected from the group consisting of a peptide, a polypeptide, an antibody or antigen-binding fragment thereof, a lipid, a carbohydrate, a nucleic acid, and a small organic molecule, preferably from the group consisting of a peptide, a polypeptide, an antibody or antigen-binding fragment thereof, and a small organic molecule and more preferably from the group consisting of a peptide, a polypeptide, and a small organic molecule. Most preferably the agent is a small organic molecule.

41) A further embodiment of the invention relates to a method according to any one of embodiments 1) to 40), wherein measuring the binding to the GALR2 polypeptide comprises detecting a change in the level of a second messenger.

42) A further embodiment of the invention relates to a method according to any one of embodiments 1) to 40), wherein the step of measuring a signaling activity of the GALR2 polypeptide comprises detecting a change in the level of a second messenger.

43) A further embodiment of the invention relates to a method according to any one of embodiments 1) to 42), wherein the step of measuring a signaling activity comprises measurement of guanine nucleotide binding or exchange, adenyl cyclase activity, cAMP, beta-arrestin 1 recruitment, beta-arrestin 2 recruitment, protein kinase C activity, phosphatidylinositol breakdown, diacylglycerol, inositol triphosphate, intracellular calcium, arachidonic acid, MAP kinase activity, tyrosine kinase activity, or reporter gene expression.

44) In a preferred embodiment, the measuring of a signaling activity according to embodiment 43) comprises using a beta-arrestin-based assay.

45) In another preferred embodiment, the signaling activity measurement according to embodiment 43) comprises using a FLIPR assay or an aequorin-based assay, and preferably an aequorin-based assay.

46) A further embodiment of the invention relates to a method of diagnosing a disease or disorder characterized by dysregulation of GALR2 signaling, the method comprising: a) contacting a tissue sample with an antibody specific for a Neuropeptide Q polypeptide; b) detecting binding of the antibody to the tissue sample; and c) comparing the binding detected in step (b) with a standard, wherein a difference in binding relative to the standard is diagnostic of a disease or disorder characterized by dysregulation of GALR2.

47) A further embodiment of the invention relates to a method of diagnosing a disease or disorder characterized by dysregulation of GALR2 signaling, the method comprising: a) contacting a tissue sample with an antibody specific for a GALR2 polypeptide and an antibody specific for a Neuropeptide Q polypeptide; b) detecting binding of the antibodies to the tissue sample; and c) comparing the binding detected in step (b) with a standard, wherein a difference in the binding of either antibody or both, relative to the standard, is diagnostic of a disease or disorder characterized by dysregulation of GALR2.

48) A further embodiment of the invention relates to a method of diagnosing a disease or disorder characterized by dysregulation of GALR2 signaling, the method comprising: a) isolating nucleic acid from a tissue sample; b) amplifying a Neuropeptide Q polynucleotide, using the nucleic acid as a template; and c) comparing the amount of amplified Neuropeptide Q polynucleotide produced in step (b) with a standard, wherein a difference in the amount of amplified Neuropeptide Q polynucleotide relative to the standard is diagnostic of a disease or disorder characterized by dysregulation of GALR2. In a preferred embodiment, the step of amplifying comprises RT/PCR. In another preferred embodiment, the step of comparing the amount is performed in microarray experiments.

49) A further embodiment of the invention relates to a method of diagnosing a disease or disorder characterized by dysregulation of GALR2 signaling, the method comprising: a) isolating nucleic acid from a tissue sample; b) amplifying a Neuropeptide Q polynucleotide, using the nucleic acid as a template; and c) comparing the sequence of the amplified Neuropeptide Q polynucleotide produced in step (b) with a standard, wherein a difference in the sequence, relative to the standard is diagnostic of a disease or disorder characterized by dysregulation of GALR2. In a preferred embodiment, the step of amplifying comprises RT/PCR. In another preferred embodiment, the standard is SEQ ID NO: 11. In another preferred embodiment, the step of comparing the sequence comprises minisequencing. In another preferred embodiment, the step of comparing the sequence is performed in microarray experiments.

50) A further embodiment of the invention relates to a composition comprising an isolated GALR2 polypeptide and an isolated Neuropeptide Q polypeptide.

51) A further embodiment of the invention relates to a kit for screening for agents that modulate GALR2 signaling, or for the diagnosis of a disease or disorder characterized by dysregulation of a GALR2 polypeptide (and notably to a kit for screening for agents that modulate GALR2 signaling), the kit comprising an isolated GALR2 polypeptide and packaging materials therefore. In a preferred embodiment, the kit further comprises a Neuropeptide Q polypeptide.

Diagnostic kits according to the invention permit the determination of whether, for example, a tissue sample or an extract prepared from a tissue sample has an elevated level or activity of Neuropeptide Q or GALR2. The kits may also permit the identification of mutations in genes encoding GALR2 or Neuropeptide Q polypeptide and detection of an abnormal level of nucleic acids encoding GALR2 or Neuropeptide Q polypeptide.

Neuropeptide Q or GALR2 have an "elevated level" if the level is increased by 10% or more in a tissue sample or an extract prepared from a tissue sample in comparison to level generally observed from a similar tissue sample or from an extract prepared from a similar tissue sample.

Nucleic acids encoding GALR2 or Neuropeptide Q polypeptide have "abnormal level" if the level is increased or decreased by 10% or more in comparison to a level generally observed.

52) A further embodiment of the invention relates to a kit for screening for agents that modulate GALR2 signaling, or for the diagnosis of a disease or disorder characterized by dysregulation of a GALR2 polypeptide (and notably to a kit for screening for agents that modulate GALR2 signaling), the kit comprising an isolated polynucleotide encoding a GALR2 polypeptide and packaging materials therefore. In a preferred embodiment, the kit further comprises an isolated polynucleotide encoding a Neuropeptide Q polypeptide.

53) A further embodiment of the invention relates to a kit for screening for agents that modulate GALR2 signaling, or for the diagnosis of a disease or disorder characterized by dysregulation of a GALR2 polypeptide (and notably to a kit for screening for agents that modulate GALR2 signaling), the kit comprising a cell transformed with a polynucleotide encoding a GALR2 polypeptide and packaging materials therefore. In a preferred embodiment, the kit further comprises an isolated polynucleotide encoding a Neuropeptide Q polypeptide or a cell comprising a polynucleotide encoding a Neuropeptide Q polypeptide.

As used herein, the term "GALR2 polypeptide" refers to a polypeptide having two essential properties: 1) a GALR2 polypeptide has at least 70% amino acid identity, and preferably at least 80%, more preferably at least 90%, most preferably at least 95% and notably 100% amino acid identity, to SEQ ID NO: 2, SEQ ID NO: 4, SEQ ID NO: 6, SEQ ID NO: 8 or SEQ ID NO: 10 (and notably to SEQ ID NO: 2); and 2) a GALR2 polypeptide has GALR2 activity, i.e., the polypeptide responds to a Neuropeptide Q polypeptide or a functional fragment thereof. Optimally, a "GALR2 polypeptide" also has GALR2 signaling activity as defined herein.

As used herein, the term "GALR2 polynucleotide" refers to a polynucleotide that encodes a GALR2 polypeptide as defined herein.

As used herein, the term "GALR2 activity" refers to specific binding of a Neuropeptide Q polypeptide or a functional fragment thereof by a GALR2 polypeptide.

As used herein, the term "GALR2 signaling activity" refers to the initiation or propagation of signaling by a GALR2 polypeptide. GALR2 signaling activity is monitored by measuring a detectable step in a signaling cascade by assaying one or more of the following: stimulation of GDP for GTP exchange on a G protein; recruitment of beta-arrestin1; recruitment of beta-arrestin 2; alteration of adenyl cyclase activity; protein kinase C modulation; phosphatidylinositol breakdown (generating second messengers diacylglycerol, and inositol triphosphate); intracellular calcium flux; activation of MAP kinases; modulation of tyrosine kinases; gene modulation or reporter gene activity. A detectable step in a signaling cascade is considered initiated or propagated if the measurable activity is altered by 10% or more above or below a baseline established in the substantial absence of a Neuropeptide Q polypeptide relative to any of the GALR2 activity assays described herein below. The measurable activity can be measured directly, as in, for example, beta-arrestin recruitment measurement. Alternatively, the measurable activity can be quantified indirectly (for example, by reporter gene assay).

As used herein, the term "detectable step" refers to a step that can be measured, either directly, e.g., by measurement of a second messenger or detection of a modified (e.g, phosphorylated) protein, or indirectly, e.g., by monitoring a downstream effect of that step. For example, adenyl cyclase activation results in the generation of cAMP. The activity of adenyl cyclase can be measured directly, e.g., by an assay that monitors the production of cAMP in the assay, or indirectly, by measurement of actual levels of cAMP.

As used herein, the term "isolated" refers to a population of molecules, e.g., polypeptides or polynucleotides, the composition of which contains less than 50% (by weight), preferably less than 40%, more preferably less than 20% and most preferably 2% or less, contaminating molecules of an unlike nature. When the term "isolated" is applied to a GALR2 polypeptide, it is specifically meant to also encompass a GALR2 polypeptide that is associated with a lipid membrane or embedded in a lipid membrane.

As used herein, the term "Neuropeptide Q polypeptide" refers to a polypeptide having at least 31% identity, and preferably at least 50%, more preferably at least 75%, most preferably at least 95% and notably 100% identity, to a polypeptide represented by SEQ ID NO. 13, SEQ ID NO. 14, SEQ ID NO. 15, or SEQ ID NO. 16 (notably to the polypeptide represented by SEQ ID NO. 13) that specifically binds to and/or activates a signaling activity of a GALR2 polypeptide having the sequence of SEQ ID NO: 2. "Neuropeptide Q polypeptide" may also refer to a fragment of a polypeptide meeting the preceding definition, wherein the fragment retains at least 10% (preferably at least 50%) of the binding activity and/or level of signaling activation of the full length polypeptide of SEQ ID NO: 13. A Neuropeptide Q polypeptide can comprise additions, insertions, deletions or substitutions relative to SEQ ID NO: 13, SEQ ID NO: 14, SEQ ID NO: 15, or SEQ ID NO: 16 (notably to SEQ ID NO: 13), as long as the resulting polypeptide retains at least 10% (preferably at least 50%) of the binding activity and/or level of signaling activation of the full length polypeptide represented by SEQ ID NO: 13. Examples of fragments of Neuropeptide Q polypeptides relative to SEQ ID NO. 14 are polypeptides of SEQ ID NO: 18, SEQ ID NO: 19, SEQ ID NO: 20, SEQ ID NO: 21 and SEQ ID NO: 22. Examples of Neuropeptide Q polypeptides comprising substitutions relative to SEQ ID NO. 14 are polypeptides of SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

The term "specifically binds" means that the Neuropeptide Q polypeptide has an $EC_{50}$, or a Kd of 500 nM or less.

In addition to the sequences necessary for binding to GALR2 and/or activating a GALR2 signaling activity, a Neuropeptide Q polypeptide, including a truncated Neuropeptide Q polypeptide can comprise additional sequences, as in for example, a Neuropeptide Q polypeptide fusion protein. Non-limiting examples of fusion partners include glutathione-S-transferase (GST), maltose binding protein, alkaline phosphatase, thioredoxin, green fluorescent protein (GFP), histidine tags (e.g., 6× or greater His), or epitope tags (e.g., HA-tag, Myc tag, FLAG tag).

As used herein, the term "Neuropeptide Q polynucleotide" refers to a polynucleotide that encodes a Neuropeptide Q polypeptide as defined herein, or the complement thereof. A "Neuropeptide Q polynucleotide" may be a polynucleotide sequence which encodes truncated or modified Neuropeptide Q.

The present invention also relates to an agent identified or detected by a method as described above. In addition, the present invention relates to a composition comprising said agent.

The invention further contemplates the use of an agent or a composition according to the present invention, for the preparation of a medicament for the prevention or treatment of a GALR2-related disease or a GALR2-related disorder.

Wherein said GALR2-related disease or GALR2-related disorder is chosen from the group consisting of Central Nervous System (CNS) Disorders. CNS disorders include disorders of the central nervous system as well as disorders of the peripheral nervous system. CNS disorders include, but are not limited to brain injuries, cerebrovascular diseases and their consequences, Parkinson's disease, corticobasal degeneration, motor neuron disease, dementia, including amyotrophic lateral sclerosis (ALS), multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalami degeneration, Creutzfeld-Jakob dementia, HIV dementia, schizophrenia with dementia, and Korsakoffs psychosis are also considered to be CNS disorders. Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be CNS disorders. Pain, within the meaning of this definition, is also considered to be a CNS disorder. Pain can be associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneo-plastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with peripheral nerve damage, central pain (i.e. due to cerebral ischemia) and various chronic pain i.e., lumbago, back pain (low back pain), inflammatory and/or rheumatic pain. Headache pain (for example, migraine with aura, migraine without aura, and other migraine disorders), episodic and chronic tension-type headache, tension-type like headache, cluster headache, and chronic paroxysmal hemicrania are also CNS disorders. Visceral pain such as pancreatits, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome and protatodynia are also CNS disorders. Also considered to be a disorder of the nervous system are acute pain, for example postoperative pain, and pain after trauma.

Wherein said GALR2-related disease or GALR2-related disorder is further chosen from the group consisting of neurological and psychiatric disorders associated with GALR2 dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as, for example, opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

Wherein said GALR2-related disease or GALR2-related disorder is further chosen from the group consisting of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the anxiety disorder is selected from the group of agoraphobia, generalized anxiety disorder (GAD), obsessive-compulsive disorder (OCD), panic disorder, posttraumatic stress disorder (PTSD), social phobia and other phobias.

Preferably, the psychotic disorder is selected from the group of schizophrenia, delusional disorder, schizoaffective disorder, schizophreniform disorder and substance-induced psychotic disorder.

Preferably, the personality disorder is selected from the group of obsessive-compulsive personality disorder and schizoid, schizotypal disorder.

Preferably, the substance-related disorder is selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the eating disorder is selected from the group of anorexia nervosa and bulimia nervosa.

Preferably, the mood disorder is selected from the group of bipolar disorders (I & II), cyclothymic disorder, depression, dysthymic disorder, major depressive disorder and substance-induced mood disorder.

Wherein said GALR2-related disease or GALR2-related disorder is further chosen from the group consisting of migraine.

Wherein said GALR2-related disease or GALR2-related disorder is further chosen from the group consisting of epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Wherein said GALR2-related disease or GALR2-related disorder is further chosen from the group consisting of attention-deficit/hyperactivity disorder.

Wherein said GALR2-related disease or GALR2-related disorder is further chosen from the group consisting of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment. Of the disorders mentioned above, the treatment of anxiety, schizophrenia, migraine, depression, and epilepsy are of particular importance.

Wherein said GALR2-related disease or GALR2-related disorder is further chosen from the group consisting of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Wherein said GALR2-related disease or GALR2-related disorder is further chosen from the group consisting of neuroinflammation.

Neuroinflammation refers to cell signaling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Wherein said GALR2-related disease or GALR2-related disorder is further chosen from the group consisting of Cancer, Tumor metastasis, Ovary and uterus tumors.

The invention further contemplates the use of an agent or a composition according to the present invention, for the preparation of a medicament for the prevention or treatment of a Neuropeptide Q polypeptide-related disease or a Neuropeptide Q polypeptide-related disorder.

Wherein said Neuropeptide Q-related disease or Neuropeptide Q-related disorder is chosen from the group consisting of Central Nervous System (CNS) Disorders. CNS disorders include disorders of the central nervous system as well as disorders of the peripheral nervous system. CNS disorders include, but are not limited to brain injuries, cerebrovascular diseases and their consequences, Parkinson's disease, corticobasal degeneration, motor neuron disease, dementia, including amyotrophic lateral sclerosis (ALS), multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalami degeneration, Creutzfeld-Jakob dementia, HIV dementia, schizophrenia with dementia, and Korsakoffs psychosis are also considered to be CNS disorders. Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be CNS disorders. Pain, within the meaning of this definition, is also considered to be a CNS disorder. Pain can be associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneo-plastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with peripheral nerve damage, central pain (i.e. due to cerebral ischemia) and various chronic pain i.e., lumbago, back pain (low back pain), inflammatory and/or rheumatic pain. Headache pain (for example, migraine with aura, migraine without aura, and other migraine disorders), episodic and chronic tension-type headache, tension-type like headache, cluster headache, and chronic paroxysmal hemicrania are also CNS disorders. Visceral pain such as pancreatits, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome and protatodynia are also CNS disorders. Also considered to be a disorder of the nervous system are acute pain, for example postoperative pain, and pain after trauma.

Wherein said Neuropeptide Q-related disease or Neuropeptide Q-related disorder is further chosen from the group consisting of neurological and psychiatric disorders associated with Neuropeptide Q dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as, for example, opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

Wherein said Neuropeptide Q-related disease or Neuropeptide Q-related disorder is further chosen from the group consisting of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the anxiety disorder is selected from the group of agoraphobia, generalized anxiety disorder (GAD), obsessive-compulsive disorder (OCD), panic disorder, posttraumatic stress disorder (PTSD), social phobia and other phobias.

Preferably, the psychotic disorder is selected from the group of schizophrenia, delusional disorder, schizoaffective disorder, schizophreniform disorder and substance-induced psychotic disorder.

Preferably, the personality disorder is selected from the group of obsessive-compulsive personality disorder and schizoid, schizotypal disorder.

Preferably, the substance-related disorder is selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the eating disorder is selected from the group of anorexia nervosa and bulimia nervosa.

Preferably, the mood disorder is selected from the group of bipolar disorders (I & II), cyclothymic disorder, depression, dysthymic disorder, major depressive disorder and substance-induced mood disorder.

Wherein said Neuropeptide Q-related disease or Neuropeptide Q-related disorder is further chosen from the group consisting of migraine.

Wherein said Neuropeptide Q-related disease or Neuropeptide Q-related disorder is further chosen from the group consisting of epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Wherein said Neuropeptide Q-related disease or Neuropeptide Q-related disorder is further chosen from the group consisting of attention-deficit/hyperactivity disorder.

Wherein said Neuropeptide Q-related disease or Neuropeptide Q-related disorder is further chosen from the group consisting of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment. Of the disorders mentioned above, the treatment of anxiety, schizophrenia, migraine, depression, and epilepsy are of particular importance.

Wherein said Neuropeptide Q-related disease or Neuropeptide Q-related disorder is further chosen from the group consisting of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Wherein said Neuropeptide Q-related disease or Neuropeptide Q-related disorder is further chosen from the group consisting of neuroinflammation.

Neuroinflammation refers to cell signaling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Wherein said Neuropeptide Q-related disease or Neuropeptide Q-related disorder is further chosen from the group consisting of Cancer, Tumor metastasis, Ovary and uterus tumors.

The invention also relates to the use of a truncated and/or modified Neuropeptide Q polypeptide according to the present invention or a full length Neuropeptide Q polypeptide for the production of a medicament.

Said medicament may be applied for the treatment of a GALR2-related disease or a GALR2-related disorder; wherein said GALR2-related disease or GALR2-related disorder is preferentially chosen from the groups as defined above.

Said medicament may also be applied for the treatment of a Neuropeptide Q polypeptide-related disease or a Neuropeptide Q polypeptide-related disorder; wherein said Neuropeptide Q polypeptide-related disease or Neuropeptide Q polypeptide-related disorder is preferentially chosen from the groups as defined above.

As used herein, the terms "candidate compound" and "candidate modulator" refer to a compound or a composition being evaluated for the ability to modulate ligand binding to a GALR2 polypeptide or the ability to modulate an activity of a GALR2 polypeptide. Candidate modulators can be natural or synthetic compounds, including, for example, small molecules, compounds contained in extracts of animal, plant, bacterial or fungal cells, as well as conditioned medium from such cells. Preferably candidate modulators can be natural or synthetic compounds and especially small organic molecules.

As used herein, the term "small molecule" refers to a compound having molecular mass of less than 3000 Daltons, preferably less than 1500, still more preferably less than 1000, and most preferably less than 600 Daltons. A "small organic molecule" is a small molecule that comprises carbon.

As used herein, the term "change in binding" or "change in activity" and the equivalent terms "difference in binding" or "difference in activity" refer to an at least 10% increase or decrease in binding, or signaling activity in a given assay.

As used herein, the term "conditions permitting the binding of Neuropeptide Q polypeptide to GALR2" refers to conditions of, for example, temperature, salt concentration, pH and protein concentration under which Neuropeptide Q polypeptide binds GALR2. Exact binding conditions will vary depending upon the nature of the assay, for example, whether the assay uses viable cells, only membrane fraction of cells, or only protein fraction of cells.

As used herein, the term "conditions permitting the interaction of the Neuropeptide Q polypeptide to the GALR2 polypeptide" refers to conditions of, for example, temperature, salt concentration, pH and protein concentration under which Neuropeptide Q polypeptide binds GALR2. Exact binding conditions will vary depending upon the nature of the assay, for example, whether the assay uses viable cells, only membrane fraction of cells, or only protein fraction of cells.

As used herein, the term "sample" refers to the source of molecules being tested for the presence of an agent that modulates binding to or signaling activity of a GALR2 polypeptide.

A sample can be an environmental sample, a natural extract of animal, plant yeast or bacterial cells or tissues, a clinical sample, a synthetic sample, or a conditioned medium from recombinant cells or a fermentation process. The term "tissue sample" refers to a tissue that is tested for the presence, abundance, quality or an activity of a GALR2 polypeptide, a Neuropeptide Q polypeptide, a nucleic acid encoding a GALR2 or Neuropeptide Q polypeptide, or an agent that modifies the ligand binding and/or activity of a GALR2 polypeptide.

As used herein, a "tissue" is an aggregate of cells that perform a particular function in an organism. The term "tissue" as used herein refers to cellular material from a particular physiological region. The cells in a particular tissue can comprise several different cell types. A non-limiting example of this would be brain tissue that further comprises neurons and glial cells, as well as capillary endothelial cells and blood cells, all contained in a given tissue section or sample. In addition to solid tissues, the term "tissue" is also intended to encompass non-solid tissues, such as blood.

As used herein, the term "membrane fraction" refers to a preparation of cellular lipid membranes comprising a GALR2 polypeptide. As the term is used herein, membrane fraction is distinct from a cellular homogenate, in that at least a portion (i.e., at least 10%, preferably at least 30%, more preferably at least 60% and most preferably at least 90%) of non-membrane-associated cellular constituents has been removed. The term "membrane associated" refers to those cellular constituents that are either integrated into a lipid membrane or are physically associated with a component that is integrated into a lipid membrane.

As used herein, the term "second messenger" refers to a molecule, generated or caused to vary in concentration by the activation of a G-Protein Coupled Receptor, which participates in the transduction of a signal from that GPCR. Non-limiting examples of second messengers include cAMP, diacylglycerol, inositol triphosphate and intracellular calcium. The term "change in the level of a second messenger" refers to an increase or decrease of at least 10% in the detected level of a given second messenger relative to the amount detected in an assay performed in the absence of a candidate modulator.

As used herein, the term "aequorin-based assay" refers to an assay for GPCR activity that measures intracellular calcium flux induced by activated GPCRs, wherein intracellular calcium flux is measured by the luminescence of aequorin expressed in the cell.

As used herein, the term "binding" refers to the physical association of a ligand (e.g., a Neuropeptide Q polypeptide) with a receptor (e.g., GALR2). As the term is used herein, binding is "specific" if it occurs with an $EC_{50}$ or a Kd of 500 nM or less.

As used herein, the term "$EC_{50}$" refers to that concentration of an agent at which a given activity, including binding of a Neuropeptide Q polypeptide or other ligand and a functional activity of a GALR2 polypeptide, is 50% of the maximum for that GALR2 activity measurable using the same assay. Stated differently, the "$EC_{50}$" is the concentration of agent that gives 50% activation, when 100% activation is set at the amount of activity that does not increase with the addition of more agonist. It should be noted that the "$EC_{50}$ of a Neuropeptide Q polypeptide" will vary with the identity of the Neuropeptide Q polypeptide; for example, variant Neuropeptide Q polypeptides (i.e., those containing insertions, deletions, substitutions or fusions with other polypeptides, including Neuropeptide Q polypeptide molecules from species other than humans and variants of them that satisfy the definition of Neuropeptide Q polypeptide set forth above) can have $EC_{50}$ values higher than, lower than or the same as wild-type Neuropeptide Q polypeptide. Therefore, where a Neuropeptide Q polypeptide variant sequence differs from wild-type Neuropeptide Q polypeptide of SEQ ID NO: 12, one of the skill in the art can determine the $EC_{50}$ for that variant according to conventional methods. The $EC_{50}$ of a given Neuropeptide Q polypeptide is measured by performing an assay for an activity of a fixed amount of GALR2 polypeptide in the presence of doses of the Neuropeptide Q polypeptide that increase at least until the GALR2 response is saturated or maximal, and then plotting the measured GALR2 activity versus the concentration of Neuropeptide Q polypeptide.

As used herein, the term "IC50" is the concentration of an antagonist or inverse agonist that reduces the maximal activation of a GALR2 receptor by 50%.

As used herein, the term "Kd" refers to the dissociation constant. The dissociation constant has molar units (M), which correspond to the concentration of ligand at which the binding site on a particular protein is half occupied, i.e. the concentration of ligand, at which the concentration of protein with ligand bound, equals the concentration of protein with no ligand bound.

As used herein, the term "detectably labeled" refers to the property of a molecule, e.g., a Neuropeptide Q polypeptide or other GALR2 ligand that has a structural modification that incorporates a functional group (label) that can be readily detected. Detectable labels include but are not limited to fluorescent compounds, isotopic compounds, chemiluminescent compounds, quantum dot labels, biotin, enzymes, electron-dense reagents, and haptens or proteins for which antisera or monoclonal antibodies are available. The various means of detection include but are not limited to spectroscopic, photochemical, radiochemical, biochemical, immunochemical, or chemical means.

As used herein, the term "affinity tag" refers to a label, attached to a molecule of interest (e.g., a Neuropeptide Q polypeptide or other GALR2 ligand), that confers upon the labeled molecule the ability to be specifically bound by a reagent that binds the label. Affinity tags include, but are not limited to an epitope for an antibody (known as "epitope tags"), biotin, 6×His, and GST. Affinity tags can be used for the detection, as well as for the purification of the labeled species.

As used herein, the term "decrease in binding" refers to a decrease of at least 10% in the amount of binding detected in a given assay with a known or suspected modulator of GALR2 relative to binding detected in an assay lacking that known or suspected modulator.

As used herein, the term "delivering" when used in reference to a drug or agent, means the addition of the drug or agent to an assay mixture, or to a cell in culture. The term also refers to the administration of the drug or agent to an animal. Such administration can be, for example, by injection (in a suitable carrier, e.g., sterile saline or water) or by inhalation, or by an oral, transdermal, rectal, vaginal, or other common route of drug administration.

As used herein, the term "effective amount" refers to that amount of a drug or GALR2 modulating agent that results in a change in a GALR2 activity as defined herein (i.e., at least 10% increase or decrease in a GALR2 activity).

As used herein, the term "standard" refers to a sample taken from an individual who is not affected by a disease or disorder characterized by dysregulation of GALR2 or Neuropeptide Q polypeptide activity. The "standard" is used as a reference for the comparison of GALR2 or Neuropeptide Q polypeptide or mRNA levels and quality (i.e., mutant vs. wild-type), as well as for the comparison of GALR2 activities.

As used herein, the term "amplifying" when applied to a nucleic acid sequence, refers to a process whereby one or more copies of a nucleic acid sequence is generated from a template nucleic acid. A preferred method of "amplifying" is PCR or RT/PCR.

As used herein, the term "substantial absence" refers to a level of an activating or inhibiting factor that is below the level necessary to activate or inhibit GPCR function by at least 10% as measured by a given assay disclosed herein or known in the art.

As used herein, the term "G-Protein coupled receptor" or "GPCR" refers to a membrane-associated polypeptide with 7 alpha helical transmembrane domains. Functional GPCRs bind a ligand or an agonist and associate with and activate G-proteins.

GALR2 is a GPCR.

As used herein, the term "agent that modulates the function of a GALR2 polypeptide" is a molecule or compound that increases or decreases GALR2 activity, including molecule or compound that changes the binding of Neuropeptide Q polypeptides or other agonists, and/or molecule or compound that changes GALR2 downstream signaling activities.

As used herein, the term "transgenic animal" refers to any animal, preferably a non-human mammal, bird, fish or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one or more of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

As used herein, the term "antibody" is the conventional immunoglobulin molecule, as well as fragments thereof which are also specifically reactive with one of the subject polypeptides. Antibodies can be fragmented using conventional techniques and the fragments screened for utility in the same manner as described herein below for whole antibodies.

For example, F(ab) 2 fragments can be generated by treating antibody with pepsin. The resulting F(ab) 2 fragment can be treated to reduce disulfide bridges to produce Fab fragments. The antibody of the present invention is further intended to include bispecific, single-chain, and chimeric and humanized molecules having affinity for a polypeptide conferred by at least one CDR region of the antibody. In a preferred embodiment, the antibody further comprises attached labels which allows detection (e.g., the label can be a radioisotope, fluorescent compound, chemiluminescent compound, enzyme, or enzyme co-factor).

As used herein, the term "null mutation" refers to an insertion, deletion, or substitution that modifies the chromosomal sequences encoding a polypeptide, such that the polypeptide is not expressed.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively the term "around") placed before a temperature "Y" refers in the current application to an interval extending from the temperature Y minus 10° C. to Y plus 10° C., and preferably to an interval extending from Y minus 5° C. to Y plus 5° C.

BRIEF DESCRIPTION OF THE FIGURES

FIG. 1 illustrates human GALR2 receptor coding region cDNA (SEQ NO: 1).
FIG. 2 illustrates human GALR2 amino acid sequence (SEQ ID NO: 2).
FIG. 3 illustrates mouse GALR2 receptor coding region cDNA (SEQ NO: 3).
FIG. 4 illustrates mouse GALR2 amino acid sequence (SEQ ID NO: 4).
FIG. 5 illustrates rat GALR2 receptor coding region cDNA (SEQ NO: 5).
FIG. 6 illustrates rat GALR2 amino acid sequence (SEQ ID NO: 6).
FIG. 7 illustrates rhesus macaque GALR2 receptor coding region cDNA (SEQ NO: 7).
FIG. 8 illustrates rhesus macaque GALR2 amino acid sequence (SEQ ID NO: 8).
FIG. 9 illustrates chimpanzee GALR2 receptor coding region cDNA (SEQ NO: 9).
FIG. 10 illustrates chimpanzee GALR2 amino acid sequence (SEQ ID NO: 10).
FIG. 11 illustrates human PreproNeuropeptide Q coding region cDNA (SEQ NO: 11).
FIG. 12 illustrates human PreproNeuropeptide Q amino acid sequence (SEQ ID NO: 12).
FIG. 13 illustrates human Neuropeptide Q amino acid sequence (SEQ ID NO: 13).
FIG. 14 illustrates human Neuropeptide Q-Glycine amino acid sequence (SEQ ID NO: 14).
FIG. 15 illustrates rat Neuropeptide Q amino acid sequence (SEQ ID NO: 15).
FIG. 16 illustrates human pro Neuropeptide Q (36-58) amino acid sequence (SEQ ID NO: 16).
FIG. 17 illustrates human pro Neuropeptide Q (73-116) amino acid sequence (SEQ ID NO: 17).
FIG. 18 illustrates truncated human Neuropeptide Q amino acid sequence (SEQ ID NO: 18).
FIG. 19 illustrates truncated human Neuropeptide Q amino acid sequence (SEQ ID NO: 19).
FIG. 20 illustrates truncated human Neuropeptide Q amino acid sequence (SEQ ID NO: 20).
FIG. 21 illustrates truncated human Neuropeptide Q amino acid sequence (SEQ ID NO: 21).
FIG. 22 illustrates truncated human Neuropeptide Q-Glycine amino acid sequence (SEQ ID NO: 22).
FIG. 23 illustrates human Neuropeptide Q-Glycine amino acid sequence with substitution by alanine (SEQ ID NO: 23).
FIG. 24 illustrates human Neuropeptide Q-Glycine amino acid sequence with substitution by alanine (SEQ ID NO: 24).
FIG. 25 illustrates human Neuropeptide Q-Glycine amino acid sequence with substitution by alanine (SEQ ID NO: 25).
FIG. 26 illustrates human Neuropeptide Q-Glycine amino acid sequence with substitution by alanine (SEQ ID NO: 26).
FIG. 27 illustrates human Neuropeptide Q-Glycine amino acid sequence with substitution by alanine (SEQ ID NO: 27).
FIG. 28 illustrates human Neuropeptide Q-Glycine amino acid sequence with substitution by alanine (SEQ ID NO: 28).
FIG. 29 illustrates human Neuropeptide Q-Glycine amino acid sequence with substitution by alanine (SEQ ID NO: 29).
FIG. 30 illustrates human Neuropeptide Q-Glycine amino acid sequence with substitution by alanine (SEQ ID NO: 30).
FIG. 31 illustrates human Neuropeptide Q-Glycine amino acid sequence with substitution by alanine (SEQ ID NO: 31).
FIG. 32 illustrates human Neuropeptide Q-Glycine amino acid sequence with substitution by alanine (SEQ ID NO: 32).
FIG. 33 illustrates human Neuropeptide Q-Glycine amino acid sequence with substitution by proline (SEQ ID NO: 33).
FIG. 34 illustrates human Neuropeptide Q-Glycine amino acid sequence with substitution by proline (SEQ ID NO: 34).
FIG. 35 illustrates human Neuropeptide Q-Glycine amino acid sequence with substitution by proline (SEQ ID NO: 35).
FIG. 36 illustrates human Neuropeptide Q-Glycine amino acid sequence with substitution by proline (SEQ ID NO: 36).
FIG. 37 illustrates human Neuropeptide Q-Glycine amino acid sequence with substitution by proline (SEQ ID NO: 37).
FIG. 38 illustrates human Neuropeptide Q-Glycine amino acid sequence with substitution by proline (SEQ ID NO: 38).
FIG. 39 illustrates human Neuropeptide Q-Glycine amino acid sequence with substitution by proline (SEQ ID NO: 39).
FIG. 40 illustrates human Neuropeptide Q-Glycine amino acid sequence with substitution by proline (SEQ ID NO: 40).
FIG. 41 illustrates human Neuropeptide Q-Glycine amino acid sequence with substitution by proline (SEQ ID NO: 41).
FIG. 42 illustrates the alignment of PreproNeuropeptide Q from different species.
FIG. 43 illustrates the effect of Neuropeptide Q polypeptide on the inhibition of the binding of galanin on GALR2.
FIG. 44 illustrates the effect of Neuropeptide Q polypeptide on the release of intracellular calcium by GALR2.
FIG. 45 illustrates the effect of Neuropeptide Q polypeptide on the inhibition of cAMP release by GALR2.
FIG. 46 illustrates the effect of Neuropeptide Q polypeptide on inositol phosphate release by GALR2.
FIG. 47 illustrates the effect of Neuropeptide Q polypeptide on GTP-γ-S binding by GALR2.
FIG. 48 illustrates the effect of Neuropeptide Q polypeptide on beta-arrestin 2 recruitment by GALR2 using the DiscoveRx technology.
FIG. 49 illustrates the effect of Neuropeptide Q polypeptide on beta-arrestin 2 recruitment by GALR2 using the Tango technology.
FIG. 50 illustrates the effect of human Neuropeptide Q-Glycine polypeptide, rat Neuropeptide Q polypeptide, human pro Neuropeptide Q (36-58) polypeptide and human pro Neuropeptide Q (73-116) polypeptide on the release of calcium by GALR2.

DETAILED DESCRIPTION OF THE INVENTION

The invention relates to the identification of Neuropeptide Q polypeptides as ligands for the GALR2 GPCR. These ligand-receptor interactions are useful for screening assays for agents that modulate the interaction of endogeneous ligands with GALR2. Such agents may also modulate the function of GALR2. The known Neuropeptide Q polypeptides and their interaction with the receptor also provide tools for the diagnosis of conditions involving dysregulated receptor activity.

I. Assays for the Identification of Agents that Modulate the Activity of GALR2.

Agents that modulate the activity of GALR2 can be identified in a number of ways that take advantage of the interaction of the receptor with Neuropeptide Q polypeptide. For example, the ability to reconstitute GALR2/Neuropeptide Q polypeptide interaction either in vitro, on cultured cells or in vivo provides a target for the identification of agents that disrupt that binding. Assays based on disruption of interaction can identify agents, such as small organic molecules, from libraries or collections of such molecules. Alternatively, such assays can identify agents in samples or extracts from natural sources, e.g., plant, fungal or bacterial extracts or even in human tissue samples (e.g., tumor tissue). In one aspect, the extracts can be made from cells expressing a library of variant nucleic acids, peptides or polypeptides, including, for example, variants of Neuropeptide Q polypeptide itself.

Modulators of GALR2/Neuropeptide Q polypeptide interaction can then be screened using a binding assay or a functional assay that measures downstream signaling through the receptor. Both binding assays and functional assays are validated using Neuropeptide Q polypeptide.

Another approach that uses the GALR2/Neuropeptide Q polypeptide interaction more directly to identify agents that modulate GALR2 function measures changes in GALR2 downstream signaling induced by candidate agents or candidate modulators. These functional assays can be performed in isolated cell membrane fractions or on cells expressing the receptor on their surfaces.

The following description provides methods for both binding and functional assays based upon the interaction of GALR2 and Neuropeptide Q polypeptide.

A. GALR2 Polypeptides.

Assays using the interaction of GALR2 and Neuropeptide Q polypeptide require a source of GALR2 polypeptide. The polynucleotide and polypeptide sequence of human GALR2 are presented herein as SEQ ID NOs: 1 and 2. The polynucleotide and polypeptide sequence of mouse GALR2 are presented herein as SEQ ID NOs: 3 and 4. The polynucleotide and polypeptide sequence of rat GALR2 are presented herein as SEQ ID NOs: 5 and 6. The polynucleotide and polypeptide sequence of rhesus macaque GALR2 are presented herein as SEQ ID NOs: 7 and 8. The polynucleotide and polypeptide sequence of chimpanzee GALR2 are presented herein as SEQ ID NOs: 9 and 10.

GALR2 polypeptide sequence is also recorded at accession NOs. 043603, A5JUU4 and Q32MN8 in the Swissprot database. Related sequences include those for human GALR2 (GenBank Accession NO. NP003848 (polypeptide sequence) and GenBank Accession NO. AF040630 (nucleotide sequence)), mouse GALR2 (GenBank Accession NO. AF042784 (nucleotide sequence) and Swissprot Accession NO. 088854 (polypeptide sequence)), rat GALR2 (GenBank Accession NO. AF010318 (nucleotide sequence) and Swissprot Accession NO. 008726 (polypeptide sequence)), rhesus macaque (Ensembl Accession NO. ENSMMUT00000012422 (nucleotide sequence) and Ensembl Accession NO. ENSMMUP00000011651 (polypeptide sequence)), and chimpanzee (Ensembl Accession NO. ENSPTRT00000017739 (nucleotide sequence) and Ensembl Accession NO. ENSPTRP00000016435 (polypeptide sequence)).

One skilled in the art can readily amplify a GALR2 sequence from a sample containing mRNA encoding the protein through basic PCR and molecular cloning techniques using primers or probes designed based on known sequences.

The expression of recombinant polypeptides is well known in the art. Those skilled in the art can readily select vectors and expression control sequences for the expression of GALR2 polypeptides useful according to the invention in eukaryotic or prokaryotic cells.

GALR2 must be associated with cell membrane or detergents like synthetic liposomes in order to have binding or signaling function. Methods for the preparation of cellular membrane fractions are well known in the art, e.g., the method reported by Hubbard and Cohn (J. Cell Biol., 64: 461-479, 1975). In order to produce membranes comprising GALR2, one need only apply such techniques to cells endogenously or recombinantly expressing GALR2. Alternatively, membrane-free GALR2 can be integrated into membrane preparations by dilution of detergent solution of the polypeptide (e.g., Salamon et al., Biophys. J., 71: 283-294, 1996).

B. Neuropeptide Q Polypeptides.

The polynucleotide sequence of human Prepro Neuropeptide Q is presented herein as SEQ ID No:11. The polypeptide sequence of human Prepro Neuropeptide Q is presented herein as SEQ ID NO: 12. The polypeptide sequence of human Neuropeptide Q is presented herein as SEQ ID No:13.

Human Prepro Neuropeptide Q polypeptide sequence is also recorded at accession NO. Q9BT56 in the Swissprot database. Human polynucleotide sequence is also recorded at accession NO. BC004336.1. Related polypeptide sequences include those from different species and described as Ensembl accession NOs and sequences in FIG. 42.

As with GALR2, Neuropeptide Q polynucleotides can be cloned through standard PCR and molecular cloning techniques using the known sequences as a source of amplification primers or probes. Similarly, cloned Neuropeptide Q polypeptides can be expressed in eukaryotic or prokaryotic cells as known in the art. As a non-limiting example, a mammalian Neuropeptide Q expression vector system can comprise a bicistronic expression vector containing the promoter of human EFIa (described by Mishizuma and Nagata, Nucl. Acids Res., 18: 5322, 1990), a polylinker, the ECMV internal ribosome entry site (IRES, described by Ghattas et al., Mol. Cell. Biol., 11: 5848-5859, 1991) and the neomycin resistance gene followed by an SV40 polyA signal. Neuropeptide Q polypeptide can also be expressed in vitro through in vitro transcription and translation.

Further, if desired for a given assay or technique, Neuropeptide Q polypeptides can according to the invention be produced as fusion proteins or tagged proteins. For example, either full length Neuropeptide Q polypeptide or a portion thereof (i.e., at least 10 amino acids, preferably at least 13 amino acids or more, up to one amino acid less than full length Neuropeptide Q polypeptide) can be fused to Glutathione-S-Transferase (GST), secreted alkaline phosphatase (SEAP), a FLAG tag, a Myc tag, or a 6x-His peptide to facilitate the purification or detection of the Neuropeptide Q polypeptide. Methods and vectors for the production of tagged or fusion proteins are well known in the art, as are methods of isolating and detecting such fused or tagged proteins.

Neuropeptide Q polypeptides and particularly truncated forms can also be prepared by chemical synthesis as known in the art.

Recombinant Neuropeptide Q polypeptides can be used in purified form. Alternatively, conditioned medium from Neuropeptide Q transfected cells can be used. The amounts of Neuropeptide Q necessary in a given binding or functional assay according to the invention will vary depending upon the assay. The affinities and $EC_{50}$ values of tagged Neuropeptide Q polypeptides for GALR2 may vary relative to those of full length wild type Neuropeptide Q polypeptide (SEQ ID NOs: 12, 13 or 14), and the amount necessary for a given assay can therefore be adjusted relative to the wild-type values. If necessary for a given assay, Neuropeptide Q polypeptides can be labeled by incorporation of radiolabeled amino acids in the medium during synthesis, e.g., $^{35}S$-labeled amino acids like $^{35}S$-Met, $^{14}C$-labeled amino acids like $^{14}C$-Leu, $^{3}H$-labeled (tritiated) amino acids, or others as appropriate. Methods of chemical labeling are known in the art.

Fluorescent labels can also be attached to Neuropeptide Q polypeptides or to other GALR2 ligands using standard labeling techniques.

C. Assays to Identify Modulators of GALR2 Activity.

The identification of Neuropeptide Q polypeptides as ligands of the GALR2 receptor permits screening assays to identify agonists, antagonists and inverse agonists of receptor activity. The screening assays will have two general approaches.

1) Ligand binding assays, in which cells expressing GALR2, membrane extracts from such cells, or immobilized lipid membranes comprising GALR2 are exposed to a labeled Neuropeptide Q polypeptide and candidate compound. Following incubation, the reaction mixture is measured for specific binding of the labeled Neuropeptide Q polypeptide to the GALR2 receptor. Compounds that interfere with or displace labeled Neuropeptide Q polypeptide can be agonists, antagonists or inverse agonists of GALR2 activity. Functional analysis can be performed on positive compounds to determine which of these categories they fit.

2) Functional assays, in which a signaling activity of GALR2 is measured. a) For agonist screening, cells expressing GALR2 or membranes prepared from them are incubated with candidate compound, and a signaling activity of GALR2 is measured. The assays are validated using a Neuropeptide Q polypeptide as agonist, and the activity induced by compounds that modulate receptor activity is compared to that induced by Neuropeptide Q polypeptide. An agonist or partial agonist will have a maximal biological activity corresponding to at least 10% of the maximal activity of wild type human Neuropeptide Q polypeptide (SEQ ID NOs: 12, 13 or 14) when the agonist or partial agonist is present, and preferably will have 50%, 75%, 100% or more, including 2-fold, 5-fold, 10-fold or more activity than wild-type human Neuropeptide Q polypeptide. b) For antagonist or inverse agonist screening, cells expressing GALR2 or membranes isolated from them are assayed for signaling activity in the presence of a Neuropeptide Q polypeptide with or without a candidate compound. Antagonists or inverse agonists will reduce the level of Neuropeptide Q polypeptide-stimulated receptor activity by at least 10%, relative to reactions lacking the antagonist or inverse agonist. c) For inverse agonist screening, cells expressing constitutive GALR2 activity or membranes isolated from them are used in a functional assay that measures receptor activity in the presence and absence of a candidate compound. Inverse agonists are those compounds that reduce the constitutive activity of the receptor by at least 10%. Overexpression of GALR2 (i.e., expression of 5-fold or higher excess of GALR2 polypeptide relative to the level naturally expressed in cells in vivo) may lead to constitutive activation. GALR2 can be overexpressed by placing it under the control of a strong constitutive promoter, e.g., the CMV early promoter. Alternatively, certain mutations of conserved GPCR amino acids or amino acid domains tend to lead to constitutive activity (Kjelsberg et al., J. Biol. Chem., 267: 1430-1433, 1992; McWhinney et al., J. Biol. Chem., 275: 2087-2097, 2000; Ren et al., J. Biol. Chem., 268: 16483-16487, 1993; and Parma et al., Nature, 365: 649-651, 1993).

Ligand Binding and Displacement Assays:

One can use GALR2 polypeptides expressed on a cell, or isolated membranes containing receptor polypeptides, along with a Neuropeptide Q polypeptide in order to screen for compounds that inhibit the binding of Neuropeptide Q polypeptide to GALR2. When identified in an assay that measures binding or Neuropeptide Q polypeptide displacement alone, compounds will have to be subjected to functional testing to determine whether they act as agonists, antagonists or inverse agonists.

For displacement experiments, cells expressing a GALR2 polypeptide are incubated in binding buffer with labeled Neuropeptide Q polypeptide in the presence or absence of increasing concentrations of a candidate modulator. To validate and calibrate the assay, control competition reactions using increasing concentrations of unlabeled Neuropeptide Q polypeptide can be performed. After incubation, cells are washed extensively, and bound, labeled Neuropeptide Q polypeptide is measured as appropriate for the given label (e.g., scintillation counting, enzyme assay, fluorescence, etc.). A decrease of at least 10% in the amount of labeled Neuropeptide Q polypeptide bound in the presence of candidate modulator indicates displacement of binding by the candidate modulator. Candidate modulators are considered to bind specifically in this or other assays described herein if they displace 50% of labeled Neuropeptide Q polypeptide (sub-saturating Neuropeptide Q polypeptide dose).

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of a Neuropeptide Q polypeptide from the aqueous phase to a GALR2 polypeptide immobilized in a membrane on the sensor. This change in mass is measured as resonance units versus time after injection or removal of the Neuropeptide Q polypeptide or the candidate modulator and can be measured using for instance a Biacore Biosensor (Biacore AB). GALR2 can be immobilized on a sensor chip (for example, research grade CM5 chip; Biacore AB) in a thin film lipid membrane according to methods described by Salamon et al. (Biophys J. 71: 283-294; Biophys. J., 80: 1557-1567, 2001; Trends Biochem. Sci., 24: 213-219, 1999). Sarrio et al. demonstrated that SPR can be used to detect ligand binding to the class A GPCR (1) adenosine receptor immobilized in a lipid layer on the chip. Conditions for Neuropeptide Q polypeptide binding to GALR2 in a SPR assay can be fine-tuned by one of skill in the art using as a starting point the conditions reported by Sarrio et al. (Mol. Cell. Biol., 20: 5164-5174, 2000).

SPR can assay for modulators of binding in at least two ways. First, a Neuropeptide Q polypeptide can be pre-bound to immobilized GALR2 polypeptide, followed by injection of candidate modulator at 10 μl/min flow rate and a concentration ranging from 1 nM to 100 μM. Displacement of the bound Neuropeptide Q polypeptide can be quantified, permitting detection of modulator binding. Alternatively, the membrane-bound GALR2 polypeptide can be pre-incubated with candidate modulator and challenged with a Neuropeptide Q polypeptide. A difference in Neuropeptide Q polypeptide binding to the GALR2 exposed to modulator relative to that on a chip not pre-exposed to modulator will demonstrate binding. In either assay, a decrease of 10% or more in the amount of a Neuropeptide Q polypeptide bound in the presence of candidate modulator, relative to the amount of a Neuropeptide Q polypeptide bound in the absence of candidate modulator, indicates that the candidate modulator inhibits the interaction of GALR2 and Neuropeptide Q polypeptide.

Another method of measuring inhibition of binding of a Neuropeptide Q polypeptide to GALR2 uses fluorescence resonance energy transfer (FRET). FRET is a quantum mechanical phenomenon that occurs between a fluorescence donor (D) and a fluorescence acceptor (A) in close proximity to each other (usually <100 Angstrom of separation) if the emission spectrum of D overlaps with the excitation spectrum of A. The molecules to be tested, e.g., a Neuropeptide Q polypeptide and a GALR2 polypeptide, are labeled with a complementary pair of donor and acceptor fluorophore. While bound closely together by the GALR2-Neuropeptide Q polypeptide interaction, the fluorescence emitted upon excitation of the donor fluorophore will have a different wavelength than that emitted in response to that excitation wavelength when the polypeptides are not bound, providing for quantification of bound versus unbound polypeptides by measurement of emission intensity at each wavelength. Donor:Acceptor pairs of fluorophores with which to label the polypeptides are well known in the art. Of particular interest are variants of the A. victoria GFP known as Cyan FP (CFP, Donor (D)) and Yellow FP (YFP, Acceptor (A)). The GFP variants can be made as fusion proteins with the respective members of the binding pair to serve as D-A pairs in a FRET scheme to measure protein-protein interaction. Vectors for the expression of GFP variants as fusions are known in the art. As an example, a CFP-Neuropeptide Q polypeptide fusion and a YFP-GALR2 fusion can be made. The addition of a candidate modulator to the mixture of labeled Neuropeptide Q polypeptide and GALR2 proteins will result in an inhibition of energy transfer evidenced by, for example, a decrease in YFP fluorescence relative to a sample without the candidate modulator.

In an assay using FRET for the detection of GALR2-Neuropeptide Q polypeptide interaction, a 10% or greater decrease in the intensity of fluorescent emission at the acceptor wavelength in samples containing a candidate modulator, relative to samples without the candidate modulator, indicates that the candidate modulator inhibits GALR2-Neuropeptide Q polypeptide interaction.

A variation of FRET uses fluorescence quenching to monitor molecular interactions: One molecule in the interacting pair can be labeled with a fluorophore, and the other with a molecule that quenches the fluorophore fluorescence when brought into close apposition. A change in fluorescence upon excitation is indicative of a change in the association of the molecules tagged with the fluorophore:quencher pair. Generally, an increase in fluorescence of the labeled GALR2 polypeptide is indicative that the Neuropeptide Q polypeptide bearing the quencher has been displaced. For quenching assays, a 10% or greater increase in the intensity of fluorescent emission in samples containing a candidate modulator, relative to samples without the candidate modulator, indicates that the candidate modulator inhibits GALR2-Neuropeptide Q polypeptide interaction.

In addition to the surface plasmon resonance and FRET methods, fluorescence polarization measurement is useful to quantify protein-protein binding. The fluorescence polarization value for a fluorescently-tagged molecule depends on the rotational correlation time or tumbling rate. Protein complexes, such as those formed by GALR2 associated with a fluorescently labeled Neuropeptide Q polypeptide, have higher polarization values than uncomplexed, labeled Neuropeptide Q polypeptide. The inclusion of a candidate inhibitor of the GALR2-Neuropeptide Q polypeptide interaction results in a decrease in fluorescence polarization, relative to a mixture without the candidate inhibitor, if the candidate inhibitor disrupts or inhibits the interaction of GALR2 with Neuropeptide Q polypeptide. Fluorescence polarization is well suited for small molecules identification disrupting the formation of polypeptide or protein complexes. A decrease of 10% or more in fluorescence polarization in samples containing a candidate modulator, relative to fluorescence polarization in a sample lacking the candidate modulator, indicates that the candidate modulator inhibits GALR2-Neuropeptide Q polypeptide interaction.

Another Alternative for Monitoring GALR2-Neuropeptide Q Polypeptide Interactions Uses a Biosensor Assay.

ICS biosensors have been described by AMBRI (Australian Membrane Biotechnology Research Institute). In this technology, the association of macromolecules such as GALR2 and Neuropeptide Q polypeptide, is coupled to the closing of gramacidin-facilitated ion channels in suspended membrane bilayers and thus to a measurable change in the admittance (similar to impedence) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of GALR2 and Neuropeptide Q polypeptide.

It is important to note that in protein-protein interaction assays, it is possible that a modulator of the interaction does not necessarily need to directly interact with the domain(s) of the proteins that physically interact. It is also possible that a modulator will interact at a location removed from the site of protein-protein interaction and will cause, for example, a conformational change in the GALR2 polypeptide. Modulators (antagonists or agonists) that act in this manner are nonetheless of interest as agents to modulate the activity of GALR2.

Any of the binding assays described can be used to determine the presence of an agent in a sample, e.g., a tissue sample, that binds to the GALR2 receptor molecule, or that affects the binding of Neuropeptide Q polypeptide to the receptor. To do so, GALR2 polypeptide is reacted with Neuropeptide Q polypeptide or another ligand in the presence or absence of the sample. Neuropeptide Q polypeptide or ligand binding is measured as appropriate for the binding assay being used. A decrease of 10% or more in the binding of Neuropeptide Q polypeptide or other ligand indicates that the sample contains an agent that modulates GALR2 or ligand binding to the receptor polypeptide.

Functional Assays of Receptor Activity:
i. GTPase/GTP Binding Assays:

For GPCRs such as GALR2, receptor activity is measured by the GTP binding by cell membranes bearing the receptors of interest. In the method described by Traynor and Nahorski (Mol. Pharmacol., 47: 848-854, 1995), one essentially measures G-protein coupling to membranes by measuring the binding of labeled GTP. For GTP binding assays, membranes isolated from cells expressing the receptor could be incubated in a buffer containing inter alia $^{35}$S-GTP-gamma-S and GDP. After incubation unbound labeled GTP would be removed by filtration. Labeled GTP bound to the G protein would be measured by liquid scintillation counting.

In order to test the modulation of Neuropeptide Q polypeptide-induced GALR2 activity, membranes prepared from cells expressing a GALR2 polypeptide would be mixed with a Neuropeptide Q polypeptide, and the GTP binding assay would be performed in the presence and absence of a candidate modulator of GALR2 activity. A decrease of 10% or more in labeled GTP binding as measured by scintillation counting in an assay of this kind containing candidate modulator, relative to an assay without the modulator, indicates that the candidate modulator inhibits GALR2 activity.

A similar GTP-binding assay can be performed without Neuropeptide Q polypeptide to identify compounds that act as agonists. In this case, Neuropeptide Q polypeptide-stimulated GTP binding is used as a standard. A compound is considered an agonist if it induces at least 50% of the level of GTP binding induced by Neuropeptide Q polypeptide when the compound is present at 10 uM or less, and preferably will induce a level the same as or higher than that induced by Neuropeptide Q polypeptide.

GTPase activity is measured by incubating the membranes containing a GALR2 polypeptide with gamma-$^{32}$P-GTP. Active GTPase will release the label as inorganic phosphate, which is detected after separation by scintillation counting. Controls include assays using membranes isolated from cells not expressing GALR2 (mock-transfected), in order to exclude possible non-specific effects of the candidate compound.

In order to assay for the effect of a candidate modulator on GALR2-regulated GTPase activity, membrane samples are incubated with a Neuropeptide Q polypeptide, with and without a modulator, followed by the GTPase assay. A change (increase or decrease) of 10% or more in the level of GTP binding or GTPase activity relative to samples without a modulator is indicative of GALR2 modulation by a candidate modulator.

ii. Downstream Pathway Activation Assays:
a. Calcium Flux—the Aequorin-Based Assay:

The aequorin assay takes advantage of the responsiveness of mitochondrial apoaequorin to intracellular calcium release induced by GPCR activation (Stables et al, Anal. Biochem., 252: 115-126, 1997; Detheux et al., J. Exp. Med., 192 1501-1508, 2000). Briefly, GALR2-expressing clones are transfected to coexpress mitochondrial apoaequorin and Gα16. Cells are incubated with Coelenterazine H (Molecular Probes), washed (e.g. in DMEM-F12 culture medium) and resuspended at a defined concentration (e.g. around $0.5 \times 10^6$ cells/ml). Cells are then mixed with Neuropeptide Q polypeptide and light emission by the aequorin is recorded with a luminometer. Results are expressed as Relative Light Units (RLU). Controls include assays using membranes isolated from cells not expressing GALR2 (mock-transfected), in order to exclude possible non-specific effects of the candidate compound.

Aequorin activity or intracellular calcium levels are "changed" if light intensity increases or decreases by 10% or more in a sample of cells, expressing a GALR2 polypeptide and treated with a candidate modulator, relative to a sample of cells expressing the GALR2 polypeptide but not treated with the candidate modulator or relative to a sample of cells not expressing the GALR2 polypeptide (mock-transfected cells) but treated with the candidate modulator.

When performed in the absence of a Neuropeptide Q polypeptide, the assay can be used to identify an agonist of GALR2 activity. When the assay is performed in the presence of a Neuropeptide Q polypeptide, it can be used to assay for an antagonist or an allosteric modulator.

b. Adenyl Cyclase Assay:

Assays for adenyl cyclase activity are described by Kenimer & Nirenberg (Mol. Pharmacol., 20: 585-591, 1981).

According to the invention, adenylate cyclase activity is "changed" if it increases or decreases by 10% or more in a sample taken from cells treated with a candidate modulator of GALR2 activity, relative to a similar sample of cells not treated with the candidate modulator or relative to a sample of cells not expressing the GALR2 polypeptide (mock-transfected cells) but treated with the candidate modulator.

c. cAMP Assay:

Intracellular or extracellular cAMP is measured using a cAMP radioimmunoassay (RIA) or cAMP binding protein, or cAMP binding antibody according to methods widely known in the art. For example, Horton and Baxendale (Methods Mol. Biol., 41: 91-105, 1995), describe an RIA assay for cAMP measurements. A number of kits for the measurement of cAMP are commercially available. Control reactions should be performed using extracts of mock-transfected cells to exclude possible non-specific effects of some candidate modulators.

The cAMP level is "changed" if the level of cAMP detected in cells, expressing a GALR2 polypeptide and treated with a candidate modulator of GALR2 activity (or in extracts of such cells), using the RIA-based assay of Horton and Baxendale (Methods Mol. Biol., 41: 91-105, 1995), increases or decreases by at least 10% relative to the cAMP level in similar cells not treated with the candidate modulator.

d. Phospholipid Breakdown, Diacylglycerol and Inositol Triphosphate Production:

Receptors activating the phospholipid breakdown can be monitored for activity changes of known or suspected modulators of GALR2 by monitoring phospholipid breakdown, and the resulting production of second messengers Diacylglycerol (DAG) and/or inositol triphosphate (IP3). Methods of measuring each of these products are described in Phospholipid Signaling Protocols, edited by Ian M. Bird. Totowa, N.J., Humana Press, 1998. See also Rudolph et al. (J. Biol. Chem., 274: 11824-11831, 1999) which also describes an assay for phosphatidylinositol breakdown. Assays should be performed using cells or cell extracts expressing GALR2, treated or not treated with a Neuropeptide Q polypeptide with or without a candidate modulator. Control reactions should be performed using mock-transfected cells, or their extracts in order to exclude possible non-specific effects of some candidate modulators.

According to the invention, phosphatidylinositol breakdown, and DAG and/or IP3 levels are "changed" if they increase or decrease by at least 10% in a sample from cells expressing a GALR2 polypeptide and treated with a candidate modulator, relative to the level observed in a sample from cells expressing a GALR2 polypeptide that is not treated with the candidate modulator.

e. PKC Activation Assays:

Growth factor receptor tyrosine kinases tend to signal via a pathway involving protein kinase C(PKC) activation, a family of phospholipid- and calcium-dependant protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in PKC induced gene productions can be used to monitor PKC activation and thereby receptor activity. In addition, the activity of receptors that signal via PKC can be monitored through the use of reporter gene constructs driven by the control sequences of genes activated by PKC activation. This type of reporter gene-based assay is discussed in more detail below. For a more direct measure of PKC activity, the method of Kikkawa et al. (J. Biol. Chem., 257: 13341, 1982) can be used. This assay measures phosphorylation of a PKC substrate peptide, which is subsequently separated by binding to phosphocellulose paper. This PKC assay system can be used to measure purified kinase activity, or crude cellular extracts activities.

In one possible assay, the substrate is the peptide Ac-FKKSFKL-NH2, derived from the myristoylated alanine-rich protein kinase C substrate protein (MARCKS). The $K_m$ of the enzyme for this peptide is approximately 50 µM. Other basic, protein kinase C-selective peptides known in the art can also be used, at a concentration of at least 2-3 times their $K_m$. Cofactors required for the assay include calcium chloride, magnesium chloride, ATP, phosphatidylserine and diacylglycerol. Depending upon the intent of the user, the assay can be performed to determine the amount of PKC present (activating conditions) or the amount of active PKC present (non-activating conditions). For most purposes according to the invention, non-activating conditions will be used, such that the PKC that is active in the sample when it is isolated is measured, rather than measuring the PKC that can be activated. For non-activating conditions, calcium chloride is omitted in the assay in favor of EGTA. The assay is performed in a mixture containing HEPES, DTT, $MgCl_2$, ATP, gamma-32P-ATP, peptide substrate, phosphatidylserine/diacylglycerol membranes, and calcium chloride (or EGTA). Reactions are performed at the appropriate temperature (e.g. around 30° C.) for the appropriate time (e.g. around 5-10 minutes), followed by addition of ATP and EDTA, which stops the reactions.

After the reaction is stopped, a portion of each reaction is spotted onto a Whatman P81 cellulose phosphate filter, followed by washes with diluted phosphoric acid and finally with 95% EtOH.

Bound radioactivity is measured by scintillation counting. Specific activity (cpm/nmol) of the labeled ATP is determined by spotting a sample of the reaction onto P81 paper and counting without washing. Units of PKC activity are defined as nmol phosphate transferred per min.

An alternative assay can be performed using a protein kinase C Assay Kit sold by PanVera.

Assays might be performed on extracts from cells expressing a GALR2 polypeptide, treated or not treated with a Neuropeptide Q polypeptide with or without a candidate modulator. Control reactions should be performed using mock-transfected cells, or their extracts in order to exclude possible non-specific effects of some candidate modulators.

According to the invention, PKC activity is "changed" by a candidate modulator when the units of PKC measured by either assay described above increase or decrease by at least 10%, in extracts from cells expressing GALR2 and treated with a candidate modulator, compared to a reaction performed on a similar sample from cells not treated with a candidate modulator.

f. Kinase Assays:

Mitogen activated protein (MAP) kinase activity can be assayed using any of several kits available commercially, for example, the p38 MAP Kinase assay kit sold by New England Biolabs (Cat #9820) or the FlashPlate MAP Kinase assays sold by Perkin-Elmer Life Sciences.

MAP Kinase activity is "changed" if the level of activity is increased or decreased by 10% or more in a sample from cells, expressing a GALR2 polypeptide, treated with a candidate modulator relative to MAP kinase activity in a sample from similar cells not treated with the candidate modulator.

Direct assays for tyrosine kinase activity using known synthetic or natural tyrosine kinase substrates and labeled phosphate are well known, and are similar to other types of kinases assays (e.g., Ser/Thr kinases). Kinase assays can be performed with both purified kinases and crude extracts prepared from cells expressing a GALR2 polypeptide, treated with or without a Neuropeptide Q polypeptide, with or without a candidate modulator. Control reactions should be performed using mock-transfected cells, or their extracts in order to exclude possible non-specific effects of some candidate modulators. Substrates can be either full length protein or synthetic peptides representing the substrate. Pinna & Ruzzene (Biochem. Biophys. Acta. 1314: 191-225, 1996) list a number of phosphorylation substrate sites useful for measuring kinase activities. A number of kinase substrate peptides are commercially available. One that is particularly useful is the commercially available "Src-related peptide" RRLIEDAEYAARG, a peptide that represents a substrate for many receptor and nonreceptor tyrosine kinases. Because the assay described below requires binding of peptide substrates to filters, the peptide substrates should have a net positive charge to facilitate binding.

Generally, peptide substrates should have at least 2 basic residues and a free amino terminus.

Assays are generally carried out in an appropriate volume comprising kinase buffer (BSA, Tris-Cl, $MgCl_2$; depending upon the exact kinase assayed for, $MnCl_2$ can be used in place of or in addition to the $MgCl_2$), ATP, $^{32}$P-ATP, peptide substrate, cell extract containing kinase to be tested (cell extracts used for kinase assays should contain a phosphatase inhibitor like sodium orthovanadate), and $H_2O$. Reactions are performed at around 30° C., and are initiated by the addition of the cell extract.

Kinase reactions are performed for 30 seconds to about 30 minutes, followed by the addition of diluted, cold trichloroacetic acid (TCA). Samples are spun in a microcentrifuge, and a fraction of the supernatant is spotted onto Whatman P81 cellulose phosphate filter circles. The filters are washed with diluted phosphoric acid, followed by acetone. Filters are dried and incorporated $^{32}$P is measured by scintillation counting. The specific activity of ATP in the kinase reaction (e.g., in cpm/pmol) is determined by spotting a small sample of the reaction onto a P81 filter circle and counting directly, without washing. Counts per minute (cpm) obtained in the kinase reaction (minus blank) are then divided by the specific activity to determine the moles of phosphate transferred in the reaction.

Tyrosine kinase activity is "changed" if the level of kinase activity is increased or decreased by 10% or more in a sample from cells, expressing a GALR2 polypeptide, treated with a candidate modulator relative to kinase activity in a sample from similar cells not treated with the candidate modulator.

g. Transcriptional Reporters for Downstream Pathway Activation:

The intracellular signal initiated by binding of an agonist to a receptor, e.g., GALR2, sets in motion a cascade of intracellular events, the ultimate consequence of which is a rapid and detectable change in the transcription or translation of one or more genes. The activity of the receptor can therefore be monitored by measuring the expression of a reporter gene driven by control sequences responsive to GALR2 activation.

As used herein "promoter" refers to the transcriptional control elements necessary for receptor-mediated regulation of gene expression, including not only the basal promoter, but also any enhancers or transcription-factor binding sites necessary for receptor-regulated expression.

By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, CAT, GFP, beta-lactamase or beta-galactosidase are well known in the art, as are assays for the detection of their products.

Genes particularly well suited for monitoring receptor activity are the "immediate early" genes, which are rapidly induced, generally within minutes of contact between the receptor and the effector protein or the ligand. The induction of immediate early gene transcription does not require the synthesis of new regulatory proteins. In addition to rapid responsiveness to ligand binding, characteristics of preferred genes useful to make reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

An example of a gene that is responsive to a number of different stimuli is the c-fos proto-oncogene. The c-fos gene is activated in a protein-synthesis-independent manner by growth factors, hormones, differentiation-specific agents, stress, and other known inducers of cell surface proteins. The induction of c-fos expression is extremely rapid, often occurring within minutes of receptor stimulation. This characteristic makes the c-fos regulatory regions particularly attractive for use as a reporter of receptor activation.

The transcription factor CREB (cyclic AMP responsive element binding protein) is, as the name implies, responsive to levels of intracellular cAMP. Therefore, the activation of a receptor that signals via modulation of cAMP levels can be monitored by measuring either the binding of the transcription factor, or the expression of a reporter gene linked to a CREB-binding element (termed CRE, or cAMP response element). Reporter constructs responsive to CREB binding activity are described in U.S. Pat. No. 5,919,649.

Other promoters and transcriptional control elements, in addition to the c-fos elements and CREB-responsive constructs, include the vasoactive intestinal peptide (VIP) gene promoter (cAMP responsive; Fink et al., Proc. Natl. Acad. Sci., 85: 6662-6666, 1988); the somatostatin gene promoter (cAMP responsive; Montminy et al., Proc. Natl. Acad. Sci., 8. 3: 6682-6686, 1986); the proenkephalin promoter (responsive to cAMP, nicotinic agonists, and phorbol esters; Comb et al., Nature, 323: 353-356, 1986); the phosphoenolpyruvate carboxy-kinase (PEPCK) gene promoter (cAMP responsive; Short et al., J. Biol. Chem., 261: 9721-9726, 1986).

Additional examples of transcriptional control elements that are responsive to changes in GPCR activity include, but are not limited to those responsive to the AP-1 transcription factor and those responsive to NF-kB activity.

A given promoter construct should be tested by exposing GALR2-expressing cells, transfected with the construct, to a Neuropeptide Q polypeptide. An increase of at least two-fold in the reporter expression in response to Neuropeptide Q polypeptide indicates that the reporter is an indicator of GALR2 activity.

In order to assay GALR2 activity with a Neuropeptide Q polypeptide-responsive transcriptional reporter construct, cells stably expressing a GALR2 polypeptide are stably transfected with the reporter construct. To screen for agonists, the cells are left untreated, exposed to candidate modulators, or exposed to a Neuropeptide Q polypeptide, and expression of the reporter is measured. The Neuropeptide Q polypeptide-treated cultures serve as a standard for the level of transcription induced by a known agonist. An increase of at least 20% in reporter expression in the presence of a candidate modulator indicates that the candidate is a modulator of GALR2 activity. An agonist will induce at least 20%, and preferably the same amount or more, reporter expression than the Neuropeptide Q polypeptide. This approach can also be used to screen for inverse agonists where cells express a GALR2 polypeptide at levels such that there is an elevated basal activity of the reporter in the absence of Neuropeptide Q polypeptide or another agonist. A decrease in reporter activity of 10% or more in the presence of a candidate modulator, relative to its absence, indicates that the compound is an inverse agonist.

To screen for antagonists, the cells expressing GALR2 and carrying the reporter construct are exposed to a Neuropeptide Q polypeptide (or another agonist) in the presence and absence of candidate modulator. A decrease of 10% or more in reporter expression in the presence of candidate modulator, relative to the absence of the candidate modulator, indicates that the candidate is a modulator of GALR2 activity.

Controls for transcription assays include cells not expressing GALR2 but carrying the reporter constructs, as well as cells with a promoterless reporter construct. Compounds that are identified as GALR2-regulated transcription modulators should also be analyzed to determine whether they affect transcription driven by other regulatory sequences and by other receptors, in order to determine the specificity and spectrum of their activity.

The transcriptional reporter assays, and most cell-based assays, are well suited for screening expression libraries for proteins for those that modulate GALR2 activity. The libraries can be, for example, cDNA libraries from natural sources, e.g., plants, animals, bacteria, etc., or libraries expressing randomly or systematically mutated variants of one or more polypeptides. Genomic libraries in viral vectors can also be used to express the mRNA content of one cell or tissue, in the different libraries used for screening of GALR2.

Any of the assays of receptor activity, including the GTP-binding, GTPase, adenylate cyclase, cAMP, phospholipid-breakdown, DAG, IP3, PKC, kinase and transcriptional reporter assays, can be used to determine the presence of an agent in a sample, e.g., a tissue sample, that affects the activity of the GALR2 receptor molecule. To do so, GALR2 polypeptide is assayed for activity in the presence and absence of the sample or an extract of the sample. An increase in GALR2 activity in the presence of the sample or extract relative to the absence of the sample indicates that the sample contains an agonist of the receptor activity. A decrease in receptor activity in the presence of Neuropeptide Q polypeptide or another agonist and the sample, relative to receptor activity in the presence of Neuropeptide Q polypeptide alone, indicates that the sample contains an antagonist of GALR2 activity. If desired, samples can then be fractionated and further tested to isolate or purify the agonist or antagonist. The amount of increase or decrease in measured activity necessary for a sample to be said to contain a modulator depends upon the type of assay used. Generally, a 10% or greater change (increase or decrease) relative to an assay performed in the absence of a sample indicates the presence of a modulator in the sample. It is preferred that an agonist stimulates at least 20%, and preferably 75% or 100% or more, e.g., 2-fold, 5-fold, 10-fold or greater receptor activation than Neuropeptide Q polypeptide.

Other functional assays include, for example, microphysiometer or biosensor assays (Hafner, Biosens. Bioelectron., 15: 149-158, 2000).

II. Diagnostic Assays Based Upon the Interaction of GALR2 and Neuropeptide Q Polypeptide:

GPCR signaling dysregulation is important in pathology development of a large number of diseases and disorders. GALR2 has been shown to act as a co-receptor for immunodeficiency viruses and can have a role in immune processes, disorders or diseases. The GALR2 expression patterns also suggest that this receptor can play a role in other diseases, disorders or processes, wherein said GALR2-related diseases or GALR2-related disorders are as defined above.

The interaction of GALR2 with Neuropeptide Q polypeptide can be used as the basis of assays for the diagnosis or monitoring of diseases, disorders or processes involving GALR2 signaling.

Diagnostic assays for GALR2-related diseases, disorders, or processes can have several different forms.

First, diagnostic assays can measure the amount of GALR2 and/or Neuropeptide Q polypeptide or genes in a sample of tissue. Assays that measure the amount of mRNA encoding either a single or both of these polypeptides also fit in this category.

Second, assays can evaluate the qualities of the receptor or the ligand. For example, assays that determine whether an individual expresses a mutant or variant form of either GALR2 or Neuropeptide Q polypeptide, or both, can be used diagnostically.

Third, assays that measure one or more activities of GALR2 polypeptide can be used diagnostically.

Therefore, the present invention relates to diagnostic assays for GALR2-related diseases, disorders, or processes. GALR2-related diseases, GALR2-related disorders, or GALR2-related processes might be part from a group as defined above.

The present invention also relates to diagnostic assays for Neuropeptide Q polypeptide-related diseases, disorders, or processes, wherein said Neuropeptide Q polypeptide-related diseases or Neuropeptide Q polypeptide-related disorders are as defined above.

According to the present method, said Neuropeptide Q polypeptide may be a polypeptide having at least 31% identity, and preferably at least 50%, more preferably at least 75%, most preferably at least 95% and notably 100% identity, to the polypeptide represented by SEQ ID NO: 13, SEQ ID NO: 14, SEQ ID NO: 15 or SEQ ID NO: 16 (notably SEQ ID NO: 13); and wherein said polypeptide binds specifically to and activates a signaling activity of a GALR2 polypeptide having the sequence of SEQ ID NO: 2. Alternatively, said Neuropeptide Q polypeptide may be a fragment of the full length polypeptide of SEQ ID NO: 13, SEQ ID NO: 14, SEQ ID NO: 15 or SEQ ID NO: 16 (notably SEQ ID NO: 13), wherein the fragment retains at least 10% (preferably at least 50%) of the binding activity and/or level of signaling activation of the full length polypeptide of SEQ ID NO: 13.

According to the present invention, said Neuropeptide Q polypeptide may comprise one or more additions, insertions, deletions or substitutions relative to SEQ ID NO: 13, SEQ ID NO: 14, SEQ ID NO: 15 or SEQ ID NO: 16 (notably SEQ ID NO: 13). Said Neuropeptide Q polypeptide may comprise additional sequences forming a Neuropeptide Q fusion protein, wherein said additional sequences may be chosen from the group consisting of glutathione-S-transferase (GST), maltose binding protein, alkaline phosphatase, thioredoxin, green fluorescent protein (GFP), histidine tags (e.g., 6× or greater His), or epitope tags (e.g., HA-tag, Myc tag, FLAG tag) sequences.

A. Assays that Measure the Amount of GALR2 or Neuropeptide Q Polypeptide.

GALR2 and Neuropeptide Q polypeptide levels can be measured and compared to standards in order to determine whether an abnormal level of the receptor or its ligand is present in a sample, either of which indicates probable dysregulation of GALR2 signaling. Polypeptide levels are measured, for example, by immunohistochemistry using antibodies specific for the polypeptide. A sample isolated from an individual suspected of suffering from a disease or disorder characterized by GALR2 activity is contacted with an antibody for GALR2 or Neuropeptide Q polypeptide, and binding of the antibody is measured as known in the art (e.g., by measurement of the activity of an enzyme conjugated to a secondary antibody).

Another approach to the measurement of GALR2 and/or Neuropeptide Q polypeptide levels uses flow cytometry analysis of cells from an affected tissue. Methods of flow cytometry, including the fluorescent labeling of antibodies specific for GALR2 or Neuropeptide Q polypeptide, are well known in the art. Other approaches include radioimmunoassay or ELISA. Methods for each of these are also well known in the art.

The amount of binding detected is compared to the binding in a sample of similar tissue from a healthy individual, or from a site on the affected individual that is not or less affected (preferably not affected). An increase of 10% or more relative to the standard is diagnostic for a disease or disorder characterized by GALR2 dysregulation.

GALR2 and Neuropeptide Q polypeptide expression can also be measured by determining the amount of mRNA encoding either or both of the polypeptides in a sample of tissue. mRNA can be quantitated by quantitative or semi-quantitative PCR. Methods of "quantitative" amplification are well known to those of skill in the art, and primer sequences for the amplification of both GALR2 and Neuropeptide Q polypeptide are disclosed herein. A common quantitative PCR method involves simultaneously co-amplifying a known quantity of a control sequence using the same primers.

This provides an internal standard that can be used to calibrate the PCR reaction. Detailed protocols for quantitative PCR are provided in PCR Protocols, A Guide to Methods and Applications, Innis et al., Academic Press, Inc. N.Y., (1990), which is incorporated herein by reference. An increase of 10% or more in the amount of mRNA encoding GALR2 or Neuropeptide Q polypeptide in a sample, relative to the amount expressed in a sample of like tissue from a healthy individual or in a sample of tissue from an unaffected location in an affected individual is diagnostic for a disease or disorder characterized by dysregulation of GALR2 signaling.

B. Qualitative Assays.

Assays that evaluate whether or not the GALR2 polypeptide or the mRNA encoding it are wild-type or not can be used diagnostically.

In order to diagnose a disease or disorder characterized by GALR2 or Neuropeptide Q polypeptide dysregulation in this manner, RNA isolated from a sample is used as a template for PCR amplification of Neuropeptide Q polypeptide and/or GALR2. The amplified sequences are either directly sequenced using standard methods, or cloned into a vector and sequenced. A difference in the sequence that changes one or more encoded amino acids relative to the sequence of wild-type GALR2 or Neuropeptide Q polypeptide can be diagnostic of a disease or disorder characterized by dysregulation of GALR2 signaling. It can be useful, when a change in coding sequence is identified in a sample, to express the variant receptor or ligand and compare its activity to that of wild type GALR2 or Neuropeptide Q polypeptide. Among other benefits, this approach can provide novel mutants, including constitutively active and null mutants.

In addition to standard sequencing methods, amplified sequences can be assayed for the presence of specific mutations using, for example, hybridization of molecular beacons that discriminate between wild-type and variant sequences. Hybridization assays that discriminate on the basis of changes as small as one nucleotide are well known in the art. Alternatively, any of a number of "minisequencing" assays can be performed, including, those described, for example, in U.S. Pat. No. 5,888,819, U.S. Pat. No. 6,004,744 and U.S. Pat. No. 6,013,431. These assays and others known in the art can determine the presence, in a given sample, of a nucleic acid with a known polymorphism.

If desired, array or microarray-based methods can be used to analyze the expression or the presence of mutation, in GALR2 or Neuropeptide Q polypeptide sequences. Array-based methods for minisequencing and for quantitation of nucleic acid expression are well known in the art.

C. Functional Assays.

Diagnosis of a disease or disorder characterized by the GALR2 signaling dysregulation can also be performed using functional assays. To do so, cell membranes or cell extracts prepared from a tissue sample are used in an assay of GALR2 activity as described herein (e.g., ligand binding assays, the GTP-binding assay, GTPase assay, adenylate cyclase assay, cAMP assay, phospholipid breakdown, DAG or IP3 assays, PKC activation assay, or kinase assay). The activity detected is compared to that in a standard sample taken from a healthy individual or from an unaffected site on the affected individual. As an alternative, a sample or extract of a sample can be applied to cells expressing GALR2, followed by measurement of GALR2 signaling activity relative to a standard sample. A difference of 10% or more in the activity measured in any of these assays, relative to the activity of the standard, is diagnostic for a disease or disorder characterized by dysregulation of GALR2 signaling.

Modulation of GALR2 Activity in a Cell According to the Invention.

The identification of Neuropeptide Q polypeptide as a ligand of GALR2 provides methods of modulating the activity of a GALR2 polypeptide in a cell. GALR2 activity is modulated in a cell by delivering to that cell an agent that modulates the function of a GALR2 polypeptide. This modulation can be performed in cultured cells as part of an assay for the identification of additional modulating agents, or, for example, in an animal, including a human. Agents include Neuropeptide Q polypeptides as defined herein, as well as additional modulators identified using the screening methods described herein.

An agent can be delivered to a cell by adding it to culture medium. The amount to deliver will vary with the identity of the agent and with the purpose for which it is delivered. For example, in a culture assay to identify antagonists of GALR2 activity, one will preferably add an amount of Neuropeptide Q polypeptide that half-maximally activates the receptors (e.g., approximately $EC_{50}$), preferably without exceeding the dose required for receptor saturation. This dose can be determined by titrating the amount of Neuropeptide Q polypeptide to determine the point at which further addition of Neuropeptide Q polypeptide has no additional effect on GALR2 activity.

When a GALR2 activity modulator is administered to an animal for the treatment of a disease or disorder, the amount administered can be adjusted by one of skill in the art on the basis of the desired outcome. Successful treatment is achieved when one or more measurable aspects of the pathology (e.g., tumor cell growth, accumulation of inflammatory cells) is changed by at least 10% relative to the value for that aspect prior to treatment.

Candidate Modulators Useful According to the Invention.

Candidate modulators can be screened from libraries of synthetic or natural compounds of any size or origin. Numerous means are currently used for random and directed synthesis of saccharide, peptide, lipid, carbohydrate, and nucleic acid based compounds. Synthetic compound libraries of different sizes, including libraries of small organic molecules, may be prepared using well known combinatorial or parallel chemistry techniques or are commercially available from a number of companies. Alternatively, libraries of natural compounds in the form of bacterial, fungal, plant and animal extracts are available from a number of companies, or are readily producible by methods well known in the art. Additionally, natural and synthetically produced libraries and compounds are readily modified through conventional chemical, physical, and biochemical means.

As noted previously herein, candidate modulators can also be variants of known polypeptides (e.g., Neuropeptide Q polypeptide, antibodies) or nucleic acids (e.g., aptamers) encoded in a nucleic acid library. Cells (e.g., bacteria, yeast or higher eukaryotic cells) transformed with the library can be grown and prepared as extracts, which are then applied in GALR2 binding assays or GALR2 activity functional assays.

Antibodies Useful According to the Invention.

The invention provides for antibodies to GALR2 and Neuropeptide Q polypeptide. Antibodies can be made using standard protocols known in the art (See, for example, Antibodies: A Laboratory Manual ed. by Harlow and Lane (Cold Spring Harbor Press: 1988)). A mammal, such as a mouse, hamster, or rabbit can be immunized with an immunogenic form of the peptide (e.g., a GALR2 or Neuropeptide Q polypeptide or an antigenic fragment which is capable of eliciting an antibody response or a fusion protein as described herein above). Immunogens for raising antibodies are prepared by mixing the polypeptides (e.g., isolated recombinant polypeptides or synthetic peptides) with adjuvants. Alternatively, GALR2 or Neuropeptide Q polypeptides or peptides are made as fusion proteins to larger immunogenic proteins. Polypeptides can also be covalently linked to other larger immunogenic proteins, such as keyhole limpet hemocyanin. Alternatively, plasmid or viral vectors encoding GALR2 or Neuropeptide Q polypeptide, or a fragment of these proteins, can be used to express the polypeptides and generate an immune response in an animal as described by Costagliola et al. (J. Clin. Invest., 105: 803-811, 2000). In order to raise antibodies, immunogens are typically administered intradermally, subcutaneously, or intramuscularly to experimental animals such as rabbits, sheep, or mice. In addition to the antibodies discussed above, genetically engineered antibody derivatives can be made, such as single chain antibodies.

The progress of immunization can be monitored by detection of antibody titers in plasma or serum. Standard ELISA, flow cytometry or other immunoassays can also be used with the immunogen as antigen to assess the levels of antibodies.

Antibody preparations can be simply serum from an immunized animal, or if desired, polyclonal antibodies can be isolated from the serum by, for example, affinity chromatography using immobilized immunogen.

To produce monoclonal antibodies, antibody-producing splenocytes can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, Nature, 256: 495-497, 1975)), the human B cell hybridoma technique (Kozbar et al., Immunology Today, 4: 72, 1983), and the EBV-hybridoma technique to produce human monoclonal antibodies (Cole et al., Monoclonal Antibodies and Cancer Therapy, Alan R. Liss, Inc. pp. 77-96, 1985). Hybridoma cells can be screened immunochemically for production of antibodies specifically reactive with a Neuropeptide Q polypeptide or GALR2 peptide or polypeptide, and monoclonal antibodies isolated from the media of a culture comprising such hybridoma cells.

Transgenic Animals Useful According to the Invention.

Transgenic animals expressing GALR2 or Neuropeptide Q polypeptide or variants thereof are useful to study the signaling through GALR2, as well as for the study of drugs or agents that modulate the activity of GALR2. A transgenic animal is a non-human animal containing at least one foreign gene, called a transgene, which is part of its genetic material. Preferably, the transgene is contained in the animal's germ line such that it can be transmitted to the animal's offspring. A number of techniques may be used to introduce the transgene into an animal's genetic material, including, but not limited to, microinjection of the transgene into pronuclei of fertilized eggs and manipulation of embryonic stem cells (U.S. Pat. No. 4,873,191; Palmiter and Brinster, Ann. Rev. Genet., 20: 465-499, 1986; French Patent Application FR2593827). Transgenic animals can carry the transgene in all their cells or can be genetically mosaic.

According to conventional transgenesis methods, additional copies of normal or modified genes are injected into the male pronucleus of the zygote and become integrated into the genomic DNA of the recipient mouse. The transgene is transmitted in a Mendelian manner in established transgenic strains. Transgenes can be constitutively expressed or can be tissue specific or even responsive to an exogenous drug, e.g., Tetracycline. A transgenic animal expressing one transgene can be crossed to a second transgenic animal expressing a second transgene such that their offspring will carry and express both transgenes.

Knock-Out Animals.

Animals bearing a homozygous deletion in the chromosomal sequences encoding either GALR2 or Neuropeptide Q polypeptide or variants can be used to study the function of the receptor and ligand. Of further particular interest is the identification of GALR2/Neuropeptide Q polypeptide in specific physiological and/or pathological processes.

i. Standard Knock Out Animals.

Knock out animals are produced by the method of creating gene deletions with homologous recombination. This technique is based on the development of embryonic stem (ES) cells that are derived from embryos, maintained in culture and have the capacity to participate in the development of every tissue in the animals when introduced into a host blastocyst. A knock out animal is produced by directing homologous recombination to a specific target gene in the ES cells, thereby producing a null allele of the gene. The technology for making knock-out animals is well described (see, for example, Huszar et al., Cell, 88: 131, 1997; and Ohki-Hamazaki et al., Nature, 390: 165, 1997). One of skill in the art can generate a homozygous GALR2 or Neuropeptide Q polypeptide knockout animal (e.g., a mouse) using the sequences for GALR2 and Neuropeptide Q (disclosed herein and known in the art) to make the gene targeting construct.

ii. Tissue Specific Knock Out.

The method of targeted homologous recombination has been improved by the development of a system for site-specific recombination based on the bacteriophage P1 site specific recombinase Cre. The Cre-loxP site-specific DNA recombinase from bacteriophage P1 is used in transgenic mouse assays in order to create gene knockouts restricted to defined tissues or developmental stages. Regionally restricted genetic deletion, as opposed to global gene knockout, has the advantage that a phenotype can be attributed to a particular cell/tissue. In the Cre-loxP system one transgenic mouse strain is engineered such that loxP sites flank one or more exons of the gene of interest. Homozygotes for this so called 'floxed gene' are crossed with a second transgenic mouse that expresses the Cre gene under control of a cell/tissue type transcriptional promoter. Cre protein then excises DNA between loxP recognition sequences and effectively removes target gene function. There are now many in vivo examples of this method, including, for instance, the inducible inactivation of mammary tissue specific genes (Wagner et al., Nucleic Acids Res., 25: 4323, 1997). One of skill in the art can therefore generate a tissue-specific knock-out animal in which GALR2 or Neuropeptide Q is homozygously eliminated in a chosen tissue or cell type.

Kits Useful According to the Invention.

The invention provides for kits useful for screening for modulators of GALR2 activity. In addition, the invention provides kits useful for diagnosis of diseases or disorders characterized by dysregulation of GALR2 signaling. Kits useful according to the invention can include an isolated GALR2 polypeptide (including a membrane- or cell-associated GALR2 polypeptide, e.g., on isolated membranes, cells expressing GALR2, or, on an SPR chip) and an isolated Neuropeptide Q polypeptide.

A kit can also comprise an antibody specific for GALR2 and/or an antibody for Neuropeptide Q polypeptide.

Alternatively, or in addition, a kit can contain cells transformed to express a GALR2 polypeptide and/or cells transformed to express a Neuropeptide Q polypeptide. In a further embodiment, a kit according to the invention can contain a polynucleotide encoding a GALR2 polypeptide and/or a polynucleotide encoding a Neuropeptide Q polypeptide. In a still further embodiment, a kit according to the invention may comprise the specific primers useful for amplification of GALR2 or Neuropeptide Q as described below. All kits according to the invention will comprise the stated items or combinations of items and packaging materials therefor. Kits may also include instructions for use.

According to the present kit, said Neuropeptide Q polypeptide may be a polypeptide having at least 31% identity, and preferably at least 50%, more preferably at least 75%, most preferably at least 95% and notably 100% identity, to the polypeptide represented by SEQ ID NO: 13, SEQ ID NO: 14, SEQ ID NO: 15 or SEQ ID NO: 16 (notably SEQ ID NO: 13); and wherein said polypeptide binds specifically to and activates a signaling activity of a GALR2 polypeptide having the sequence of SEQ ID NO: 2. Alternatively, said Neuropeptide Q polypeptide may be a fragment of the full length polypeptide of SEQ ID NO: 13, SEQ ID NO: 14, SEQ ID NO: 15 or SEQ ID NO: 16 (notably of SEQ ID NO: 13), wherein the fragment retains at least 10% (preferably at least 50%) of the binding activity and/or level of signaling activation of the full length polypeptide of SEQ ID NO: 13. According to the present invention, said Neuropeptide Q polypeptide may comprise one or more additions, insertions, deletions or substitutions relative to SEQ ID NO: 13, SEQ ID NO: 14, SEQ ID NO: 15 or SEQ ID NO: 16 (notably SEQ ID NO: 13). Examples of fragments of Neuropeptide Q polypeptides relative to SEQ ID NO. 14 are polypeptides of SEQ ID NO: 18, SEQ ID NO: 19, SEQ ID NO: 20, SEQ ID NO: 21 and SEQ ID NO: 22. Examples of Neuropeptide Q polypeptides comprising substitutions relative to SEQ ID NO. 14 are polypeptides of SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41. Said Neuropeptide Q polypeptide may comprise additional sequences forming a Neuropeptide Q fusion protein, wherein said additional sequences may be chosen from the group consisting of glutathione-S— transferase (GST), maltose binding protein, alkaline phosphatase, thioredoxin, green fluorescent protein (GFP), histidine tags (e.g., 6× or greater His), or epitope tags (e.g., HA-tag, Myc tag, FLAG tag) sequences.

Biological Assays

In Vitro Assay

The modulation of the human GALR2 receptor activity by Neuropeptide Q polypeptide is determined in accordance with the following experimental methods.

Experimental Method:

Radioligand Binding Assay:

Competition binding assay on GALR2 is performed in polyethylene MiniSorp tubes (Nunc) containing binding buffer (25 mM HEPES pH 7.4, 5 mM $MgCl_2$, 1 mM EDTA, 0.5% protease free BSA), human GALR2 membranes (0.5 µg of protein/tube), [125I]Galanin (final concentration of 1.3 nM). The candidate modulator or Neuropeptide Q polypeptide are added at increasing concentrations. The samples are incubated in a final volume of 0.1 ml for 60 min at 25° C. and then filtered on GF/C filters presoaked for at least 1 h in 0.5% PEI, using a multiple membrane filter (Linca Lamon Instrumentation, Tel Aviv, Israel). Filters are washed three times with 4 ml of ice-cold washing buffer (same composition as the binding buffer), dried and counted in a gamma counter.

Aequorin Assay:

CHO-K1 cells coexpressing mitochondrial apoaequorin, Gα16 and the recombinant human GALR2 receptor grown to mid-log phase in culture media without antibiotics are detached with PBS-EDTA, centrifuged and resuspended in assay buffer (DMEM/HAM's F12 with HEPES, without phenol red+0.1% BSA protease free) at a concentration of $1 \times 10^6$ cells/ml. Cells are incubated at room temperature for at least 4 h with Coelenterazine H. The Neuropeptide Q polypeptide is tested to evaluate the performance of the assay on each day of the test and determine $EC_{50}$. For agonist testing, 50 µl of cell suspension are mixed with 50 µl of the candidate modulator or Neuropeptide Q polypeptide in a 96-well plate. The resulting emission of light is recorded using Hamamatsu Functional Drug Screening System 6000 (FDSS 6000) luminometer. For antagonist testing 100 µl of the Neuropeptide Q polypeptide at its $EC_{80}$ is injected on the mix of cells and candidate modulator, following an incubation of 15 min after the first injection. The resulting emission of light is recorded using Hamamatsu Functional Drug Screening System 6000 (FDSS 6000) luminometer. Agonist activity of the candidate modulator is expressed as a percentage of the activity of the Neuropeptide Q polypeptide at its $EC_{100}$ concentration. Antagonist activity of the candidate modulator is expressed as a percentage of the inhibition of Neuropeptide Q polypeptide activity at its $EC_{80}$ concentration.

FLIPR Assay:

CHO-K1 cells coexpressing Gα16 and the recombinant human GALR2 receptor grown to mid-log phase in culture media are detached with PBS-EDTA, centrifuged, resuspended in cell-culture medium (HAM's F12 with HEPES, 10% (v/v) Fetal Calf Serum), and dispensed at 15'000 cells per well in 384-well FLIPR plates. After overnight incubation in in a humidified 37° C./5% CO2 incubator, the medium was discarded and replaced with a dye solution (DMEM w/o Phenol Red with HEPES, Fluo4-AM and Probenecid). After an incubation of 1 hour in a humidified 37° C./5% CO2 incubator, the dye solution was replaced by Assay Medium (HBSS/DMEM w/o phenol red). The peptides, including Neuropeptide Q, are tested to evaluate their performance in the release of intra-cellular calcium after binding to their target, GALR2. The resulting emission of fluorescence is recorded using FLIPR tetra. For antagonist testing 100 µl of the Neuropeptide Q polypeptide at its $EC_{80}$ is injected on the mix of cells and candidate modulator, following an incubation of 15 min after the first injection. The resulting emission of fluorescence is recorded using FLIPR tetra. Agonist activity of the candidate modulator is expressed as a percentage of the activity of the Neuropeptide Q polypeptide at its $EC_{100}$ concentration. Antagonist activity of the candidate modulator is expressed as a percentage of the inhibition of Neuropeptide Q polypeptide activity at its $EC_{80}$ concentration.

cAMP HTRF Assay

CHO-K1 cells expressing human recombinant GALR2 receptor grown prior to the test in media without antibiotic are detached by gentle flushing with PBS-EDTA (5 mM EDTA), recovered by centrifugation and resuspended in assay buffer (KRH: 5 mM KCl, 1.25 mM $MgSO_4$, 124 mM NaCl, 25 mM HEPES, 13.3 mM Glucose, 1.25 mM $KH_2PO_4$, 1.45 mM $CaCl_2$, 0.5 g/l BSA). Dose response curves are performed in parallel with the Neuropeptide Q polypeptide. For agonist test (96 well): 12 µl of cells are mixed with 6 µl of the candidate modulator at increasing concentrations and 6 µl of forskolin then incubated 30 min at room temperature. After addition of the lysis buffer and 1 hour incubation, cAMP concentrations are estimated, according to the manufacturer specification, with the HTRF kit. For antagonist test (96 well): 12 µl of cells are mixed with 6 µl of the candidate modulator at increasing concentrations and then incubated 10 min. Thereafter 6 µl of the mix of the forskolin and Neuropeptide Q polypeptide is added at a final concentration corresponding to the historical $EC_{80}$. The plates are then incubated for 30 min at room temperature. After addition of the lysis buffer and 1 hour incubation, cAMP concentrations are estimated, according to the manufacturer specification, with the HTRF kit.

IP1 HTRF Assay

CHO-K1 cells expressing human recombinant GALR2 receptor grown to mid-log phase in culture media without antibiotics are detached with PBS-EDTA, centrifuged and resuspended in medium without antibiotics buffer. 20,000 cells are distributed in a 96 well plate and incubated overnight at 37° C. with 5% $CO_2$. For agonist testing, the medium is removed and 20 µl of assay buffer plus 20 µl of the candidate modulator or Neuropeptide Q polypeptide are added in each well. The plate is incubated for 60 min. at 37° C. with 5% $CO_2$. IP1-D2 reagent and anti-IP1 cryptate reagents are then dispensed in the wells and IP1 concentrations are measured following the manufacturer recommendations. For antagonist testing, 20 µl of the candidate modulator or reference antagonist is added and the plate is incubated for 15 min. at 37° C. in a humidified atmosphere of 95% air with 5% $CO_2$, then 20 μl of Neuropeptide Q polypeptide at a final concentration corresponding to the historical $EC_{80}$ is added. The plate is incubated for 60 min. at 37° C. with 5% $CO_2$. IP1-D2 reagent and anti-IP1 cryptate reagents are then dispensed in the wells and IP1 concentrations are measured following the manufacturer recommendations.

GTP-γ-S Scintillation Proximity Assay

The assay buffer is composed of 20 mM HEPES pH 7.4; 200 mM NaCl, 10 μg/ml saponin, 1 mM $MgCl_2$, and 0.1% (w/v) BSA. The membranes are prepared from CHO-K1 cells expressing recombinant human GALR2 receptor. Membranes extracts are thawed on ice, diluted in assay buffer and kept on ice. GDP is diluted in assay buffer at a 1 μM final concentration. PVT-WGA Beads (Amersham, RPNQ001) are diluted in assay buffer at 50 mg/ml (0.5 mg/10 μl). GTP-γ-35S (PerkinElmer NEG030X) is diluted in assay buffer to give 0.1 nM. For agonist testing, membranes (12.5 μl) are mixed with GDP (12.5 μl). In parallel, GTP-γ-35S (12.5 μl) is mixed with the beads (12.5 μl) just before starting the reaction. The following reagents are successively added in the wells of an Optiplate (Perkin Elmer): 50 μl of the candidate modulator or Neuropetide Q polypeptide ligand, 25 μl of the membranes: GDP mix, and 25 μl of the GTP-γ-35S: beads mix. The plates are covered with a top seal, mixed on an orbital shaker for 2 min, and then incubated for 1 hour at room temperature. Then the plates are centrifuged for 10 min at 2000 rpm, incubated at room temperature 1 hour and counted for 1 min/well with a PerkinElmer TopCount reader.

TANGO® β-Arrestin Assay

TANGO GALR2 cells are detached by gentle flushing with PBS-EDTA (5 mM EDTA), recovered by centrifugation and resuspended in assay buffer (DMEM with 10% charcoal-dextran stripped FBS, 0.1 mM NEAA, 25 mM HEPES, 100 μml penicillin and 100 μg/ml streptomycin) at a density of 312,500 cells/ml. 32 μl of cell suspension (10,000 cells) is distributed in the wells of a black clear-bottom 384-well culture plate. For agonist testing, 8 μl of five fold concentrated Neuropeptide Q polypeptide or the candidate modulator in assay buffer with 0.5% DMSO is added to the wells of the culture plate. For antagonist testing, 4 μl of ten fold concentrated candidate modulator in assay buffer with 0.5% DMSO is added to the wells of the culture plate. After a 30 minutes incubation at room temperature, 4 μl of ten fold concentrated Neuropeptide Q polypeptide in assay buffer with 0.5% DMSO is added, for a final concentration corresponding to historical EC80. The plate is then incubated 16 hours in a humidified 37° C./5% CO2 incubator.

For readout, six fold concentrated LiveBlazer™-FRET B/G (CCF4-AM) substrate mix is prepared and 8 μl is dispensed in each well of the culture plate. Following 2 hours incubation at room temperature in the dark, blue (excitation 409/420 nm, emission 460/440 nm) and green (excitation 409/420 nm, emission 530/530 nm) fluorescence are measured. Background fluorescence (cell-free control wells) is subtracted and blue/green emission ratio is calculated for each well. Agonist activity of the candidate modulator will be expressed as a percentage of the activity of the Neuropetide Q polypeptide at its EC100 concentration. Antagonist activity of the candidate modulator will be expressed as a percentage of the inhibition of Neuropetide Q polypeptide activity at its EC80 concentration.

DiscoveRx Beta-Arrestin2 Assays:

Cells expressing recombinant human GALR2 receptor and the beta-arrestin2 (CHO-K1-hGALR2-Beta-arrestin 2) were plared at a density of 20.000 cells/well in a volume of 25 μl of cell culture medium (OCC2 medium, provided in the Kit) in 384-well tissue culture plate. After seeding the cells into the microplates, they were placed into a 37° C., 5% $CO_2$ in a humidified incubator for 24 hours prior to testing. Discard the OCC2 medium and replace it by HBSS 1× (Gibco, 14065), 20 mM HEPES (Gibco, 16530), 0.1% BSA (Sigma, A3803), pH 7.4, 20 μl per well. Stock solutions of candidate modulators were made up at a concentration of 10 mM in DMSO, and serially diluted in HBSS 1× (Gibco, 14065), 20 mM HEPES (Gibco, 16530), 0.1% BSA (Sigma, A3803), pH 7.4, to concentrations required for activation dose response curves. Remove the Path Hunter eXpress cells from the incubator and transfer 5 μl from compound plate. Incubate for 90 minutes at 37° C. During the incubation period, prepare a working solution of the detection reagents for each 384-well plate by mixing the following reagents: Cell Assay Buffer (19 parts), Substrate reagent 1 (5 parts), and Substrate Reagent 2 (1 part). Add 12.5 μl of prepared detection reagent per well and incubate for 90 minutes at room temperature (23° C.). Read samples on standard luminescence plate reader (Fluostar), under the following conditions: measurement interval: 0.1 second, interval time: 0.1 second, number of interval: 1, gain: auto-adjustment, emission filter: lens. Raw data were analysed with GraphPad Prism software for curve drawing and $EC_{50}$ calculation.

Agonistic activities ($EC_{50}$ values) of Neuropeptide Q polypeptides with respect to GALR2 receptor are displayed in Table 1.

TABLE 1

| Peptide | Assay | $EC_{50}$ (nM) |
|---|---|---|
| NPQ (SEQ ID NO: 13) | Aequorin | 2.34 |
| NPQ (SEQ ID NO: 13) | cAMP | 266 |
| NPQ (SEQ ID NO: 13) | IPone | 10.3 |
| NPQ (SEQ ID NO: 13) | GTP-γ-S | 166.9 |
| NPQ (SEQ ID NO: 13) | Arrestin (DiscoveRx) | 471.8 |
| NPQ (SEQ ID NO: 13) | Arrestin (Tango) | 732.4 |
| NPQ (SEQ ID NO: 13) | Binding | 92.4 |
| NPQ-Gly (SEQ ID NO: 14) | Aequorin | 5.70 |
| Rat NPQ (SEQ ID NO: 15) | Aequorin | 5.06 |
| Pro NPQ (36-58) (SEQ ID NO: 16) | Aequorin | 17.57 |
| Pro NPQ (73-116) (SEQ ID NO: 17) | Aequorin | >10 000 |
| NPQ-Gly (SEQ ID NO: 14) | FLIPR | 4.2 |
| NPQ (SEQ ID NO: 13) | FLIPR | 0.6 |
| NWTPQAMLYLKGA (SEQ ID NO: 18) | FLIPR | 4.3 |
| NWTPQAMLYLKG (SEQ ID NO: 19) | FLIPR | 6.7 |
| NWTPQAMLYLK (SEQ ID NO: 20) | FLIPR | 1.9 |
| NWTPQAMLYL (SEQ ID NO: 21) | FLIPR | 14 |

TABLE 1-continued

| Peptide | Assay | EC$_{50}$ (nM) |
|---|---|---|
| WTPQAMLYLKGAQG (SEQ ID NO: 22) | FLIPR | 4.8 |
| AWTPQAMLYLKGAQG (SEQ ID NO: 23) | FLIPR | 0.7 |
| NWAPQAMLYLKGAQG (SEQ ID NO: 24) | FLIPR | 10.9 |
| NWTAQAMLYLKGAQG (SEQ ID NO: 25) | FLIPR | 3.6 |
| NWTPAAMLYLKGAQG (SEQ ID NO: 26) | FLIPR | 12.5 |
| NWTPQAALYLKGAQG (SEQ ID NO: 27) | FLIPR | 3.4 |
| NWTPQAMAYLKGAQG (SEQ ID NO: 28) | FLIPR | 0.8 |
| NWTPQAMLYLAGAQG (SEQ ID NO: 29) | FLIPR | 9.6 |
| NWTPQAMLYLKAAQG (SEQ ID NO: 30) | FLIPR | 47 |
| NWTPQAMLYLKGAAG (SEQ ID NO: 31) | FLIPR | 0.1 |
| NWTPQAMLYLKGAQA (SEQ ID NO: 32) | FLIPR | 2.0 |
| PWTPQAMLYLKGAQG (SEQ ID NO: 33) | FLIPR | 0.1 |
| NWPPQAMLYLKGAQG (SEQ ID NO: 34) | FLIPR | 0.05 |
| NWTPPAMLYLKGAQG (SEQ ID NO: 35) | FLIPR | 97 |
| NWTPQPMLYLKGAQG (SEQ ID NO: 36) | FLIPR | 55 |
| NWTPQAMLYLPGAQG (SEQ ID NO: 37) | FLIPR | 296 |
| NWTPQAMLYLKPAQG (SEQ ID NO: 38) | FLIPR | 20 |
| NWTPQAMLYLKGPQG (SEQ ID NO: 39) | FLIPR | 0.3 |
| NWTPQAMLYLKGAPG (SEQ ID NO: 40) | FLIPR | 0.2 |
| NWTPQAMLYLKGAQP (SEQ ID NO: 41) | FLIPR | 0.3 |

ABBREVIATIONS

ATP: Adenosine Tri Phosphate
BSA: Bovine Serum Albumin
cAMP: Cyclic Adenosine MonoPhosphate
CAT: Chloramphenicol AcetylTransferase
CDR: Complementarity-Determining Region
CNS Central Nervous System
CPM Counts Per Minute
CRE: cAMP Response Element
CRE: Cyclization Recombination
CRF Corticotrophin Releasing Factor
DAG: DiAcylGlycerol
DMEM: Dulbecco's Modified Eagle Medium
DMSO: Dimethylsulfoxide
DR: Dorsal Raphe
DRN: Dorsal Raphe Nucleus
DTT: DiThioThreitol
EDTA: EthyleneDiamineTetraacetic Acid
EGTA: Ethylene Glycol-bis(beta-aminoethyl ether)-N,N,N',N'-Tetra Acetic acid
ELISA: Enzyme-Linked Immunosorbent Assay
FBS: Fetal Bovine Serum
FLIPR: Fluorometric Imaging Plate Reader
FLP: FLiPpase Recombinase Enzyme
FRET: Fluorescence Energy Transfer
GALR1: Galanin Receptor 1
GALR2: Galanin Receptor 2
GALR3: Galanin Receptor 3
GDP: Guanosine DiPhosphate
GFP: Green Fluorescent Protein
GPCR: G Protein Coupled Receptor
GTP: Guanosine TriPhosphate
HBSS: Hanks Balanced Salt Solution
HEPES: 4-(2-HydroxyEthyl)-1-piperazineEthaneSulfonic acid
HIV: Human Immunodeficiency Virus
HTRF: Homogeneous Time Resolved Fluorescence
icv: Intracerebroventricular
KRH: Krebs-Ringer-Hepes
NEAA: Non Essential Amino Acids
NPQ: Neuropeptide Q
Kd: Equilibrium Constant for Dissociation
LC: Locus Coeruleus
MAP (kinase): Mitogen-Activated Protein (kinase)
PBS: Phosphate Buffered Saline
PCR: Polymerase Chain Reaction
PEI: PolyEthylenlmine
PNS Peripheral Nervous System
RT/PCR: Reverse Transcriptase/Polymerase Chain Reaction
RLU Relative Light Units

The invention claimed is:

1. A method of identifying an agent that modulates the function of GALR2 comprising:
   a) contacting a GALR2 polypeptide with a Neuropeptide Q polypeptide in the presence and absence of a candidate modulator under conditions permitting the interaction of the Neuropeptide Q polypeptide to the GALR2 polypeptide, wherein the candidate modulator is a synthetic compound; and
   b) measuring the interaction of the GALR2 polypeptide to the Neuropeptide Q polypeptide, wherein an increase or a decrease in interaction in the presence of the candidate modulator, relative to the interaction in the absence of the candidate modulator, identifies the candidate modulator as an agent that modulates the function of GALR2, wherein the GALR2 polypeptide is a polypeptide having at least 95% amino acid sequence identity to SEQ ID NO: 2, 4, 6, 8, or 10, and
   wherein the Neuropeptide Q polypeptide is a polypeptide having at least 90% amino acid sequence identity to SEQ ID NO: 13-16 or 18-41.

2. A method of identifying an agent that modulates the function of GALR2 comprising:
   a) contacting a GALR2 polypeptide with a Neuropeptide Q polypeptide in the presence and absence of a candidate modulator under conditions permitting the interaction of the Neuropeptide Q polypeptide to the GALR2 polypeptide, wherein the candidate modulator is a synthetic compound; and b) measuring a signaling activity of the GALR2 polypeptide, wherein a change in the activity in the presence of the candidate modulator relative to the activity in the absence of the candidate modulator identifies the candidate modulator as an agent that modulates the function of GALR2, wherein the GALR2 polypeptide is a polypeptide having at least 95% amino acid sequence identity to SEQ ID NO: 2, 4, 6, 8, or 10, and wherein the Neuropeptide Q polypeptide is a polypeptide having at least 90% amino acid sequence identity to SEQ ID NO: 13-16 or 18-41.

3. A method of identifying an agent that modulates the function of GALR2 comprising:
 a) contacting a GALR2 polypeptide with a candidate modulator, wherein the candidate modulator is a synthetic compound;
 b) measuring a signaling activity of the GALR2 polypeptide in the presence of the candidate modulator; and
 c) comparing the activity measured in the presence of the candidate modulator to the activity measured in a sample in which the GALR2 polypeptide is contacted with a Neuropeptide Q polypeptide, wherein the candidate modulator is identified as an agent that modulates the function of GALR2 when the amount of the activity measured in the presence of the candidate modulator is at least 50% of the amount induced by the Neuropeptide Q polypeptide present at its $EC_{50}$, wherein the GALR2 polypeptide is a polypeptide having at least 95% amino acid sequence identity to SEQ ID NO: 2, 4, 6, 8, or 10, and wherein the Neuropeptide Q polypeptide is a polypeptide having at least 90% amino acid sequence identity to SEQ ID NO: 13-16 or 18-41.

4. The method according to claim 1, wherein said agent that modulates the function of GALR2 is present in a sample.

5. The method according to claim 1, wherein the measuring is performed using a method comprising label displacement, surface plasmon resonance, fluorescence resonance energy transfer, fluorescence quenching, or fluorescence polarization.

6. The method according to claim 1, wherein said GALR2 polypeptide sequence is SEQ ID NO: 2, and said Neuropeptide Q polypeptide sequence is SEQ ID NO: 13, SEQ ID NO: 14, or SEQ ID NO: 15, and
 wherein said Neuropeptide Q polypeptide specifically binds to said GALR2 polypeptide.

7. The method according to claim 1, wherein said GALR2 polypeptide sequence is SEQ ID NO: 2, SEQ ID NO: 4, SEQ ID NO: 6, SEQ ID NO: 8 or SEQ ID NO. 10.

8. The method according to claim 1, wherein said Neuropeptide Q poly-peptide sequence is SEQ ID No: 13, SEQ ID No: 14, SEQ ID No: 15, SEQ ID NO: 16, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, or SEQ ID NO: 41.

9. The method according to claim 1, wherein said Neuropeptide Q polypeptide sequence is SEQ ID NO: 13, SEQ ID NO: 14, SEQ ID NO: 15, or SEQ ID NO: 16.

10. The method according to claim 1, wherein the Neuropeptide Q polypeptide is detectably labeled.

11. The method according to claim 1, wherein the GALR2 polypeptide is expressed in or on a cell.

12. The method according to claim 1, wherein the GALR2 polypeptide is present in a cell membrane.

13. The method according to claim 11, wherein said cell is a COS-7-cell, a CHO cell, a U2OS cell, a LM (TK-) cell, a NIH-3T3 cell, a HEK cell, a K-562 cell or an 1321N1 astrocytoma cell.

14. The method according to claim 1, wherein the GALR2 polypeptide is present in or on synthetic liposomes or virus-induced budding membranes.

15. The method according to claim 1, wherein the method is further performed in the presence of $G\alpha 16$.

16. The method according to claim 1, wherein the agent is a peptide, a polypeptide, an antibody or antigen-binding fragment thereof, a lipid, a carbohydrate, a nucleic acid, or a small organic molecule.

17. The method according to claim 2, wherein the step of measuring a signaling activity comprises measuring guanine nucleotide binding or exchange, adenyl cyclase activity, cAMP, beta-arrestin 1 recruitment, beta-arrestin 2 recruitment, Protein Kinase C activity, phosphatidylinositol breakdown, diacylglycerol, inositol triphosphate, intracellular calcium, arachidonic acid, MAP kinase activity, tyrosine kinase activity, or reporter gene expression.

18. The method according to claim 12, wherein said cell is a COS-7-cell, a CHO cell, a U2OS cell, a LM (TK-) cell, a NIH-3T3 cell, a HEK cell, a K-562 cell or an 1321N1 astrocytoma cell.

19. The method according to claim 3, wherein the step of measuring a signaling activity comprises measuring guanine nucleotide binding or exchange, adenyl cyclase activity, cAMP, beta-arrestin 1 recruitment, beta-arrestin 2 recruitment, Protein Kinase C activity, phosphatidylinositol breakdown, diacylglycerol, inositol triphosphate, intracellular calcium, arachidonic acid, MAP kinase activity, tyrosine kinase activity, or reporter gene expression.

* * * * *

SEQUENCE LISTING

<160> NUMBER OF SEQ ID NOS: 41

<210> SEQ ID NO 1
<211> LENGTH: 1164
<212> TYPE: DNA
<213> ORGANISM: Homo sapiens

<400> SEQUENCE: 1
atgaacgtct cgggctgccc aggggccggg aacgcgagcc aggcgggcgg cgggggaggc    60

```
tggcacccCg aggcggtcat cgtgcccctg ctcttcgcgc tcatcttcct cgtgggcacc    120
gtgggcaaca cgctggtgct ggcggtgctg ctgcgcggcg gccaggcggt cagcactacc    180
aacctgttca tccttaacct gggcgtggcc gacctgtgtt tcatcctgtg ctgcgtgccc    240
ttccaggcca ccatctacac cctggacggc tgggtgttcg gctcgctgct gtgcaaggcg    300
gtgcacttcc tcatcttcct caccatgcac gccagcagct tcacgctggc cgccgtctcc    360
ctggacaggt atctggccat ccgctacccg ctgcactccc gcgagctgcg cacgcctcga    420
aacgcgctgg cagccatcgg gctcatctgg gggctgtcgc tgctcttctc cgggccctac    480
ctgagctact accgccagtc gcagctggcc aacctgaccg tgtgccatcc cgcgtggagc    540
gcccctcgcc gccgcgccat ggacatctgc accttcgtct tcagctacct gcttcctgtg    600
ctggttctcg gcctgaccta cgcgcgcacc ttgcgctacc tctggcgcgc cgtcgacccg    660
gtggccgcgg gctcgggtgc ccggcgcgcc aagcgcaagg tgacacgcat gatcctcatc    720
gtggccgcgc tcttctgcct ctgctggatg ccccaccacg cgctcatcct ctgcgtgtgg    780
ttcggccagt tcccgctcac gcgcgccact tatgcgcttc gcatcctctc gcacctggtc    840
tcctacgcca actcctgcgt caaccccatc gtttacgcgc tggtctccaa gcacttccgc    900
aaaggcttcc gcacgatctg cgcgggcctg ctgggccgtg ccccaggccg agcctcgggc    960
cgtgtgtgcg ctgccgcgcg gggcacccac agtggcagcg tgttggagcg cgagtccagc   1020
gacctgttgc acatgagcga ggcggcgggg gcccttcgtc cctgccccgg cgcttcccag   1080
ccatgcatcc tcgagccctg tcctggcccg tcctggcagg gcccaaaggc aggcgacagc   1140
atcctgacgg ttgatgtggc ctga                                          1164
```

<210> SEQ ID NO 2
<211> LENGTH: 387
<212> TYPE: PRT
<213> ORGANISM: Homo sapiens

<400> SEQUENCE: 2

```
Met Asn Val Ser Gly Cys Pro Gly Ala Gly Asn Ala Ser Gln Ala Gly
1               5                   10                  15

Gly Gly Gly Gly Trp His Pro Glu Ala Val Ile Val Pro Leu Leu Phe
                20                  25                  30

Ala Leu Ile Phe Leu Val Gly Thr Val Gly Asn Thr Leu Val Leu Ala
            35                  40                  45

Val Leu Leu Arg Gly Gly Gln Ala Val Ser Thr Thr Asn Leu Phe Ile
        50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Gly Trp Val Phe Gly Ser Leu
                85                  90                  95

Leu Cys Lys Ala Val His Phe Leu Ile Phe Leu Thr Met His Ala Ser
                100                 105                 110

Ser Phe Thr Leu Ala Ala Val Ser Leu Asp Arg Tyr Leu Ala Ile Arg
            115                 120                 125

Tyr Pro Leu His Ser Arg Glu Leu Arg Thr Pro Arg Asn Ala Leu Ala
        130                 135                 140

Ala Ile Gly Leu Ile Trp Gly Leu Ser Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175
```

```
Pro Ala Trp Ser Ala Pro Arg Arg Ala Met Asp Ile Cys Thr Phe
            180                 185                 190

Val Phe Ser Tyr Leu Leu Pro Val Leu Val Leu Gly Leu Thr Tyr Ala
        195                 200                 205

Arg Thr Leu Arg Tyr Leu Trp Arg Ala Val Asp Pro Val Ala Ala Gly
    210                 215                 220

Ser Gly Ala Arg Arg Ala Lys Arg Lys Val Thr Arg Met Ile Leu Ile
225                 230                 235                 240

Val Ala Ala Leu Phe Cys Leu Cys Trp Met Pro His His Ala Leu Ile
                245                 250                 255

Leu Cys Val Trp Phe Gly Gln Phe Pro Leu Thr Arg Ala Thr Tyr Ala
            260                 265                 270

Leu Arg Ile Leu Ser His Leu Val Ser Tyr Ala Asn Ser Cys Val Asn
    275                 280                 285

Pro Ile Val Tyr Ala Leu Val Ser Lys His Phe Arg Lys Gly Phe Arg
    290                 295                 300

Thr Ile Cys Ala Gly Leu Leu Gly Arg Ala Pro Gly Arg Ala Ser Gly
305                 310                 315                 320

Arg Val Cys Ala Ala Ala Arg Gly Thr His Ser Gly Ser Val Leu Glu
                325                 330                 335

Arg Glu Ser Ser Asp Leu Leu His Met Ser Glu Ala Gly Ala Leu
            340                 345                 350

Arg Pro Cys Pro Gly Ala Ser Gln Pro Cys Ile Leu Glu Pro Cys Pro
        355                 360                 365

Gly Pro Ser Trp Gln Gly Pro Lys Ala Gly Asp Ser Ile Leu Thr Val
    370                 375                 380

Asp Val Ala
385

<210> SEQ ID NO 3
<211> LENGTH: 1116
<212> TYPE: DNA
<213> ORGANISM: mouse

<400> SEQUENCE: 3
atgaatggct cggacagcca gggggcggag gactcgagcc aggaaggtgg cggcggctgg      60
cagcccgagg cggtcctcgt acccctattt ttcgcgctca tcttcctcgt gggcgctgtg     120
ggcaacgcgc tggtgctggc ggtgctgctg cgcggcggcc aggcggtcag caccacgaac     180
ctattcatcc tcaacctggg tgtggccgac ctgtgtttca tcctgtgctg cgtgcctttc     240
caggccacca tctataccct ggacgattgg gtgtttggct cactgctctg caaggccgtt     300
catttcctca tcttcctcac tatgcacgcc agcagcttca cgctggccgc tgtctcgctg     360
gacaggtatc tggccatccg ctacccgctg cactcccgag agttgcgcac acctcgaaac     420
gcgctggcgg ccatcgggct catctggggg ctagcactgc tcttctccgg ccctacctg     480 agctactaca gtcagtcgca gctggccaat ctgacggtgt gccacccagc gtggagcgca     540
ccacgacgtc gcgccatgga cctctgcact tttgtctta gctacctgtt gccagtgctg     600
gtgctcagcc tgacctatgc gcgcacccctg cactacctct ggcgcacagt tgacccagta     660
gctgcaggct caggttccca gcgcgccaag cgcaaggtga cacggatgat cgtcatcgtg     720
gcggtactct ctgcctctg ttggatgccc accacgcgc ttatcctctg cgtgtggttt     780
ggtcgctttc cgctcacgcg tgccacttac gccctgcgca tccttcaca tctagtatct     840
```

-continued

| | |
|---|---|
| tatgccaact cgtgtgtcaa ccccatcgtt tatgctctgg tctccaagca tttccgcaaa | 900 |
| ggtttccgca aaatctgcgc gggcctgcta cgccgtgccc cgaggagagc ttcaggccga | 960 |
| gtgtgcatcc tggcgcctgg aaaccatagt ggtggcatgc tggaacctga gtccacagac | 1020 |
| ctgacacagg tgagcgaggc agccgggccc ctcgtccccg cacccgcact tcccaactgc | 1080 |
| acaaccttga gtagaacccct cgatccagcc tgttaa | 1116 |

<210> SEQ ID NO 4
<211> LENGTH: 371
<212> TYPE: PRT
<213> ORGANISM: mouse

<400> SEQUENCE: 4

Met Asn Gly Ser Asp Ser Gln Gly Ala Glu Asp Ser Ser Gln Glu Gly
1               5                   10                  15

Gly Gly Gly Trp Gln Pro Glu Ala Val Leu Val Pro Leu Phe Phe Ala
                20                  25                  30

Leu Ile Phe Leu Val Gly Ala Val Gly Asn Ala Leu Val Leu Ala Val
            35                  40                  45

Leu Leu Arg Gly Gly Gln Ala Val Ser Thr Thr Asn Leu Phe Ile Leu
        50                  55                  60

Asn Leu Gly Val Ala Asp Leu Cys Phe Ile Leu Cys Cys Val Pro Phe
65                  70                  75                  80

Gln Ala Thr Ile Tyr Thr Leu Asp Asp Trp Val Phe Gly Ser Leu Leu
                85                  90                  95

Cys Lys Ala Val His Phe Leu Ile Phe Leu Thr Met His Ala Ser Ser
            100                 105                 110

Phe Thr Leu Ala Ala Val Ser Leu Asp Arg Tyr Leu Ala Ile Arg Tyr
        115                 120                 125

Pro Leu His Ser Arg Glu Leu Arg Thr Pro Arg Asn Ala Leu Ala Ala
130                 135                 140

Ile Gly Leu Ile Trp Gly Leu Ala Leu Leu Phe Ser Gly Pro Tyr Leu
145                 150                 155                 160

Ser Tyr Tyr Ser Gln Ser Gln Leu Ala Asn Leu Thr Val Cys His Pro
                165                 170                 175

Ala Trp Ser Ala Pro Arg Arg Arg Ala Met Asp Leu Cys Thr Phe Val
            180                 185                 190

Phe Ser Tyr Leu Leu Pro Val Leu Val Leu Ser Leu Thr Tyr Ala Arg
        195                 200                 205

Thr Leu His Tyr Leu Trp Arg Thr Val Asp Pro Val Ala Ala Gly Ser
210                 215                 220

Gly Ser Gln Arg Ala Lys Arg Lys Val Thr Arg Met Ile Val Ile Val
225                 230                 235                 240

Ala Val Leu Phe Cys Leu Cys Trp Met Pro His His Ala Leu Ile Leu
                245                 250                 255

Cys Val Trp Phe Gly Arg Phe Pro Leu Thr Arg Ala Thr Tyr Ala Leu
            260                 265                 270

Arg Ile Leu Ser His Leu Val Ser Tyr Ala Asn Ser Cys Val Asn Pro
        275                 280                 285

Ile Val Tyr Ala Leu Val Ser Lys His Phe Arg Lys Gly Phe Arg Lys
290                 295                 300

Ile Cys Ala Gly Leu Leu Arg Arg Ala Pro Arg Arg Ala Ser Gly Arg
305                 310                 315                 320

Val Cys Ile Leu Ala Pro Gly Asn His Ser Gly Gly Met Leu Glu Pro

```
                325                 330                 335
Glu Ser Thr Asp Leu Thr Gln Val Ser Glu Ala Ala Gly Pro Leu Val
            340                 345                 350

Pro Ala Pro Ala Leu Pro Asn Cys Thr Thr Leu Ser Arg Thr Leu Asp
        355                 360                 365

Pro Ala Cys
    370

<210> SEQ ID NO 5
<211> LENGTH: 1119
<212> TYPE: DNA
<213> ORGANISM: rat

<400> SEQUENCE: 5
atgaatggct ccggcagcca gggcgcggag aacacgagcc aggaaggcgg tagcggcggc      60
tggcagcctg aggcggtcct tgtaccccta ttttcgcgc tcatcttcct cgtgggcacc     120
gtgggcaacg cgctggtgct ggcggtgctg ctgcgcggcg gccaggcggt cagcaccacc     180
aacctgttca tcctcaacct gggcgtggcc gacctgtgtt tcatcctgtg ctgcgtgcct     240
ttccaggcca ccatctacac cctggacgac tgggtgttcg gctcgctgct ctgcaaggct     300
gttcatttcc tcatctttct cactatgcac gccagcagct tcacgctggc cgccgtctcc     360
ctggacaggt atctggccat ccgctacccg ctgcactccc gagagttgcg cacacctcga     420
aacgcgctgg ccgccatcgg gctcatctgg ggctagcac tgctcttctc cgggccctac     480
ctgagctact accgtcagtc gcagctggcc aacctgacag tatgccaccc agcatggagc     540
gcacctcgac gtcgagccat ggacctctgc accttcgtct ttagctacct gctgccagtg     600
ctagtcctca gtctgaccta tgcgcgtacc ctgcgctacc tctggcgcac agtcgacccg     660
gtgactgcag gctcaggttc ccagcgcgcc aaacgcaagg tgacacggat gatcatcatc     720
gtggcggtgc ttttctgcct ctgttggatg ccccaccacg cgcttatcct ctgcgtgtgg     780
tttggtcgct tcccgctcac gcgtgccact tacgcgttgc gcatccttc acacctagtt     840 tcctatgcca actcctgtgt caaccccatc gtttacgctc tggtctccaa gcatttccgt     900
aaaggttttc gcaaaatctg cgcgggcctg ctgcgccctg ccccgaggcg agcttcgggc     960
cgagtgagca tcctggcgcc tgggaaccat agtggcagca tgctggaaca ggaatccaca    1020
gacctgacac aggtgagcga ggcagccggg cccttgtcc caccaccgc acttcccaac    1080 tgcacagcct cgagtagaac cctggatccg gcttgttaa                           1119

<210> SEQ ID NO 6
<211> LENGTH: 372
<212> TYPE: PRT
<213> ORGANISM: rat

<400> SEQUENCE: 6

Met Asn Gly Ser Gly Ser Gln Gly Ala Glu Asn Thr Ser Gln Glu Gly
1               5                   10                  15

Gly Ser Gly Gly Trp Gln Pro Glu Ala Val Leu Val Pro Leu Phe Phe
            20                  25                  30

Ala Leu Ile Phe Leu Val Gly Thr Val Gly Asn Ala Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80
```

```
Phe Gln Ala Thr Ile Tyr Thr Leu Asp Asp Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ala Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Ala Met Asp Leu Cys Thr Phe
            180                 185                 190

Val Phe Ser Tyr Leu Leu Pro Val Leu Val Leu Ser Leu Thr Tyr Ala
        195                 200                 205

Arg Thr Leu Arg Tyr Leu Trp Arg Thr Val Asp Pro Val Thr Ala Gly
    210                 215                 220

Ser Gly Ser Gln Arg Ala Lys Arg Lys Val Thr Arg Met Ile Ile Ile
225                 230                 235                 240

Val Ala Val Leu Phe Cys Leu Cys Trp Met Pro His His Ala Leu Ile
                245                 250                 255

Leu Cys Val Trp Phe Gly Arg Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300

Lys Ile Cys Ala Gly Leu Leu Arg Pro Ala Pro Arg Arg Ala Ser Gly
305                 310                 315                 320

Arg Val Ser Ile Leu Ala Pro Gly Asn His Ser Gly Ser Met Leu Glu
                325                 330                 335

Gln Glu Ser Thr Asp Leu Thr Gln Val Ser Glu Ala Ala Gly Pro Leu
            340                 345                 350

Val Pro Pro Pro Ala Leu Pro Asn Cys Thr Ala Ser Ser Arg Thr Leu
        355                 360                 365

Asp Pro Ala Cys
    370

<210> SEQ ID NO 7
<211> LENGTH: 1164
<212> TYPE: DNA
<213> ORGANISM: rhesus macaque

<400> SEQUENCE: 7
atgaacgtct cggtctgccc aggagccggg aacgcgagcc aggtgggctg cgggggcggc     60
tggcaccccg aggcggtcat cgtgcccctg ctcttcgcgc tcatcttcct cgtgggcacc    120
gtgggcaaca cgctggtgct ggcggtgctg ctgcgcggcg ccaggcggt cagcaccacc    180 aacctgttca ttctcaacct gggcgtggcc gacctgtgtt tcatcctgtg ctgcgtgccc    240
ttccaggcca ccatctacac gctggacggc tgggtgttcg gctcgctgct gtgcaaggct    300
gtgcacttcc tcatcttcct caccatgcac gccagcagct cacgctggcc gctgtctcg    360 ctggacaggt atctggccat ccgctacccg ctgcactccc gcgaactgcg cacgcctcga    420
```

```
aacgcgctgg cagcgatcgc gctcatctgg gggctgtcgc tgctcttctc tgggccctac    480
ctgagttact accgccagtc gcagctggcc aacctgaccg tgtgccatcc cgcgtggagc    540
gcccctcgcc gccgcgccat ggacctctgc accttcgtct tcagctacct gcttccggtg    600
ctggttctca gcctgaccta cgcgcgcacc ctgcgctacc tctggcgtgc cgtcgacccg    660
gtggccgcgg gctcgggtgc ccggcgcgcc aaacgtaagg tgacacgcat gatccttatc    720
gtggccgcgc tcttctgcct ctgctggatg ccccaccacg cgctcatcct ctgcgtgtgg    780
ttcggccatt tcccgctcac gcgcgctact tacgcgcttc gcatcctctc gcacctggtc    840
tcctacgcca actcctgcgt gaaccccatc gtttacgcgc tggtctccaa acacttccgc    900
aaaggcttcc gcaagatctg cgcgggcctg ctgggccgtg ccccacgccg agcctcgggc    960
cgcgtgtgcg ctgccgcgcc gggcacccac agtggcagcg tgctggagcg cgagtccacc   1020
gacctgtcgc acgtgagcga ggcggcagag gcccttcatc cctgccccgg cgcttcccag   1080
ccgtgcaccc tcgagcctgg tcccggcccg tcttggcggg gcccaaaggc aggcaacagc   1140
atcctgacag ttgatgtgac ctga                                          1164

<210> SEQ ID NO 8
<211> LENGTH: 387
<212> TYPE: PRT
<213> ORGANISM: rhesus macaque

<400> SEQUENCE: 8

Met Asn Val Ser Val Cys Pro Gly Ala Gly Asn Ala Ser Gln Val Gly
1               5                   10                  15

Cys Gly Gly Gly Trp His Pro Glu Ala Val Ile Val Pro Leu Leu Phe
            20                  25                  30

Ala Leu Ile Phe Leu Val Gly Thr Val Gly Asn Thr Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Gly Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Ala Leu Ile Trp Gly Leu Ser Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Ala Met Asp Leu Cys Thr Phe
            180                 185                 190

Val Phe Ser Tyr Leu Leu Pro Val Leu Val Leu Ser Leu Thr Tyr Ala
        195                 200                 205

Arg Thr Leu Arg Tyr Leu Trp Arg Ala Val Asp Pro Val Ala Ala Gly
    210                 215                 220

Ser Gly Ala Arg Arg Ala Lys Arg Lys Val Thr Arg Met Ile Leu Ile
225                 230                 235                 240
```

```
Val Ala Ala Leu Phe Cys Leu Cys Trp Met Pro His Ala Leu Ile
                245                 250                 255
Leu Cys Val Trp Phe Gly His Phe Pro Leu Thr Arg Ala Thr Tyr Ala
            260                 265                 270
Leu Arg Ile Leu Ser His Leu Val Ser Tyr Ala Asn Ser Cys Val Asn
            275                 280                 285
Pro Ile Val Tyr Ala Leu Val Ser Lys His Phe Arg Lys Gly Phe Arg
            290                 295                 300
Lys Ile Cys Ala Gly Leu Leu Gly Arg Ala Pro Arg Arg Ala Ser Gly
305                 310                 315                 320
Arg Val Cys Ala Ala Ala Pro Gly Thr His Ser Gly Ser Val Leu Glu
                325                 330                 335
Arg Glu Ser Thr Asp Leu Ser His Val Ser Glu Ala Glu Ala Leu
                340                 345                 350
His Pro Cys Pro Gly Ala Ser Gln Pro Cys Thr Leu Glu Pro Gly Pro
                355                 360                 365
Gly Pro Ser Trp Arg Gly Pro Lys Ala Gly Asn Ser Ile Leu Thr Val
            370                 375                 380
Asp Val Thr
385

<210> SEQ ID NO 9
<211> LENGTH: 1164
<212> TYPE: DNA
<213> ORGANISM: chimpanzee

<400> SEQUENCE: 9
atgaacgtct cgggctgccc aggggccggg aacgcgagcc aggcgggcgg cggggaggc       60 tggcacccg  aggcggtcat cgtgccctg ctcttcgcgc tcatcttcct cgtgggcatc      120
gtgggcaaca cgctggtgct ggcggtgctg ctgcgcggcg ccaggcggt cagcaccacc      180 aacctgttca tccttaacct gggcgtagcc gacctgtgtt tcatcctgtg ctgcgtgccc      240
ttccaggcca ccatctacac cctggacggg tgggtgttcg gctcgctgct gtgcaaggcg      300
gtgcacttct tcatcttcct caccatgcac gccagcagct tcacgctggc cgccgtctcc      360
ctggacaggt atctggccat ccgctacccg ctgcactccc gcgagctgcg cacgcctcga      420
aacgcgctgg cagccatcgg gctcatctgg ggctgtcgc tgctcttctc cgggccctac      480
ctgagctact accgccagtc gcagctggcc aacctgaccg tgtgccatcc tgcgtggagc      540
gcccctcgcc gccgcgccat ggacatctgc accttcgtct tcagctacct gcttcctgtg      600
ctggttctcg gcctgaccta cgcgcgcacc ttgcgctacc tctggcgcgc cgtcgacccg      660
gtggccgcgg gctcgggtgc ccggcgcgcc aagcgcaagg tgacacgcat gatcctcatc      720
gtggccgcgc tcttctgcct ctgctggatg ccccaccacg cgctcatcct ctgcgtgtgg      780
ttcggccatt tcccgctcac gcgcgccact tatgcgcttc gcatcctctc gcacctggtc      840
tcctacgcca actcctgcgt caaccccatc gtttacgcgc tggtctccaa gcacttccgc      900
aaaggcttcc gcacgatctg cgcgggcctg ctgggccgtg ccccaggccg agcctcgggc      960
cgtgtgtgcg ctgccgcgcg gggcacccac agtggcagcg tgctgagcg cgagtccagc     1020 gacctgttgc acatgagcga ggcggcgggg gccttcgtc cctgccccgg cgcttcccag     1080
ccatgcaccc tcgagccctg tcctggcccg tcctggcagg gcccaaaggc aggcgacagc     1140
atcctgacgg ttgatgtggc ctga                                            1164
```

-continued

```
<210> SEQ ID NO 10
<211> LENGTH: 387
<212> TYPE: PRT
<213> ORGANISM: chimpanzee

<400> SEQUENCE: 10

Met Asn Val Ser Gly Cys Pro Gly Ala Gly Asn Ala Ser Gln Ala Gly
1               5                   10                  15

Gly Gly Gly Gly Trp His Pro Glu Ala Val Ile Val Pro Leu Leu Phe
            20                  25                  30

Ala Leu Ile Phe Leu Val Gly Ile Val Gly Asn Thr Leu Val Leu Ala
        35                  40                  45

Val Leu Leu Arg Gly Gly Gln Ala Val Ser Thr Thr Asn Leu Phe Ile
50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Gly Trp Val Phe Gly Ser Leu
                85                  90                  95

Leu Cys Lys Ala Val His Phe Ile Phe Leu Thr Met His Ala Ser
            100                 105                 110

Ser Phe Thr Leu Ala Ala Val Ser Leu Asp Arg Tyr Leu Ala Ile Arg
            115                 120                 125

Tyr Pro Leu His Ser Arg Glu Leu Arg Thr Pro Arg Asn Ala Leu Ala
130                 135                 140

Ala Ile Gly Leu Ile Trp Gly Leu Ser Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Ala Met Asp Ile Cys Thr Phe
            180                 185                 190

Val Phe Ser Tyr Leu Leu Pro Val Leu Val Leu Gly Leu Thr Tyr Ala
            195                 200                 205

Arg Thr Leu Arg Tyr Leu Trp Arg Ala Val Asp Pro Val Ala Ala Gly
210                 215                 220

Ser Gly Ala Arg Arg Ala Lys Arg Lys Val Thr Arg Met Ile Leu Ile
225                 230                 235                 240

Val Ala Ala Leu Phe Cys Leu Cys Trp Met Pro His His Ala Leu Ile
                245                 250                 255

Leu Cys Val Trp Phe Gly His Phe Pro Leu Thr Arg Ala Thr Tyr Ala
            260                 265                 270

Leu Arg Ile Leu Ser His Leu Val Ser Tyr Ala Asn Ser Cys Val Asn
            275                 280                 285

Pro Ile Val Tyr Ala Leu Val Ser Lys His Phe Arg Lys Gly Phe Arg
290                 295                 300

Thr Ile Cys Ala Gly Leu Leu Gly Arg Ala Pro Gly Arg Ala Ser Gly
305                 310                 315                 320

Arg Val Cys Ala Ala Ala Arg Gly Thr His Ser Gly Ser Val Leu Glu
                325                 330                 335

Arg Glu Ser Ser Asp Leu Leu His Met Ser Glu Ala Ala Gly Ala Leu
            340                 345                 350

Arg Pro Cys Pro Gly Ala Ser Gln Pro Cys Thr Leu Glu Pro Cys Pro
            355                 360                 365

Gly Pro Ser Trp Gln Gly Pro Lys Ala Gly Asp Ser Ile Leu Thr Val
370                 375                 380
```

Asp Val Ala
385

<210> SEQ ID NO 11
<211> LENGTH: 351
<212> TYPE: DNA
<213> ORGANISM: Homo sapiens

<400> SEQUENCE: 11

```
atgaaggggac tcagaagtct ggcagcaaca accttggctc ttttcctggt gtttgttttc    60
ctgggaaact ccagctgcgc tccgcagaga ctgttggaga gaaggaactg gactcctcaa   120
gctatgctct acctgaaagg ggcacagggt cgccgcttca tctccgacca gagccggaga   180
aaggacctct ccgaccggcc actgccggaa agacgaagcc caaatcccca actactaact   240
attccggagg cagcaaccat cttactggcg tcccttcaga aatcaccaga agatgaagaa   300
aaaaactttg atcaaaccag attcctggaa gacagtctgc ttaactggtg a             351
```

<210> SEQ ID NO 12
<211> LENGTH: 115
<212> TYPE: PRT
<213> ORGANISM: Homo sapiens

<400> SEQUENCE: 12

Met Lys Gly Leu Arg Ser Leu Ala Ala Thr Thr Leu Ala Leu Phe Leu
1               5                   10                  15

Val Phe Val Phe Leu Gly Asn Ser Ser Cys Ala Pro Gln Arg Leu Leu
            20                  25                  30

Glu Arg Arg Asn Trp Thr Pro Gln Ala Met Leu Tyr Leu Lys Gly Ala
        35                  40                  45

Gln Gly Arg Arg Phe Ile Ser Asp Gln Ser Arg Arg Lys Asp Leu Ser
    50                  55                  60

Asp Arg Pro Leu Pro Glu Arg Arg Ser Pro Asn Pro Gln Leu Leu Thr
65                  70                  75                  80

Ile Pro Glu Ala Ala Thr Ile Leu Leu Ala Ser Leu Gln Lys Ser Pro
                85                  90                  95

Glu Asp Glu Glu Lys Asn Phe Asp Gln Thr Arg Phe Leu Glu Asp Ser
            100                 105                 110

Leu Leu Asn
        115

<210> SEQ ID NO 13
<211> LENGTH: 14
<212> TYPE: PRT
<213> ORGANISM: Homo sapiens

<400> SEQUENCE: 13

Asn Trp Thr Pro Gln Ala Met Leu Tyr Leu Lys Gly Ala Gln
1               5                   10

<210> SEQ ID NO 14
<211> LENGTH: 15
<212> TYPE: PRT
<213> ORGANISM: Homo sapiens

<400> SEQUENCE: 14

Asn Trp Thr Pro Gln Ala Met Leu Tyr Leu Lys Gly Ala Gln Gly
1               5                   10                  15

```
<210> SEQ ID NO 15
<211> LENGTH: 16
<212> TYPE: PRT
<213> ORGANISM: rat

<400> SEQUENCE: 15

Asn Trp Thr Pro Gln Ala Met Leu Tyr Leu Lys Gly Ala Gln Gly His
1               5                   10                  15

<210> SEQ ID NO 16
<211> LENGTH: 23
<212> TYPE: PRT
<213> ORGANISM: Homo sapiens

<400> SEQUENCE: 16

Asn Trp Thr Pro Gln Ala Met Leu Tyr Leu Lys Gly Ala Gln Gly Arg
1               5                   10                  15

Arg Phe Ile Ser Asp Gln Ser
            20

<210> SEQ ID NO 17
<211> LENGTH: 44
<212> TYPE: PRT
<213> ORGANISM: Homo sapiens

<400> SEQUENCE: 17

Ser Pro Asn Pro Gln Leu Leu Thr Ile Pro Glu Ala Ala Thr Ile Leu
1               5                   10                  15

Leu Ala Ser Leu Gln Lys Ser Pro Glu Asp Glu Glu Lys Asn Phe Asp
                20                  25                  30

Gln Thr Arg Phe Leu Glu Asp Ser Leu Leu Asn Trp
            35                  40

<210> SEQ ID NO 18
<211> LENGTH: 13
<212> TYPE: PRT
<213> ORGANISM: Artificial Sequence
<220> FEATURE:
<223> OTHER INFORMATION: truncated human Neuropeptide Q amino acid
      sequence

<400> SEQUENCE: 18

Asn Trp Thr Pro Gln Ala Met Leu Tyr Leu Lys Gly Ala
1               5                   10

<210> SEQ ID NO 19
<211> LENGTH: 12
<212> TYPE: PRT
<213> ORGANISM: Artificial Sequence
<220> FEATURE:
<223> OTHER INFORMATION: truncated human Neuropeptide Q amino acid
      sequence

<400> SEQUENCE: 19

Asn Trp Thr Pro Gln Ala Met Leu Tyr Leu Lys Gly
1               5                   10

<210> SEQ ID NO 20
<211> LENGTH: 11
<212> TYPE: PRT
<213> ORGANISM: Artificial Sequence
<220> FEATURE:
<223> OTHER INFORMATION: truncated human Neuropeptide Q amino acid
      sequence

<400> SEQUENCE: 20
```

```
Asn Trp Thr Pro Gln Ala Met Leu Tyr Leu Lys
1               5                  10

<210> SEQ ID NO 21
<211> LENGTH: 10
<212> TYPE: PRT
<213> ORGANISM: Artificial Sequence
<220> FEATURE:
<223> OTHER INFORMATION: truncated human Neuropeptide Q amino acid
      sequence

<400> SEQUENCE: 21

Asn Trp Thr Pro Gln Ala Met Leu Tyr Leu
1               5                  10

<210> SEQ ID NO 22
<211> LENGTH: 14
<212> TYPE: PRT
<213> ORGANISM: Artificial Sequence
<220> FEATURE:
<223> OTHER INFORMATION: truncated human Neuropeptide Q - Glycine amino
      acid sequence

<400> SEQUENCE: 22

Trp Thr Pro Gln Ala Met Leu Tyr Leu Lys Gly Ala Gln Gly
1               5                  10

<210> SEQ ID NO 23
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by alanine

<400> SEQUENCE: 23

Ala Trp Thr Pro Gln Ala Met Leu Tyr Leu Lys Gly Ala Gln Gly
1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by alanine

<400> SEQUENCE: 24

Asn Trp Ala Pro Gln Ala Met Leu Tyr Leu Lys Gly Ala Gln Gly
1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by alanine

<400> SEQUENCE: 25

Asn Trp Thr Ala Gln Ala Met Leu Tyr Leu Lys Gly Ala Gln Gly
1               5                  10                  15

<210> SEQ ID NO 26
<211> LENGTH: 15
<212> TYPE: PRT
<213> ORGANISM: Artificial Sequence
```

```
<220> FEATURE:
<223> OTHER INFORMATION: human Neuropeptide Q - Glycine amino acid
      sequence with substitution by alanine

<400> SEQUENCE: 26

Asn Trp Thr Pro Ala Ala Met Leu Tyr Leu Lys Gly Ala Gln Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by alanine

<400> SEQUENCE: 27

Asn Trp Thr Pro Gln Ala Ala Leu Tyr Leu Lys Gly Ala Gln Gly
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by alanine

<400> SEQUENCE: 28

Asn Trp Thr Pro Gln Ala Met Ala Tyr Leu Lys Gly Ala Gln Gly
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by alanine

<400> SEQUENCE: 29

Asn Trp Thr Pro Gln Ala Met Leu Tyr Leu Ala Gly Ala Gln Gly
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by alanine

<400> SEQUENCE: 30

Asn Trp Thr Pro Gln Ala Met Leu Tyr Leu Lys Ala Ala Gln Gly
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by alanine

<400> SEQUENCE: 31

Asn Trp Thr Pro Gln Ala Met Leu Tyr Leu Lys Gly Ala Ala Gly
1               5                   10                  15
```

<210> SEQ ID NO 32
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by alanine

<400> SEQUENCE: 32

Asn Trp Thr Pro Gln Ala Met Leu Tyr Leu Lys Gly Ala Gln Ala
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by proline

<400> SEQUENCE: 33

Pro Trp Thr Pro Gln Ala Met Leu Tyr Leu Lys Gly Ala Gln Gly
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by proline

<400> SEQUENCE: 34

Asn Trp Pro Pro Gln Ala Met Leu Tyr Leu Lys Gly Ala Gln Gly
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by proline

<400> SEQUENCE: 35

Asn Trp Thr Pro Pro Ala Met Leu Tyr Leu Lys Gly Ala Gln Gly
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by proline

<400> SEQUENCE: 36

Asn Trp Thr Pro Gln Pro Met Leu Tyr Leu Lys Gly Ala Gln Gly
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by proline

```
<400> SEQUENCE: 37

Asn Trp Thr Pro Gln Ala Met Leu Tyr Leu Pro Gly Ala Gln Gly
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by proline

<400> SEQUENCE: 38

Asn Trp Thr Pro Gln Ala Met Leu Tyr Leu Lys Pro Ala Gln Gly
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by proline

<400> SEQUENCE: 39

Asn Trp Thr Pro Gln Ala Met Leu Tyr Leu Lys Gly Pro Gln Gly
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by proline

<400> SEQUENCE: 40

Asn Trp Thr Pro Gln Ala Met Leu Tyr Leu Lys Gly Ala Pro Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: human Neuropeptide Q - Glycine amino acid
      sequence with substitution by proline

<400> SEQUENCE: 41

Asn Trp Thr Pro Gln Ala Met Leu Tyr Leu Lys Gly Ala Gln Pro
1               5                   10                  15
```